US011007705B2

(12) United States Patent
Angelini et al.

(10) Patent No.: US 11,007,705 B2
(45) Date of Patent: May 18, 2021

(54) HIGH SPEED 3D PRINTING SYSTEM FOR WOUND AND TISSUE REPLACEMENT

(71) Applicants: University of Florida Research Foundation, Inc., Gainesville, FL (US); Georgia Tech Research Corporation, Atlanta, GA (US); Samantha M. Marquez, Midlothian, VA (US)

(72) Inventors: Thomas Ettor Angelini, Gainesville, FL (US); Wallace Gregory Sawyer, Gainesville, FL (US); Kyle Gene Rowe, Gainesville, FL (US); Tapomoy Bhattacharjee, Gainesville, FL (US); Alberto Fernandez-Nieves, Atlanta, GA (US); Ya-Wen Chang, Atlanta, GA (US); Samantha M. Marquez, Midlothian, VA (US)

(73) Assignees: University of Florida Research Foundation, Inc., Gainesville, FL (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/549,083

(22) PCT Filed: Feb. 12, 2016

(86) PCT No.: PCT/US2016/017810
§ 371 (c)(1),
(2) Date: Aug. 4, 2017

(87) PCT Pub. No.: WO2016/130953
PCT Pub. Date: Aug. 18, 2016

(65) Prior Publication Data
US 2018/0021140 A1   Jan. 25, 2018

Related U.S. Application Data

(60) Provisional application No. 62/116,351, filed on Feb. 13, 2015.

(51) Int. Cl.
*A61F 2/30* (2006.01)
*B29C 64/118* (2017.01)
(Continued)

(52) U.S. Cl.
CPC ........ *B29C 64/118* (2017.08); *A61F 2/30942* (2013.01); *A61L 27/16* (2013.01);
(Continued)

(58) Field of Classification Search
CPC .................................................. B29C 64/106
See application file for complete search history.

(56) References Cited

U.S. PATENT DOCUMENTS 2,340,110 A   1/1944   D Alelio
2,340,111 A   1/1944   D'Alelio et al.
(Continued)

FOREIGN PATENT DOCUMENTS

CA   2822487 A1   7/2012
CN   1450953      10/2003
(Continued)

OTHER PUBLICATIONS

Pfister, Journal of PolymerScience vol. 42 2004 p. 624-638 (Year: 2004).*
(Continued)

*Primary Examiner* — Joseph A Miller, Jr.
(74) *Attorney, Agent, or Firm* — Thomas|Horstemeyer LLP

(57) ABSTRACT

A method or apparatus for creating a three-dimensional tissue construct of a desired shape for repair or replacement of a portion of an organism. The method may comprise injecting at least one biomaterial in a three-dimensional pattern into a first material such that the at least one biomaterial is held in the desired shape of the tissue construct by the first material. The apparatus may comprise an
(Continued)

injector configured to inject at least one biomaterial in a three-dimensional pattern into a first material such that the at least one biomaterial is held in the desired shape of the tissue construct by the first material. The first material may comprise a yield stress material, which may be a material exhibiting Herschel-Bulkley behavior. The tissue construct may have a smallest feature size of ten micrometers or less.

39 Claims, 41 Drawing Sheets

(51) Int. Cl.
| | |
|---|---|
| *C12N 5/00* | (2006.01) |
| *B33Y 80/00* | (2015.01) |
| *B33Y 70/00* | (2020.01) |
| *A61L 27/16* | (2006.01) |
| *A61L 27/18* | (2006.01) |
| *A61L 27/26* | (2006.01) |
| *A61L 27/36* | (2006.01) |
| *A61L 27/50* | (2006.01) |
| *A61L 27/52* | (2006.01) |
| *A61L 27/54* | (2006.01) |
| *A61L 27/60* | (2006.01) |
| *C12N 5/071* | (2010.01) |
| *A61K 35/00* | (2006.01) |
| *B29L 31/00* | (2006.01) |

(52) U.S. Cl.
CPC .............. *A61L 27/18* (2013.01); *A61L 27/26* (2013.01); *A61L 27/3604* (2013.01); *A61L 27/3625* (2013.01); *A61L 27/507* (2013.01); *A61L 27/52* (2013.01); *A61L 27/54* (2013.01); *A61L 27/60* (2013.01); *B33Y 70/00* (2014.12); *B33Y 80/00* (2014.12); *C12N 5/0062* (2013.01); *C12N 5/069* (2013.01); *C12N 5/0686* (2013.01); *A61F 2002/30962* (2013.01); *A61F 2240/002* (2013.01); *A61K 35/00* (2013.01); *A61L 2300/414* (2013.01); *A61L 2300/64* (2013.01); *A61L 2430/20* (2013.01); *A61L 2430/26* (2013.01); *B29L 2031/7532* (2013.01); *C12N 2513/00* (2013.01); *C12N 2533/30* (2013.01); *C12N 2533/74* (2013.01); *C12N 2533/80* (2013.01)

(56) References Cited

U.S. PATENT DOCUMENTS

| | | | |
|---|---|---|---|
| 2,533,635 A | 12/1950 | Seymour et al. |
| 3,940,351 A | 2/1976 | Schlatzer, Jr. |
| 4,062,817 A | 12/1977 | Westerman |
| 4,631,557 A | 12/1986 | Cooke et al. |
| 5,034,486 A | 7/1991 | Tzai et al. |
| 5,034,487 A | 7/1991 | Tazi et al. |
| 5,034,488 A | 7/1991 | Tazi et al. |
| 5,073,491 A | 12/1991 | Familletti |
| 5,078,994 A | 1/1992 | Nair et al. |
| 5,310,779 A | 5/1994 | Lai |
| 5,349,030 A | 9/1994 | Long, II et al. |
| 5,470,900 A | 11/1995 | Sasaki et al. |
| 5,474,719 A | 12/1995 | Fan |
| 5,654,362 A | 8/1997 | Schulz, Jr. et al. |
| 5,697,441 A | 12/1997 | Vercaemer et al. |
| 6,279,655 B1 | 8/2001 | Pafitis et al. |
| 6,375,880 B1 | 4/2002 | Cooper et al. |
| 6,476,147 B1 | 11/2002 | Sullivan et al. |
| 6,486,901 B1 | 11/2002 | Deboer et al. |
| 6,936,212 B1 | 8/2005 | Crawford |
| 6,942,830 B2 | 9/2005 | Muelhaupt et al. |
| 7,049,346 B1 | 5/2006 | Van Bladel et al. |
| 7,064,151 B1 | 6/2006 | Berge et al. |
| 7,179,872 B2 | 2/2007 | McCormick et al. |
| 7,285,237 B2 | 10/2007 | Newell et al. |
| 8,133,341 B2 | 3/2012 | Nealey et al. |
| 10,150,258 B2 | 12/2018 | Feinberg et al. |
| 2004/0101518 A1 | 5/2004 | Vacanti et al. |
| 2004/0120920 A1 | 6/2004 | Lion et al. |
| 2004/0242837 A1 | 12/2004 | Toyoda et al. |
| 2005/0247357 A1 | 11/2005 | Welle |
| 2005/0282934 A1 | 12/2005 | Brinkmann et al. |
| 2006/0136058 A1 | 6/2006 | Pietrzak |
| 2006/0156978 A1* | 7/2006 | Lipson ............... A61L 27/36 118/708 |
| 2006/0211790 A1 | 9/2006 | Dimotakis et al. |
| 2009/0101271 A1 | 4/2009 | Ishida |
| 2009/0171001 A1 | 7/2009 | Lin et al. |
| 2010/0069522 A1 | 3/2010 | Linhardt et al. |
| 2010/0102415 A1 | 4/2010 | Millward et al. |
| 2010/0137534 A1 | 6/2010 | Magnet et al. |
| 2010/0183977 A1 | 7/2010 | Wang et al. |
| 2010/0184147 A1 | 7/2010 | Cheng et al. |
| 2010/0304088 A1 | 12/2010 | Steeman et al. |
| 2010/0321448 A1 | 12/2010 | Buestgens et al. |
| 2011/0064810 A1 | 3/2011 | Ghanavi |
| 2011/0103174 A1 | 5/2011 | Jung et al. |
| 2011/0256085 A1 | 10/2011 | Talingting Pabalan et al. |
| 2012/0040013 A1 | 2/2012 | Owens et al. |
| 2012/0171258 A1 | 7/2012 | Sefton et al. |
| 2013/0004385 A1 | 1/2013 | Lee et al. |
| 2013/0029125 A1 | 1/2013 | Tse et al. |
| 2013/0317131 A1 | 11/2013 | Scales et al. |
| 2013/0333891 A1 | 12/2013 | Fripp et al. |
| 2013/0344601 A1 | 12/2013 | Soman et al. |
| 2014/0005178 A1 | 2/2014 | Kumar et al. |
| 2014/0186952 A1 | 7/2014 | Alsberg |
| 2014/0224349 A1 | 8/2014 | Ducrée et al. |
| 2014/0275317 A1 | 9/2014 | Moussa |
| 2014/0295541 A1 | 10/2014 | Nakanishi et al. |
| 2014/0037746 A1 | 12/2014 | Trefonas, III et al. |
| 2015/0056317 A1 | 2/2015 | Chen |
| 2015/0057786 A1 | 2/2015 | Murphy et al. |
| 2015/0091217 A1 | 4/2015 | Araki |
| 2015/0093465 A1 | 4/2015 | Page |
| 2015/0104639 A1 | 4/2015 | Schroeyers et al. |
| 2015/0022558 A1 | 8/2015 | Ohori et al. |
| 2015/0217024 A1 | 8/2015 | Wang et al. |
| 2015/0031537 A1 | 11/2015 | Mehta et al. |
| 2016/0062230 A1 | 3/2016 | Wu et al. |
| 2016/0106663 A1 | 4/2016 | Gulbin |
| 2016/0167312 A1 | 6/2016 | Feinberg et al. |
| 2016/0019689 A1 | 7/2016 | Ohori et al. |
| 2016/0215130 A1 | 7/2016 | Esseghir et al. |

FOREIGN PATENT DOCUMENTS

| | | |
|---|---|---|
| CN | 102164661 | 8/2011 |
| CN | 203305668 U | 11/2013 |
| FR | 2583334 | 12/1986 |
| FR | 2634686 | 2/1990 |
| JP | S61-98547 | 5/1986 |
| JP | 4636770 | 12/2010 |
| JP | 5167496 | 1/2013 |
| JP | 2014207886 | 11/2014 |
| WO | 0178968 | 10/2001 |
| WO | 2006027702 A2 | 3/2006 |
| WO | 2009139395 | 11/2009 |
| WO | 2012155110 | 11/2012 |
| WO | 2014024048 A1 | 2/2014 |
| WO | 2014039825 | 3/2014 |
| WO | 2014049204 | 4/2014 |
| WO | 2014182885 | 11/2014 |
| WO | 2014205261 A1 | 12/2014 |
| WO | 2014209994 | 12/2014 |
| WO | 2015017421 A2 | 2/2015 |
| WO | 2015019212 | 2/2015 |
| WO | 2015107333 | 7/2015 |
| WO | 2015138566 | 9/2015 |

(56) References Cited

FOREIGN PATENT DOCUMENTS

| WO | 2016044547 | | 3/2016 |
|---|---|---|---|
| WO | 2018187595 | A1 | 10/2018 |
| WO | 2018187780 | A1 | 10/2018 |

OTHER PUBLICATIONS

International Search Report issued by the European Patent Office for PCT/US16/17810, dated Jul. 12, 2016.
Hinton, et al. "Three-dimensional printing of complex biological structures by freeform reversible embedding of suspended hydrogels," Sci. Adv. 1:e1500758.
Hinton, et al. "3D Printing PDMS Elastomer in Hydrophilic Support Bath via Freeform Reversible Embedding." ACS Biomater. Sci. Eng., May 4, 2016 (web).
Office Action received in Japanese Patent Application No. 2017-530102 dated Oct. 29, 2019. [English translation provided].
Rudert, et al. "Experimental and numerical investigation of a viscoplastic Carbopol gel injected into a prototype 3D mold cavity," J Non-Newtonian Fluid Mechanics, 2009, vol. 161, pp. 60-68.
Khalil, et al. "Multi-nozzle deposition for construction of 3D biopolymer tissue scaffolds," Rapid Prototyping Journal, 2005, vol. 11/1, pp. 9-17.
Aldrich, S. (2019) "Thermal transitions of homopolymers: Glass transition & melting point."
Antoni, D.; et al (2015) "Three-Dimensional Cell Culture: a Breakthrough in Vivo." International journal of molecular sciences, 16(3), pp. 5517-5527.
Baudonnet, L., J-L. ; et al. (2004) "Effect of Dispersion Stirring Speed on the Particle Size Distribution and Rheological Properties of Three Carbomers." Journal of dispersion science and technology 25.2 : 183-192.
Bayliss, K., et al. (2011) "Comparing Colloidal Phase Separation Induced by Linear Polymer and by Microgel Particles." Soft Matter 7.21 : 10345-10352.
Beck, Emily C., et al. (2015) "Enabling Surgical Placement of Hydrogels Through Achieving Paste-Like Rheological Behavior in Hydrogel Precursor Solutions." Annals of biomedical engineering 43.10 : 2569-2576.
Bhattacharjee, Tapomoy, et al. (2016) "Liquid-Like Solids Support Cells in 3D." ACS Biomaterials Science & Engineering 2.10: 1787-1795.
Chang, Ya-Wen, et al. (2015) "Biofilm Formation in Geometries with Different Surface Curvature and Oxygen Availability." New Journal of Physics 17.3 : 033017.
Chinese Office Action dated Feb. 15, 2019 for Chinese Patent Application 2015800755428.
Conrad, Jacinta C; et al. (2008) "Structure of Colloidal Gels During Microchannel Flow." Langmuir 24.15 : pp. 7628-7634.
Derby, Brian. (2012) "Printing and Prototyping of Tissues and Scaffolds." Science 338.6109 : 921-926.
Ellis, Perry W., et al. (2018) "Curvature-Induced Defect Unbinding and Dynamics in Active Nematic Toroids." Nature Physics 14.1 : 85-90.
European Search Report in Appln. No. 15865693.4 dated Jul. 18, 2018.
Hardin, James O., et al. (2015) "Microfluidic Printheads for Multimaterial 3D Printing of Viscoelastic Inks." Advanced materials 27.21 : 3279-3284.
International Search Report for PCT/US2016/031385 dated Aug. 11, 2016.
International Search Report issued by U.S. For PCT/US2016/064771 dated Jan. 18, 2017.
International Search Report dated Feb. 16, 2016 for PCT Patent Application PCT/US2015/064063.
International Search Report dated Nov. 22, 2016 for PCT Patent Application No. PCT/US2016/050175.
International Search Report dated Dec. 30, 2016 for PCT Patent Application No. PCT/US2016/052102.
Jin, Yifei, et al. (2016) "Granular Gel Support-Enabled Extrusion of Three-Dimensional Alginate and Cellular Structures." Biofabrication 8.2 : 025016.
Landers, R, et al. Desktop manufacturing of complex objects, prototypes and biomedical scaffolds by means of computer-assisted design combined with computer-guided 3D plotting of polymers and reactive oligomers. Macromolecular Materials and Engineering 2000 282(1):17-21.
Liu, Guangyao,;et al (2012) "Development of Thermosensitive Copolymers of Poly (2-Methoxyethyl Acrylate-Co-Poly (Ethylene Glycol) Methyl Ether Acrylate) and their Nanogels Synthesized by RAFT Dispersion Polymerization in Nater." Polymer Chemistry 3.2 : 504-513.
Moxon, Samuel Robert, (2016) "Development of Biopolymer Hydrogels as Complex Tissue ENgineering Scaffolds" Doctoral thesis, University of Huddersfield. 211 pages.
Murphy, Sean V., ; et al (2014) "3D Bioprinting of Tissues and Organs." Nature biotechnology 32.8 : 773-785.
Muth, JT, et al. Embedded 3D Printing of Strain Sensors within Highly Stretchable Elastomers; 2014, 26, pp. 6307-6312, Advanced Materials; www.advmat.de.
Pairam, E., H. Le,; et al (2014) "Stability of Toroidal Droplets Inside Yield Stress Materials." Physical Review E 90.2 : 021002.
Pairam, Ekapop, et al. (2013) "Stable Nematic Droplets with Handles." Proceedings of the National Academy of Sciences 110.23 : 9295-9300.
Rieger, J. (1996) "The Glass Transition Temperature of Polystyrene." Journal of thermal analysis 46.3-4 : 965-972.
Roberts, Geraint P., ; et al (2001) "New Measurements of the Flow-Curves for Carbopol Dispersions Without Slip Artefacts." Rheologica Acta 40.5 : 499-503.
Schaefermeier PK, et al. Design and fabrication of three-dimensional scaffolds for tissue engineering of human heart valves. Eur Surg Res. 2009 42(1):49-53.
Search Report issued in EP Patent Application 16793291, dated Feb. 5, 2019.
Smith, D.,'Multi-Material Breakthrough for 3D Printing'[Press Release] The Technology Partnership, Sep. 4, 2013.
The Diamond Hotend [Product] RepRap.me: http://reprap.me/fronl-page-show/diamond-holend.hlml.
The Technology Partnership. [Relevant Business; Melbourn, UK] http://www.llp.com/printing.
Tumbleston, John R., et al.(2015) "Continuous Liquid Interface Production of 3D Objects." Science 347.6228 : 1349-1352.
Wu, Kun-Ta, et al. (2017) "Transition From Turbulent to Coherent Flows in Confined Three-Dimensional Active Fluids." Science 355.6331 : eaal1979.
Office Action received in Japanese Patent Application No. 2017-557950 dated Jan. 7, 2020. [English translation provided].
O'Bryan, C., et al., (2017). "Three-dimensional printing with sacrificial materials for soft matter manufacturing". MRS Bulletin, 42(8), 571-577. doi:10.1557/mrs.2017.167.
Zidoro, Dayane, et al. "Sensory evaluation and rheological behavior of commercial mayonnaise." International Journal of Food Engineering 3.1 (2007). (Year: 2007).
Gutowski, Iris A., et al. "Scaling and mesostructure of Carbopol dispersions." Rheologica acta 51.5 (2012): 441-450. (Year: 2012).
Kim, Jong-Yun, et al. "Rheological properties and microstructures of Carbopol gel network system." Colloid and Polymer Science 281.7 (2003): 614-623. (Year: 2003)
L. Baudonnet et al., "Effect of Dispersion Stirring Speed on the Particle Size Distribution and Rheological Properties of Threee Carbomers ", Journal of Dispersion Science and Technology vol. 25, No. 2, pp. 183-192, 2004.

* cited by examiner

HIGH SPEED 3D PRINTING SYSTEM FOR WOUND AND TISSUE REPLACEMENT

CROSS-REFERENCE TO RELATED APPLICATIONS

The present application is the U.S. National Stage of International Patent Application number PCT/US2016/017810, entitled "HIGH SPEED 3D PRINTING SYSTEM FOR WOUND AND TISSUE REPLACEMENT" filed Feb. 12, 2016, which claims priority under 35 U.S.C. § 119(e) to U.S. Provisional Patent Application No. 62/116,351, titled "High speed 3D printing system for wound and tissue replacement" and filed on Feb. 13, 2015, the contents of each of which are incorporated herein in their entirety.

This invention was made with Government support under DMR-1352043 awarded by the National Science Foundation. The Government has certain rights in this invention.

GOVERNMENT SUPPORT

This invention was made with Government support under DMR-1352043 awarded by the National Science Foundation. The Government has certain rights in this invention.

BACKGROUND

Biological tissue such as bone tissue, smooth muscle tissue, skeletal muscle tissue, and vascular tissue may need to be replaced in an organism in a number of situations. For example, an injury could cause tissue to be missing from a human's leg or other organ. A disease could result in the destruction or incomplete development of an organ or organs. Surgery could necessitate removal of tissue that may need to be replaced.

Use of three-dimensional scaffold as a template for cell regeneration is foundational to tissue engineering. Identification of the relationship of cell response on a two-dimensional (2D) surface to that of a three-dimensional (3D) object is increasingly important as biotechnology moves from conventional 2D to 3D cell cultures, which better mimic their in vivo counterparts.

Current state of the art generation of micron-to-millimeter scale surface topography relies on micropatterning, lithography techniques, or rapid prototyping based on the integration of 3D computer-aided design (CAD) and 3D printing or an additive layer method, which require specialized equipment or facilities, and often involve tedious procedures. Substrates with complex geometry, such as cylindrical, toroidal, and spherical scaffolds are challenging and time-consuming to fabricate with the aforementioned methods.

Existing scaffold processing techniques have evolved from the more traditional subtractive approaches, which involve constant removal of materials, to conventional additive approaches, which utilize solid free form fabrication by selectively adding materials layer by layer. Current commercially available 3D printing systems involve printing a solid support at the same time as the printed structure, layer by layer. After printing, the support material is washed away and discarded.

One free forming technique is electrospinning, a method that produces nonwoven fibrous structures with fiber diameters in the range of tens of nanometer to a micrometer. The polymer solution used is fed through a syringe and extruded from the spinneret (needle tip) connected to a high-voltage, where the nanofibers are generated. The 3D printing technique also utilizes a dispensing nozzle (inkjet print head) in its free forming process to deposit polymer powder and binding liquid in each layer.

SUMMARY

Some aspects include a method for creating a three-dimensional tissue construct of a desired shape for repair or replacement of a portion of an organism, such as for creating a three-dimensional tissue construct for use as a wound repair construct. The method may comprise injecting at least one biomaterial in a three-dimensional pattern into a first material such that the at least one biomaterial is held in the desired shape of the tissue construct by the first material.

Further aspects include an apparatus for creating a three-dimensional tissue construct of a desired shape for repair or replacement of a portion of an organism. The apparatus may comprise an injector configured to inject at least one biomaterial in a three-dimensional pattern into a first material such that the at least one biomaterial is held in the desired shape of the tissue construct by the first material.

Additional aspects include a three-dimensional tissue construct of a desired shape for repair or replacement of a portion of an organism. The tissue construct may comprise a plurality of biomaterials set in a three-dimensional structure having a smallest feature size of less than ten micrometers.

Accordingly, biomaterials used herein to form tissue constructs may be of a type that, themselves grow tissue cells such that the tissue construct itself turns into tissue of the organism. This cell growth may occur either before or after the biomaterial is removed from the material into which it has been printed. However, it should be appreciated that suitable biomaterials may also, when placed within or in contact with tissue of an organism, support growth of tissue cells from the organism such that the tissue construct acts as a tissue scaffold to support the growth of desired types of tissue in desired locations.

In one embodiment, there is provided a method for creating a three-dimensional tissue construct of a desired shape for repair or replacement of tissue of a tissue cavity of an organism. The method comprises injecting at least one biomaterial in a three-dimensional pattern into a first material such that the at least one biomaterial is held in the desired shape of the tissue construct by the first material.

In another embodiment, there is provided a method for creating a three-dimensional tissue construct of a desired shape for repair or replacement of tissue of a tissue cavity of an organism. The method comprises injecting at least one biomaterial and at least one cell in a three-dimensional pattern into a first material such that the at least one biomaterial and the at least one cell are held in the desired shape of the tissue construct by the first material.

In a further embodiment, there is provided an apparatus for creating a three-dimensional tissue construct of a desired shape for repair or replacement of tissue of a tissue cavity of an organism. The apparatus comprises an injector configured to inject at least one biomaterial in a three-dimensional pattern into a first material such that the at least one biomaterial is held in the desired shape of the tissue construct by the first material.

In another embodiment, there is provided an apparatus for creating a three-dimensional tissue construct of a desired shape for repair or replacement of tissue of a tissue cavity of an organism. The apparatus comprises an injector configured to inject at least one biomaterial and at least one cell in a three-dimensional pattern into a first material such that the at least one biomaterial and the at least one cell are held in the desired shape of the tissue construct by the first material.

In a further embodiment, there is provided a three-dimensional tissue construct of a desired shape for repair or replacement of tissue of a tissue cavity of an organism. The tissue construct comprises a plurality of biomaterials set in a three-dimensional structure having a smallest feature size of less than 1 millimeter.

In another embodiment, there is provided a three-dimensional tissue construct of a desired shape for repair or replacement of tissue of a tissue cavity of an organism. The tissue construct comprises a plurality of biomaterials and at least one cell set in a three-dimensional structure having a smallest feature size of less than 1 millimeter.

In a further embodiment, there is provided a three-dimensional tissue construct for use with a tissue cavity of an organism, the tissue cavity of the organism having a topographic shape. The three-dimensional tissue construct comprises at least one biomaterial in a 3D pattern, the at least one biomaterial having a shape complementary to the topographic shape of the tissue cavity.

In another embodiment, there is provided a three-dimensional tissue construct for use with a tissue cavity of an organism, the tissue cavity of the organism having a topographic shape. The three-dimensional tissue construct comprises at least one biomaterial and at least one cell in a 3D pattern, the 3D pattern having a shape complementary to the topographic shape of the tissue cavity.

DETAILED DESCRIPTION

Figure 1A:
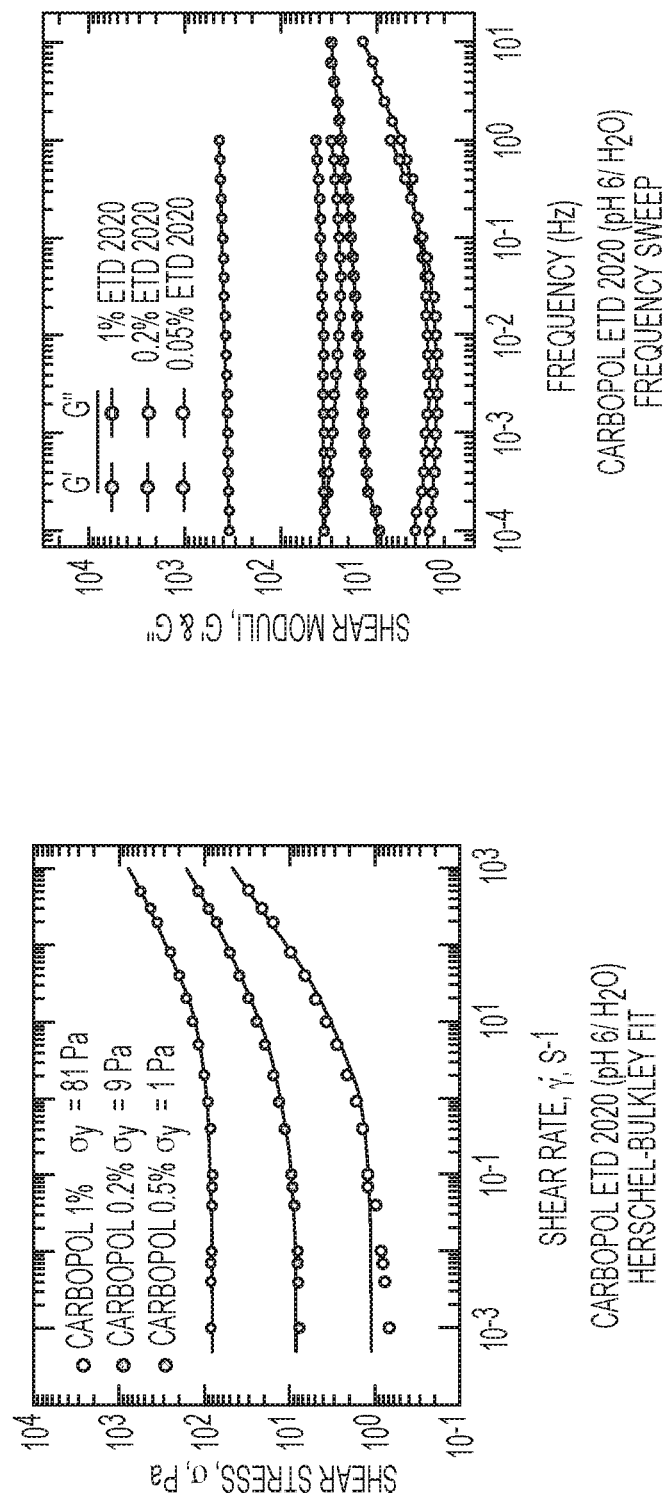
FIG. 1 (including FIGS. 1A-1G) includes plots of shear stress versus shear rate for some illustrative yield stress materials with which some embodiments may act, as well as some plots of shear moduli versus frequency for the illustrative yield stress materials.
Figure 1B:
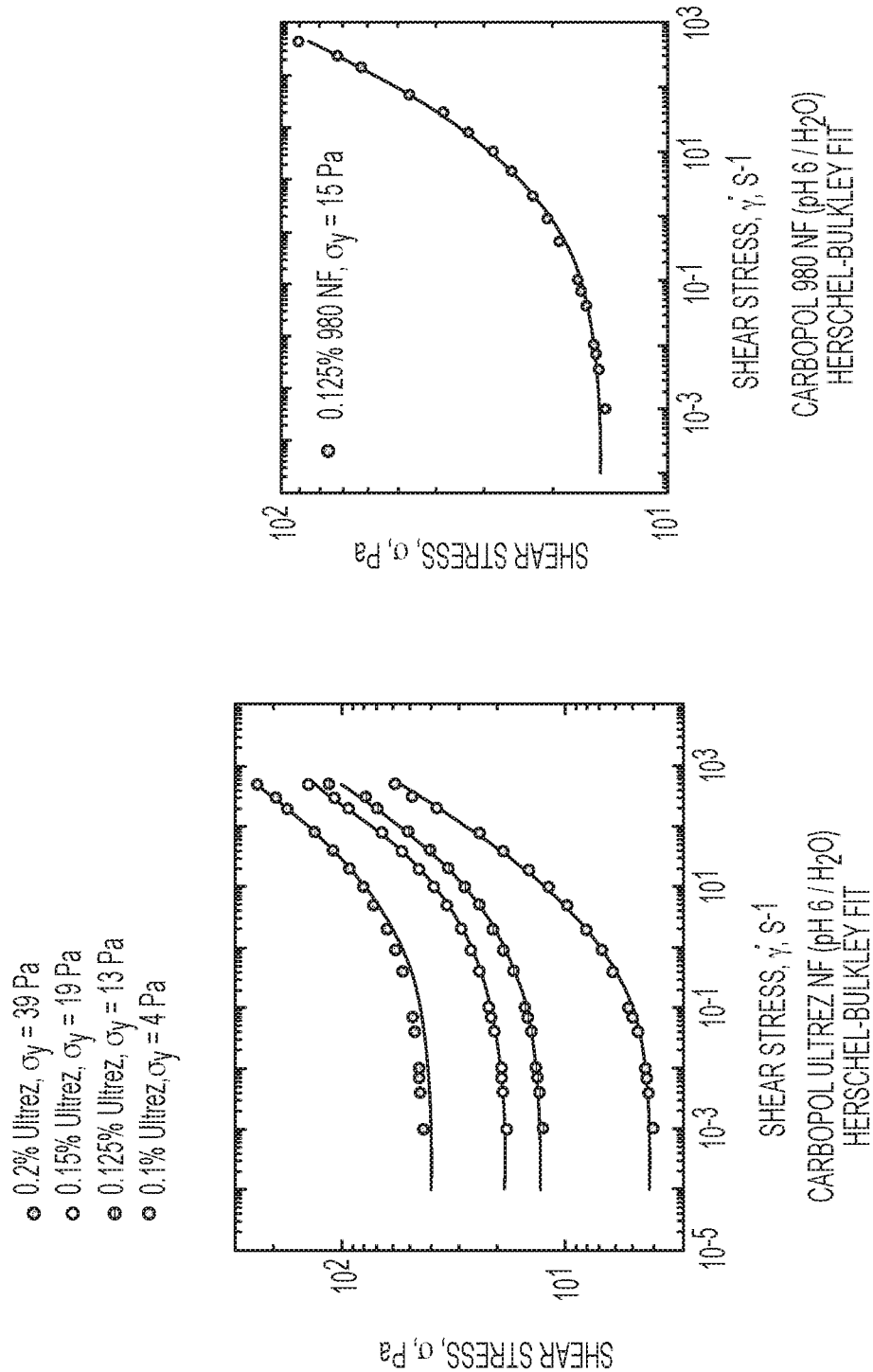
Figure 1C:
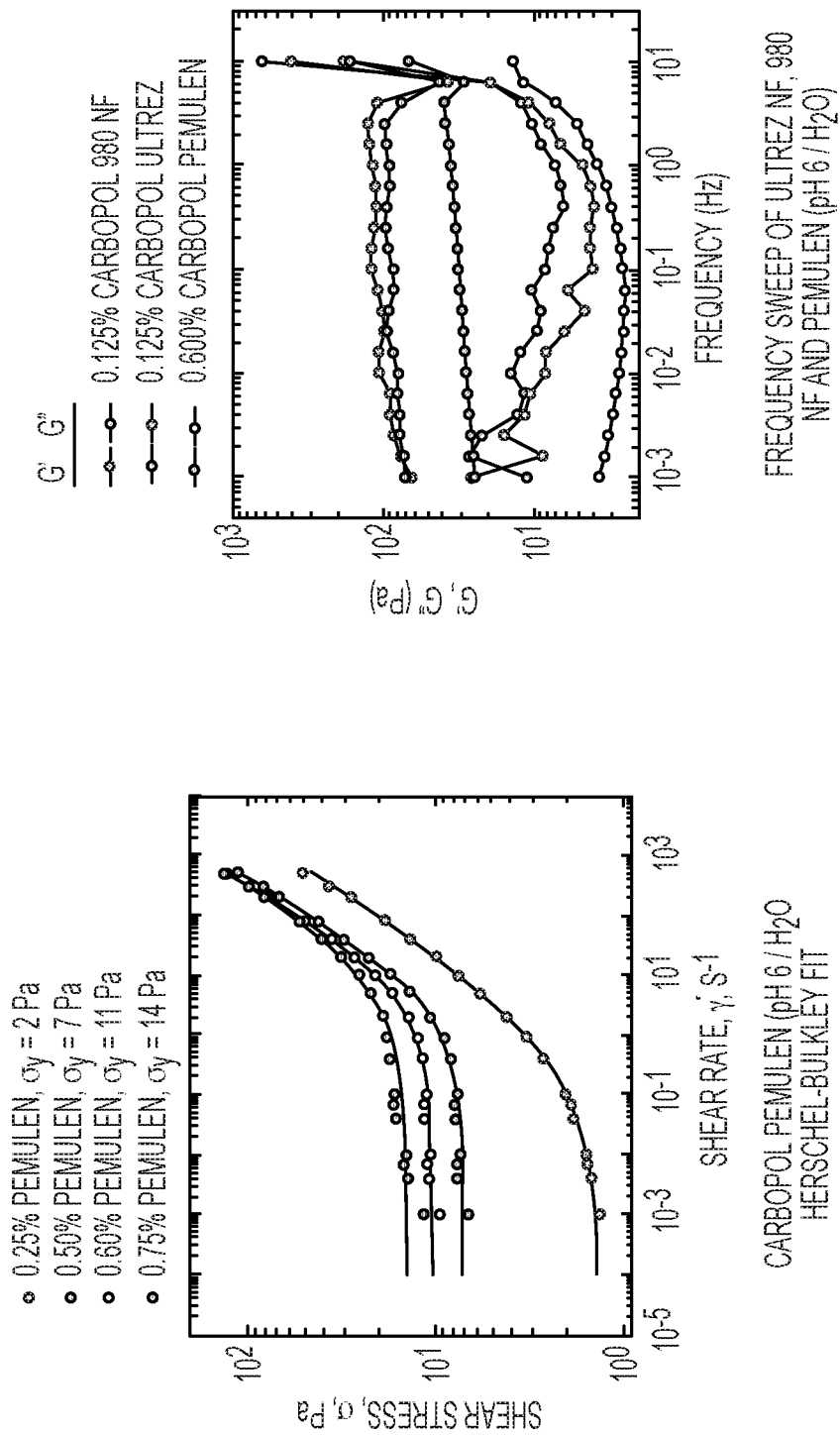
Figure 1D:
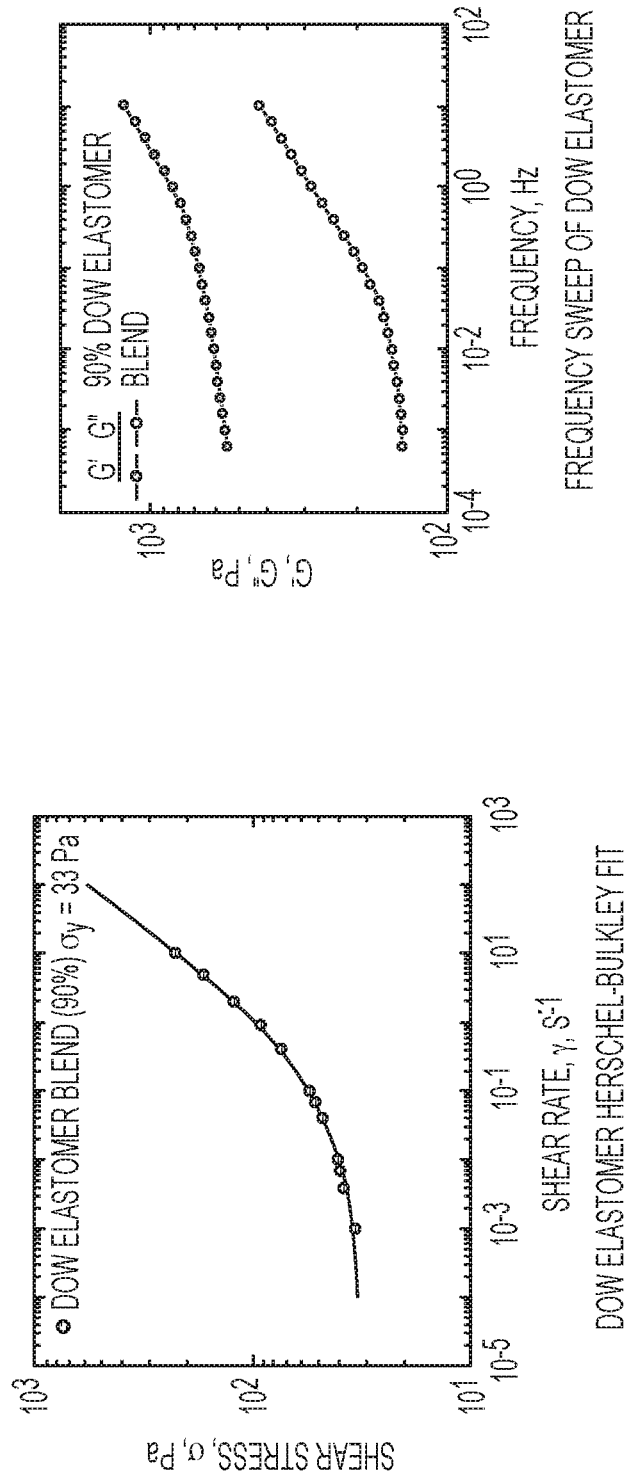
Figure 1E:
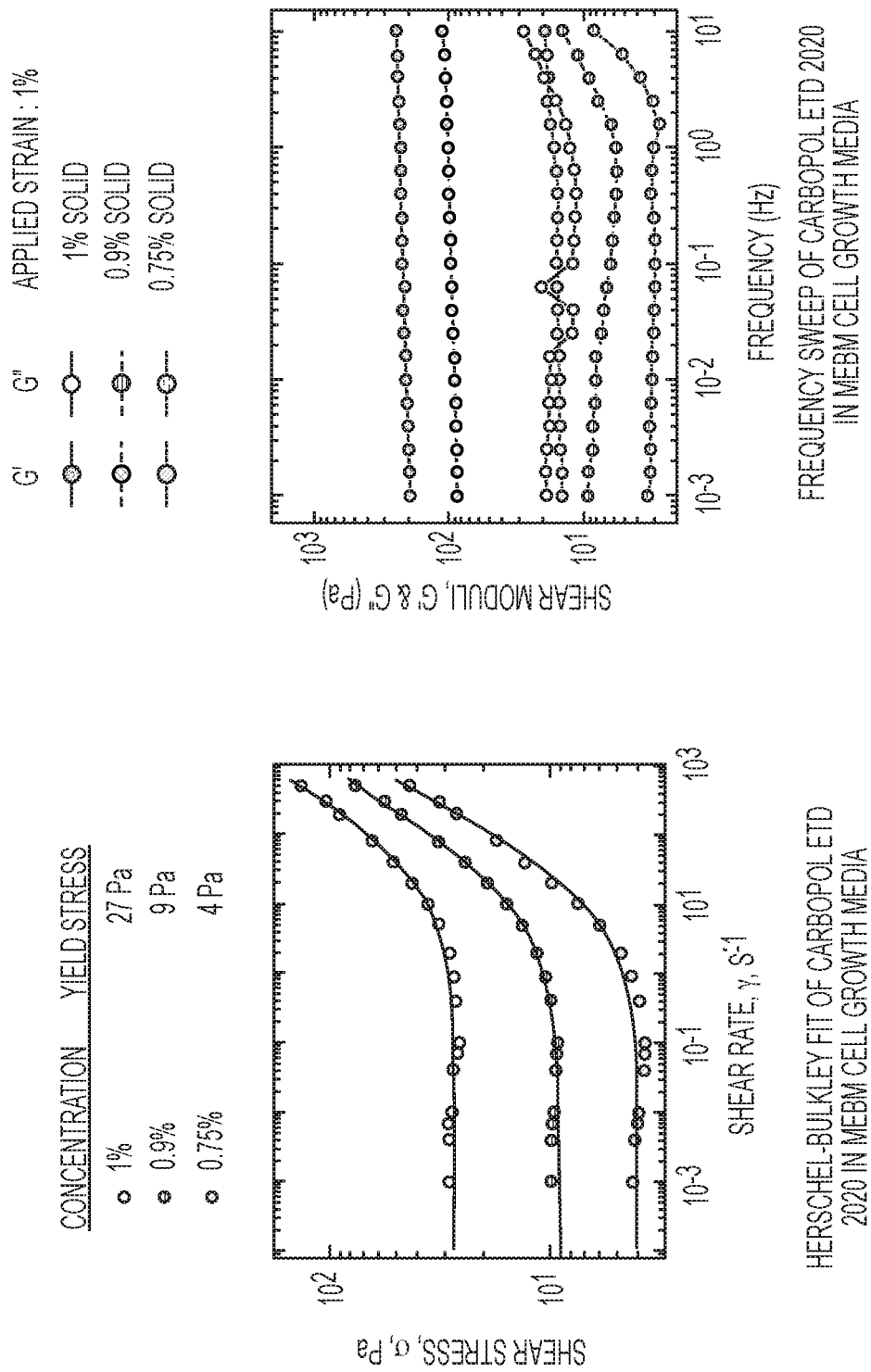
Figure 1F:
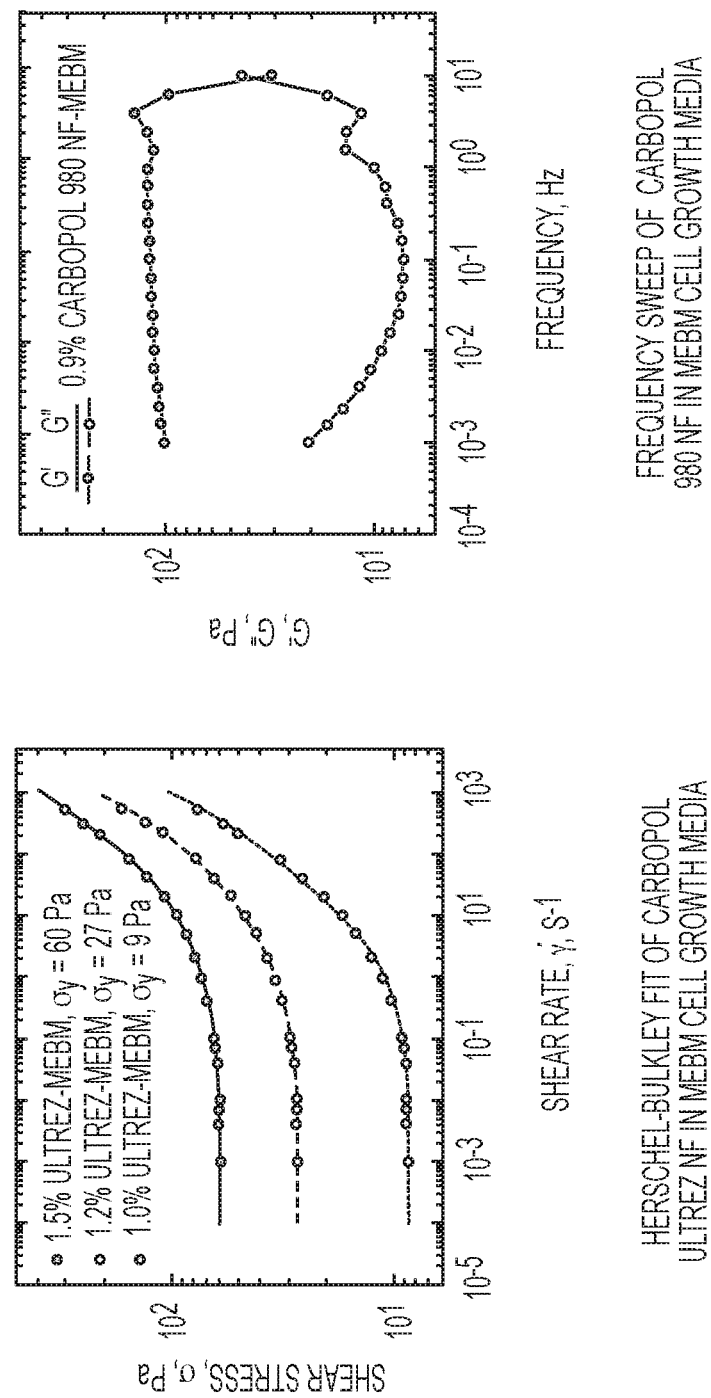
Figure 1G:
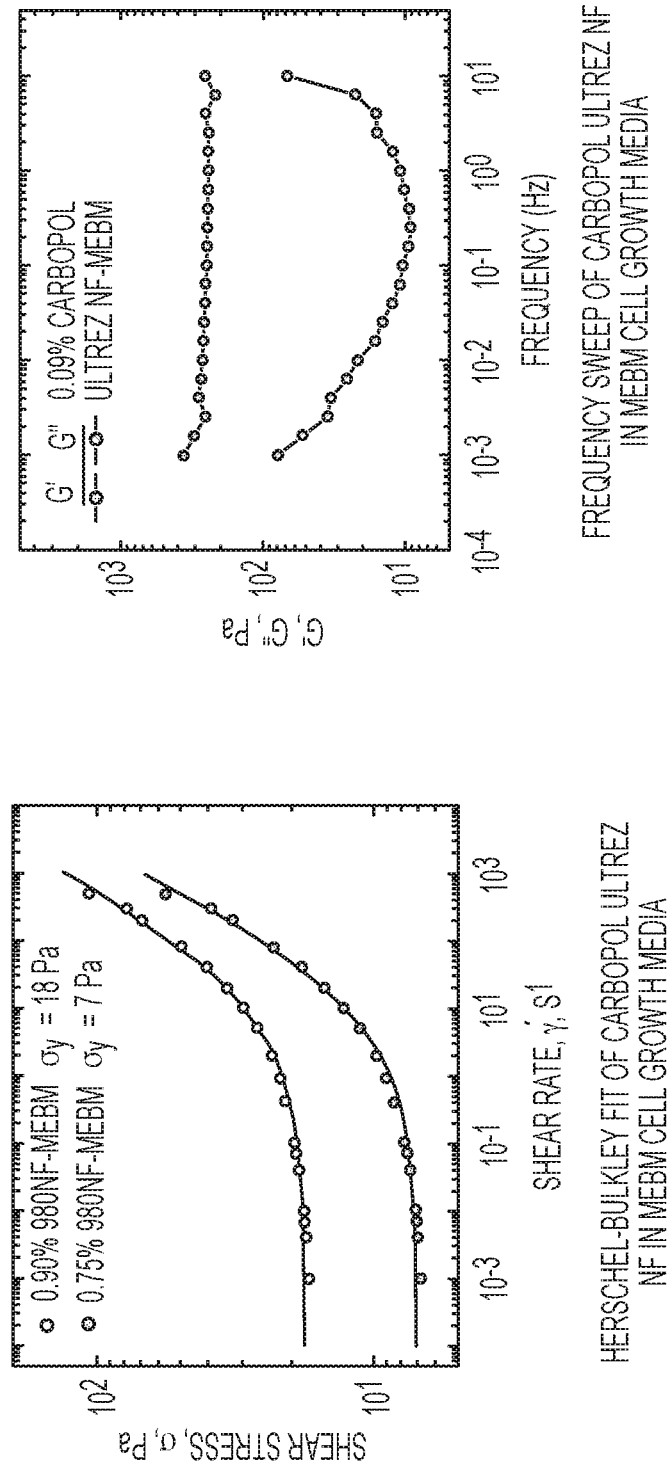

The inventors have recognized and appreciated that rapidly imaging a wound or other tissue cavity and printing a 3D tissue construct that will accurately fit the tissue cavity and may be added to the tissue cavity would be advantageous and may be particularly useful in rapid treatment of trauma. The inventors have in particular recognized and appreciated that a high speed and high precision way to replace tissue may be provided using 3D printing techniques described herein.

The inventors have recognized and appreciated that creating a 3D tissue construct using the 3D printing techniques described herein may provide soft tissue, which may be used to replace damaged (including missing) tissue, with higher precision and scale and at higher speed than previously possible. Such a tissue construct may also be made on-demand and to a custom specification. Such a tissue construct may also be made of biocompatible materials and/or of cells such that the tissue construct may merge with a portion of an organism, such as a person.

Described below are a variety of embodiments for printing tissue constructs for use with tissue cavities. In some such embodiments, the tissue construct may be constructed and arranged for insertion into a tissue cavity, based on information about the tissue cavity. For example, the tissue construct may be constructed (e.g., printed) as an aid in growing tissue to replace tissue that was previously disposed in a tissue cavity, which may be used in repairing the tissue cavity by returning the tissue cavity and surrounding tissue to a state prior to a removal of tissue that resulted in the tissue cavity. For example, once the tissue construct is inserted into the tissue cavity, the organism's tissues may grow into the tissue construct and fill the tissue cavity. In particular, as discussed in detail below, the tissue construct may include different biomaterials at different locations in the tissue construct that are adapted to encourage growth of particular tissues at those particular locations. The tissue construct may not, in some embodiments, include any tissues or cells when printed and/or when inserted into a tissue cavity, but may instead include, for example, one or more biomaterials that encourage tissue or cell growth. In other embodiments, however, the tissue construct may include cells and/or tissues that are deposited alongside biomaterials that encourage growth of the cells/tissues.

Embodiments may be used with tissue cavities of any suitable type. In some embodiments, for example, a tissue cavity may result from a wound. A wound may be an area of an organism from which tissue is damaged (including removed) intentionally and/or accidentally, and may result from any of a variety of causes. Such a wound may result from, for example, an accident that damages tissue, such as a workplace accident. Such a wound may additionally or alternatively result from an attack, such as an attack by an animal (including a human), parasite, or other organism that damages tissue. A tissue cavity may additionally or alternatively result from a disease or condition of an organism that damages the organism's tissues. Additionally or alternatively, a tissue cavity may result from a medical procedure, such as where a portion or an entirety of a wound results from a surgical procedure or a surgical procedure is performed to remove tissues from, for example, an existing wound, diseased tissues, and/or healthy tissues. Such a medical procedure may be performed on a wound following, for example, an accident or attack as part of healing the wound.

It should be appreciated that while the term "cavity" is used herein with respect to a tissue cavity with which tissue constructs may be used, embodiments are not limited to operating with any particular shape of tissue cavity. Rather, a cavity may be related to any tissue of an organism that is damaged, including missing. As such, a cavity is not required to have a concave shape. For example, a missing portion of a limb that is partially or entirely missing may be a tissue cavity.

In some examples below, the term "wound repair construct" may be used to refer to a tissue construct that has been printed to aid in replacing tissue of a tissue cavity of a wound. A wound repair construct may be a tissue construct printed to have a shape complementary to a shape of tissues surrounding a wound. Additionally or alternatively, a wound repair construct may be a tissue construct having biomaterials and/or cells disposed at specific locations corresponding to locations in the tissue cavity of tissues that were damaged (including removed) when the organism was wounded. It should be appreciated that embodiments are not limited to operating with any particular type of wound. Examples of wounds with which embodiments may operate include acute wounds, chronic wounds, large battlefield wounds, muscular skeletal wounds, or soft tissue wounds.

Printing techniques as described herein may support "printing" with multiple types of biomaterials in the same tissue construct, such that the tissue construct may merge with a portion of an organism with multiple types of tissue. For example, a deep wound might be repaired by a tissue construct that includes biomaterials compatible with multiple types of muscles. Further, printing techniques as described herein, by providing high precision, may enable printing of small passageways that support the formation of vasculature and microvasculature when the construct merges with the organism. As discussed in more detail below, in some embodiments 3D printing techniques are used to deposit biomaterial that is compatible with and/or encourages growth of specific types of tissues. In such embodiments, living tissues or cells may not be deposited in a construct during printing. Rather, once the biomaterial is printed in a tissue construct (e.g., in a wound repair construct) and the tissue construct is inserted into a tissue cavity, an organism's tissues may grow into the tissue construct to form tissue in the tissue cavity. Tissues/cells of certain types may grow at locations of biomaterial that encourages growth of tissues/cells of the types. However, as should be appreciated below, in other embodiments the tissue constructs may include one or more cells and/or tissues in addition to one or more biomaterials, or may include one or more tissues and/or cells and may not include biomaterials.

Thus, in some cases a tissue construct may include multiple types of biomaterials, and those types of biomaterials may be specifically positioned during a printing process. In the case that the tissue construct is to be used for wound repair, the types of biomaterials may correspond to positions of types of tissues that were included in the organism's tissue at the location of the tissue cavity before the organism was wounded. For example, where the organism before being wounded included bone tissues, soft muscle tissues, skin tissues, etc. at specific positions in tissue that was removed during the wounding, a wound repair construct may include biomaterial that is compatible with and/or encourages growth of bone tissues, soft muscle tissues, skin tissues, etc. deposited at corresponding locations in the wound repair construct. For example, the type of biomaterial that is compatible with and/or encourages growth of bone tissues may be deposited in the wound repair construct at a position corresponding to the location at which bone was located in the organism's tissue of the tissue cavity before the organism was wounded. In this way, the wound repair construct may aid in replacing the removed tissue when inserted into the tissue cavity.

Printing Biomaterials with Yield Stress Materials

The inventors have recognized and appreciated that by printing into a temporarily phase changed material (e.g., a thixotropic or "yield stress" material), a desired structure may be printed without having to print support material as well. Rather, the phase changed material may become the support material, by conforming to the printed volume and reverting to a phase that constrains the volume. The inventors have recognized and appreciated that this approach may decrease costs and manufacturing time as compared to conventional 3D printing systems, for which the surface tension between the printed material and the support material plays a key role in limiting the minimum feature size that can be printed. The printing may be achieved, for example, by injecting a second material into the phase changed material. The phase changed material may be temporarily created, for example, in a localized region of a yield stress material by energizing that region.

Accordingly, in some embodiments, one or more biomaterials are printed into yield stress materials. The biomaterial(s) that are printed in the tissue construct may include natural and/or synthetic polymer matrices compatible with implantation into an organism. Examples of yield stress materials into which the biomaterials may be deposited are described in this section, as well as techniques for printing into yield stress materials. The biomaterials, and the tissue construct, may be bioabsorbable or non-bioabsorbable. In some embodiments, one or more cells or types of cells may be printed into yield stress materials. In some such embodiments, the one or more cells or types of cells may be printed alongside one or more biomaterials. For example, a cell or type of cell may be printed alongside a biomaterial that is adapted to encourage growth of that cell or type of cell.

Soft granular gel made from polymeric micro-particles may be a desirable medium in which to write arbitrary 3D structures [1, 5, 57]. To illustrate the potential of 3D writing in a granular gel medium (GGM) we have produced a wide variety of structures including complex large aspect ratio 3D objects, thin closed shells, and hierarchically branched vessel networks. These structures may be made using a fine hollow tip that traces out spatial paths within a granular gel while injecting the desired material. It is the movement of the tip that may locally yield and fluidize the granular gel at the point of injection. The rapid solidification of the granular gel then may trap and hold the injected material behind the moving tip. Yielding and fluidization in granular matter may be called the jamming/unjamming transition [2, 58, 59, 60, 61, 62, 63, 64]. By trapping material within the jammed medium, the effects of surface tension, gravity, and particle diffusion can be negated, which enables the manufacturing of finely detailed delicate materials with nearly limitless aspect ratios. We have demonstrated the efficacy of this technique by making precise structures with a wide variety of materials including silicones, hydrogels, colloids, and living cells. Soft polymeric materials can be crosslinked into structures and removed from the GGM, while uncrosslinked particulate systems like colloids and cells can be left supported within the medium for seemingly infinite times. The precision and level of detail achieved by writing within a soft GGM may be limited by the size of the granules, which may be larger than 1 μm, which may be advantageous to eliminate colloidal-scale diffusion [65, 66, 67]. This approach can be immediately applied in a diversity of areas, rapidly contributing to the engineering of tissue and organs, flexible electronics, particle engineering, smart materials and encapsulation technologies.

One feature of 3D cell assemblies that may be grown using 3D tissue constructs described herein is the substrate in which the 3D tissue constructs are embedded when printed: yield stress materials. Structured 3D cell assemblies disposed in yield stress materials may enable study of tissue cell dynamics. The interplay of yield stress, interfacial tension, and cytoskeletal tension may generate new instabilities analogous to those of classical solids and fluids. Yield stress materials may be applied to these studies because (1) their properties allow for unprecedented versatility of cell assembly design, (2) they are homogeneous and transparent, enabling high quality imaging and tractable modeling, and (3) their use with cell assemblies represents the creation of a new class of biomaterial.

Mechanical instabilities in simple structures may be used to classify and measure collective cell forces. The hallmarks of instabilities reveal underlying forces, and to study instabilities is to study the interplay of dominating forces. For example, radial oscillations in fluid jets are the hallmark of the Rayleigh-Plateau instability; measuring these fluctuations probes the interplay of surface tension, viscous stress, and inertia. For cell-assemblies embedded in a support material, the emergent, dominating forces are not known. Simple cell structures may be created in yield stress materials, allowing for investigation of unstable behavior and the hallmarks of classic instabilities. The breadth of structures accessible with the methods described herein may be tested. Stresses may be measured optically by dispersing fluorescent markers in the yield stress material. The threshold of structure stability may be studied by tuning the yield stress of the embedding medium.

The symmetry and topology of complex multicellular structures may have a role in collective cell dynamics. Observations of cells in toroid structures have led us to a guiding discovery: topology can be used for load bearing. The inventors have investigated collective cell dynamics in single loop structures (topological genus=1), and in large arrays of loops (genus >1). The stability of loops depends on the yield stress of the material and cytoskeletal tension, which can be manipulated in many ways. Symmetry of loop arrays may control collective motion; if vorticity develops around each loop, even transiently, loop-loop interactions may arise. The inventors have looked for an anti-ferromagnetic phase in square vortex lattices; spin-glass phases may appear in hexagonal vortex lattices. Stability and correlation are compared between 1D, 2D, and 3D lattices.

In summary, yield stress materials have never been harnessed to create controlled, complex 3D cell structures. The first activities employing this new bio-material may uncover new kinds of mechanical instability arising from the combination of living, self-driven cells with a complex material that is studied elsewhere for its own exciting properties [1-6]. This unique combination enables the creation of large, multicellular lattices with which fundamental questions about the roles of symmetry and topology in collective cell behavior can be explored for the first time.

The current paradigm in cellular biomaterials research is to create a solid scaffold and demonstrate its biocompatibility in vitro or in vivo. The inventors have recognized and appreciated that properties of extant scaffold systems impede versatile experimentation of cell dynamics, limiting investigations of scaffold interactions with living cells. The characteristic shared by these scaffold systems: they are solid. Creating well controlled 3D cell assemblies of arbitrary design in solid scaffolds may not be possible. One question is how one can create a 3D cell manifold inside of a solid scaffold without damaging the scaffold. The inventors have recognized and appreciated that use of the yield stress cellular biomaterial is significant because it may (1) create a superior platform for carrying out fundamental investigations of 3D cell dynamics; (2) create a new class of biomaterial never before investigated; and (3) explore fundamental aspects of collective cell dynamics previously prohibited from study, limited by available support materials. These activities are founded on a new concept that breaks with the established paradigm in cellular biomaterials.

Yield stress materials may meet requirements of cellular biomaterials research, such as (1) control of cell aggregate size and shape; (2) measurement of cell generated force; and (3) optical imaging. Yield stress materials (YSMs) are solids when applied stress is below the yield stress, $\sigma_y$. At stresses exceeding $\sigma_y$, YSMs fluidize. When the applied stress falls below $\sigma_y$, a fluidized YSM solidifies again. These properties enable the generation of countless multi-cellular structures by extruding cells or cell/ECM mixtures into YSMs. As the cells are extruded, the nozzle fluidizes the YSM, and when the structure is complete, the extruding nozzle can be removed from the YSM, leaving behind homogeneous support material.

In some embodiments, a material injected into a temporarily phase changed material may be miscible with it. The inventors have recognized and appreciated that the minimum feature size that can be printed may be reduced by printing with such a miscible material. In cases where the printed material is immiscible with a supporting yield stress material, the competition between surface tension and yield stress may set a limit on printable feature size, comparable to that of traditional 3D printing where the Rayleigh-Plateau instability sets the minimum feature size. However, there may be no surface tension if the two materials are miscible, and the theoretical lower limit on printed feature size may be set by (a) the size of the microgel particles that constitute the yield stress material, (b) the size of the particles in the printed material, or (c) the size of the extrusion nozzle. Most "rapid prototyping" 3D printing systems use immiscible materials. The printed material is typically hydrophobic organic material, and the support material is typically water-soluble hydrophilic material. Thus, the minimum feature size of most commercially available 3D printers is limited by surface tension. The inventors have recognized and appreciated that printing particulate materials into particulate yield stress materials—both soluble in the same materials—may eliminate the surface tension limitation, which may side-step decades of technological challenges associated with surface wetting and interfacial energy. This improvement may be possible for "water-water" based printing, and "oil-oil" based printing; particulate aqueous suspensions can be printed into aqueous yield stress materials, and suspensions of oil-soluble particles can be printed into oil-based yield stress materials.

Yield stress materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Thus, yield stress materials may provide a self-healing, self-sealing support structure into which complex structures of arbitrary design can be printed. Many yield stress materials are particulate. For example, yield stress materials may include dense packs of microgels—microscopic particles made from a swollen crosslinked polymer network. Microgels can be made from aqueous, hydrophilic polymers or from hydrophobic polymers like PDMS.

Stress may be applied to such materials in any suitable way. For example, energy may be added to such materials to create a phase charge. The energy may be in any suitable form, including, mechanical, electrical, radiant or photonic, etc. The inventors have recognized and appreciated that substrates with complex geometry like tubes, toroids, spheres, cylinders, hierarchically branched vessel networks, high aspect ratio objects, and thin closed shells, may be challenging and time-consuming to fabricate with conventional methods, and that such substrates and structures with complex geometry may be printed more easily and more quickly using temporarily phase changed materials. Moreover, printing into a temporarily phase changed material may enable applications in which the printed structure does not solidify rapidly or at all, as it may not need to do so. The fluid may remain fluid forever because the temporarily phase changed material may hold the printed structure in place after printing or extrusion. By trapping the fluid or material within the temporarily phase changed materials, the effects of surface tension, gravity, and particle diffusion can be negated, which may enable the manufacturing of finely detailed delicate materials with nearly limitless aspect ratios. Moreover, the inventors have recognized and appreciated that structures can be "un-printed" using the same materials by reversing the path of the extrusion nozzle and reversing the flow direction.

The inventors have recognized and appreciated that a wide variety of materials may be used as temporarily phase changed materials, including silicones, hydrogels and colloidal particles, and living cells. Soft polymeric materials can be crosslinked into structures and removed from the temporarily phase changed material, while uncrosslinked particulate systems like colloids and cells can be left supported within the material for seemingly infinite times. The precision and level of detail achieved by writing within a temporarily phase changed material may be limited by the size of granules of the material, which may be made at micron and sub-micron sizes. This approach may aid in the development and manufacture of precise, hierarchical cell culture scaffolds, vascular networks, complex tissues, and, in some embodiments, entire organs.

The inventors have recognized and appreciated that, while most extant tissue printing techniques involve layer-by-layer deposition in a fluid bath with a solvent-casting method, in which the extruded material solidifies by the action of a compound in the bath (like alginate extruded into a calcium chloride bath), 3D printed tissues and/or biomaterials may be generated directly inside a "bath" of a nutrient medium with no intermediate solidification step or extracellular matrix using temporarily phase changed materials. In some embodiments, living tissue cells and/or biomaterials may be printed into arbitrary 3D structures, either with or without supplemental extracellular matrix material. The temporarily phase changed support material (e.g., yield stress material) may provide solidity, which may work without a "curing agent" to bolster the printed structure. Moreover, the inventors have recognized and appreciated that using temporarily phase changed materials may avoid the challenges of solvent-casting methods such as the nozzle frequently getting clogged as material solidifies before exiting the bath. Cell growth medium may be used as the solvent for aqueous microgels, making, for example, a tissue culture yield stress matrix. As an alternative example, cells can be printed into an oil-based yield stress material, using interfacial tension to maintain a well-defined surface.

The 3D printing techniques may be applied in any of multiple ways. Specifically, the inventors have recognized and appreciated significant demands for a 3D substrate of controllable, well-defined topology and material property that will aid deconstructing the complexity of cell interactions with 3D culture systems. The inventors have also recognized and appreciated that printing into a temporarily phase changed material may enable engineering of an artificial 3D in vitro environment, which may satisfy the growing interest in isolating specific environmental cues (e.g., substrate curvature) that a 3D culture could provide.

The inventors have recognized and appreciated that by printing particulate suspensions—like cells or any commonly used inks in 2D and 3D printing—into a particulate, temporarily phase changed material such as a particulate yield stress material, the printed structure can be miscible with the support structure without loss of printing precision. This miscibility without loss of precision is possible because the printed structure may be instantly trapped in the surrounding yield stress material as soon as it is extruded. In the case of miscible components, since there may be no surface tension between printed material and support material, the fundamental limit of most 3D printing strategies may be sidestepped. There may be no driving force for the printed features to "ball up." So, aqueous materials can be printed into aqueous supports, and oil-based materials can be printed into oil-based supports. These are in addition to any case of immiscible combinations, which may also be possible.

The inventors have recognized and appreciated that printing into a temporarily phase changed material may enable fabricating a 3D substrate or a cell encapsulating matrix of defined geometries. For example, yield stress materials may exhibit shear-thinning properties, characterized by viscosity reduction under stress and a return to their original solid-like state when stress is removed. This transient flow property may enable one to shape the material via simple shearing. According to some embodiments, the stress may be provided via an injector, such as a syringe needle, shearing across the yield stress material (referred to as the outer fluid) and the injection of an immiscible liquid (referred to as the inner fluid). The stress may yield a small region of the outer fluid, which may re-solidify when the motion of the needle halts and may trap a droplet of the inner liquid. Droplets of complex topology, e.g., toroidal or crescent-shaped droplets, can be generated by rotating the continuous phase around a central axis while extruding the inner liquid from an injection needle positioned slightly off-centered. The dimensions of the torus may be controlled by (1) varying the amount of liquid injected and (2) changing the position of the needle with respect to the center of rotation. Note when combined with horizontal movement of the needle, spiral-shaped droplets can also be made.

According to some embodiments, a 2D curved surface or surfaces may be fabricated with simultaneous cell seeding. Providing an oily yield stress fluid as the outer media and an aqueous dispersion of cells as the inner fluid, spherical or non-spherical droplets containing cells may be directly formed in a single-step process. Alternatively or additionally, 2D curved surfaces of tunable chemical and mechanical properties suitable for subsequent cell culture may be fabricated. In this case, the inner fluid may comprise common hydrogel or synthetic extracellular matrix materials (ECM) precursor solution. Solidification or gelation of the precursor solution may then be induced by ultraviolet (UV) or thermo-gelling processes, after which the solid may be isolated from the yield stress material and used as cell substrate.

According to some embodiments, a 3D cell encapsulation matrix of spherical or toroidal geometry may be fabricated. Cell entrapment technique may be used in conjunction with some embodiments simply by using a mixture of hydrogel precursor solution and cell dispersion as the inner fluid. Once polymerized via changes of physical or chemical conditions, depending on the materials of choice, the final structure may again be isolated from the outer yield stress material.

This intriguing behaviour at the transition may be leveraged to write sophisticated multi-dimensional structures in a soft GGM made from 7 μm diameter hydrogel particles. This medium may be fluidized under low shear stresses (1-200 Pa), permitting easy insertion and rapid motion of delicate needles deep within the bulk, but then rapidly re-solidifies in the wake to give a permanent and continuous medium that firmly holds the injected material in place (FIG. 10, FIGS. 30-34).

For ease of description herein, the terms "yield stress" and "yield stress material" are used but, unless indicated otherwise, should be understood to be a Herschel-Bulkley yield stress determined using the Herschel-Bulkley equation.

$$\sigma = \sigma_y + k\dot{\gamma}^p$$

where $\sigma_y$ is yield stress, $\sigma$ is shear stress, k is viscosity index of the material, $\dot{\gamma}$ is shear rate, and p is a positive number, and a material having such a yield stress.

In addition, unless indicated otherwise herein, a yield stress of a sample is determined by shearing the sample in a rheometer using plate-plate geometry and via the Herschel-Bulkley equation, via the following process. Prior to shearing, the rheometer tool surfaces may be roughened to prevent or mitigate slipping at the sample-tool interface. Using the rheometer, the sample is sheared at a variety of shear rates, extending from high shear rates (e.g., 1000 s$^{-1}$) to low shear rates (0.001 s$^{-1}$). For each shear rate, the sample is sheared for 30 seconds, after which shear stress data is collected and averaged. A series of shear stress measurements are collected sequentially for each shear rate. These shear rates are then used, via the Herschel-Bulkley equation, to determine (1) whether the material has a yield stress (i.e., a Herschel-Bulkley yield stress), and (2) the yield stress for the material. Those skilled in the art will appreciate that, for a material having a yield stress, a plot of shear stress versus shear rate will exhibit a plateau region at low shear rates, with the data points asymptotically approaching the material's yield stress at low shear rates. The yield stress is the shear stress at these low, near-zero shear rates, or an estimate of shear stress at zero strain rate determined using a low or near-zero shear rate, such as a shear rate of 10$^{-3}$ s$^{-1}$. As used herein (unless indicated otherwise), a "yield stress material" will be a material that has a yield stress determinable via this process. Those skilled in the art will appreciate that for a yield stress material (i.e., a Herschel-Bulkley yield stress material) at low shear (e.g., a near-zero shear rate), a shear stress is independent of shear rate and instead exhibits only a shear stress dependent only on an elastic component of the material.

To illustrate such behavior, FIG. 1 (includes FIGS. 1A-1G) includes 8 graphs of shear stress versus shear rate, for different types of yield stress materials, including examples of carbomer polymers in various concentrations and immersed in various solvents. The curves show Herschel-Bulkley behavior (a plateau region) and thus correspond to materials having a yield stress. As should be appreciated from the graph of FIG. 1A, the 0.05% Carbopol® in a water/NaOH solvent is nearly not a yield stress material, in that the data points barely exhibit a plateau region at low shear rate. This demonstrates that some microgels (including hydrogels) in solvents, based on other factors such as solvent or concentration, may not be yield stress materials having a yield stress (i.e., a Herschel-Bulkley yield stress).

For the tests resulting in the data of FIG. 1, various forms of Carbopol® in various concentrations or a silicone elastomer dispersion were swollen in water and NaOH (at pH 6) or swollen in cell growth media (at pH 7.4), as noted in the figure. The cell growth media used was MEBM media including 10% fetal bovine serum and 1% penicillin-streptomycin. As should be appreciated at least from FIG. 1A, the yield stress of the Carbopol® in cell growth media decreases with lower concentration. This is because the Carbopol® particles reduce in size in high-salt environments. The examples of FIG. 1 demonstrate the ability of Carbopol® and other hydrogels (e.g., other carbomer polymers or silicone elastomer dispersions) to be "tuned" to have desired yield stresses for a given application, by varying factors such as concentration and solvent.

The graphs of FIG. 1 also include graphs of shear moduli versus frequency for each of the materials for which a shear stress vs. shear rate plot is provided. The graphs of shear moduli versus frequency demonstrate material properties of the yield stress materials; specifically, that the yield stress materials act as solids under the applied strain. To produce the data, frequency sweeps at low applied strains were performed. As shown in the graphs, the yield stress materials all exhibit fairly flat responses, with G' and G" remaining separated across the spectrum. The yield stress materials thus behave similarly to a Kelvin-Voigt linear solid with damping.

As should be appreciated from the discussion below, yield stress materials (i.e., materials having a Herschel-Bulkley yield stress) may be desirably used in a 3D printer in embodiments, as a support material during printing. As will be appreciated from the discussion below of specific yield stress materials, the inventors have recognized and appreciated the desirability, for use as support materials during 3D printing, of yield stress materials having yield stresses in a range of 1 Pascal to 1000 Pascals, and advantageously in a range of 1 to 100 Pascals or 10 to 100 Pascals. For example, embodiments are described below in which carbomer polymers (such as Carbopol®) having yield stresses between 1 and 100 Pascals are used in 3D printing. Some embodiments may operate with yield stress materials having any yield stress below 100 Pascals, with a minimum yield stress only being defined by the lower physical limit on Herschel-Bulkley yield stresses.

Separately, the inventors have recognized and appreciated the desirability of yield stress materials having a yield stress within these same ranges of 1 to 100 Pascals or 10 to 100 Pascals that are discussed below. The inventors have recognized and appreciated that, during 3D printing in a yield stress material, motion of a printing nozzle within a bath of yield stress material may create undesired (and undesirable) "crevasses" in the material. Printing in a bath of yield stress material without spontaneous formation of undesired crevasses may be avoided by using a yield stress material with a low yield stress, such as a material (like the Carbopol® materials described below) having a yield stress below 100 Pascals. For yield stress materials that are hydrogels, an upper limit on yield stress is the hydrogel's hydrostatic pressure, determined by $\rho \cdot g \cdot h$, where p is the density of the yield stress material, g is the acceleration due to gravity, and h is a depth of printing below the surface. For some embodiments in which living cells are being 3D printed in petri dishes and/or well plates containing a hydrogel (such as Carbopol®), the cells may be printed at a depth up to 1 cm. In such embodiments, the upper limit on yield stress (as determined from the hydrostatic pressure) is approximately 100 Pascals. Desirable hydrogel materials (including Carbopol® materials) having yield stresses up to 100 or 1000 Pascals are discussed in detail below.

Those skilled in the art that materials having a yield stress will have certain thixotropic properties, such as a thixotropic time and a thixotropic index.

As used herein, a thixotropic time is a time for shear stress to plateau following removal of a source of shear. The inventors recognize that thixotropic time may be measured in different ways. As used herein, unless indicated otherwise, thixotropic time is determined by applying to a material, for several seconds, a stress equal to 10 times the yield stress of the material, followed by dropping the stress to 0.1 times the yield stress. The amount of time for the shear rate to plateau following dropping of the stress is the thixotropic time.

As used herein, a thixotropic index (for a yield stress material) is defined as the ratio of viscosity at a strain-rate of $2\ s^{-1}$ to viscosity at a strain-rate of $20\ s^{-1}$.

Figure 2:
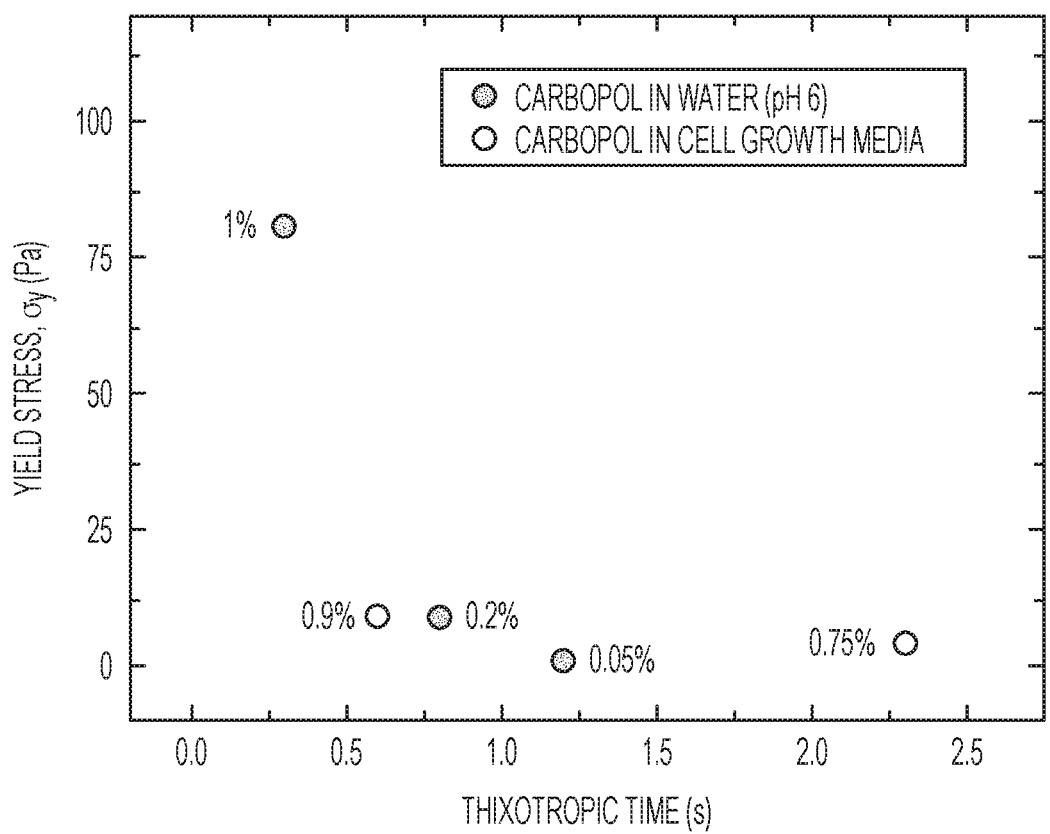
FIG. 2 is a plot of yield stress versus thixotropic time for some yield stress materials with which some embodiments may act and, for comparison, other materials that are not yield stress materials.

Yield stress materials with desirable yield stresses may also have desirable thixotropic properties, such as desirable thixotropic indexes or thixotropic times. For example, desirable yield stress materials (including hydrogel materials having a yield stress below 100 Pascals, some of which are described in detail below, such as Carbopol® materials) may have thixotropic times less than 2.5 seconds, less than 1.5 seconds, less than 1 second, or less than 0.5 seconds, and greater than 0.25 seconds or greater than 0.1 seconds. FIG. 2 is a plot of yield stress (as given by zero-shear rate stress estimate) versus thixotropic time for a variety of materials, including hydrogel solutions like the Carbopol® solutions in some of the solvents and concentrations shown in FIG. 1 and discussed in detail below. The Carbopol® solutions exhibit a yield stress below 100 Pascals (and many below 25 Pascals), as well as low thixotropic times. The thixotropic times of the Carbopol® solutions having a yield stress below 100 Pascals is less than 2.5, less than 1.5 seconds, less than 1 second, or less than 0.5 seconds, and greater than 0.25 seconds or greater than 0.1 seconds.

Figure 3:
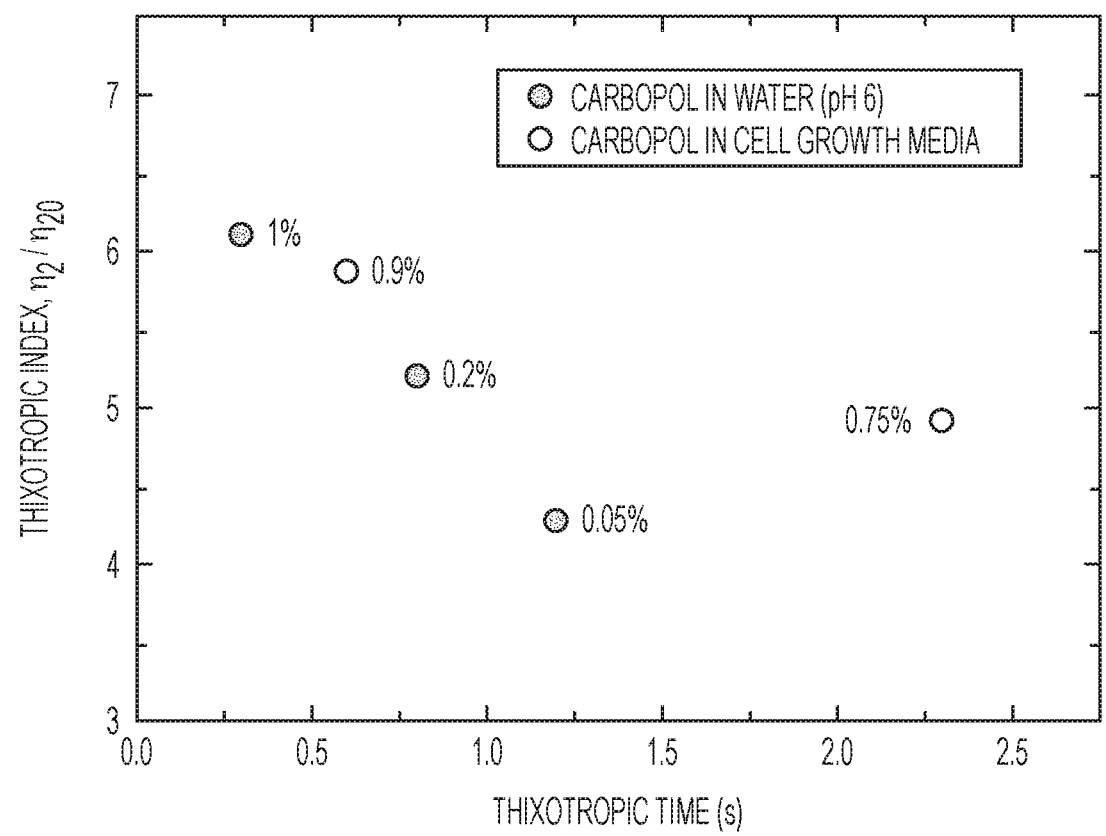
FIG. 3 is a plot of thixotropic index versus thixotropic time for some yield stress materials with which some embodiments may act and, for comparison, other materials that are not yield stress materials.

Similarly, FIG. 3 shows a plot of thixotropic index to thixotropic times, for the same solutions illustrated in FIG. 2. For hydrogel yield stress materials with a yield stress below 100 Pascals (including those discussed in detail below, like Carbopol® solutions), the thixotropic index is less than 7, less than 6.5, or less than 5, and greater than 4, or greater than 2, or greater than 1.

Desirable yield stress materials, like hydrogels such as the Carbopol® solutions described below, may thus have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

Because of the yield stress behavior of yield stress materials, materials deposited into a yield stress material (such as through 3D printing techniques described herein) may remain fixed in place in the yield stress material, without the yield stress material or the deposited material needing to be cured or otherwise treated to reverse a phase change (e.g., by heating to cross-link, following printing). Rather, the yield stress materials permit an indefinite working time on deposition of materials inside yield stress materials, including printing of objects within yield stress materials. For example, in experiments described in detail below, printed objects stayed in place for multiple months (i.e., greater than one minute, greater than one hour, greater than one day, greater than one week, and greater than one month) without movement following deposition, without curing or cross-linking of the yield stress material or the deposited material, or otherwise without treatment. This may permit continuous printing/deposition of a material within a yield stress support material for greater than one minute, greater than one hour, greater than one day, greater than one week, or greater than one month, or anywhere in a range from one minute to one month, where continuous printing would not include ceasing for reasons related to the chemistry of the support or printed material (e.g., treating or curing) but may include ceasing for reasons related to mechanics of printing (e.g., reloading of materials to be printed or movement of print head to a different location).

As should be appreciated from the foregoing, according to some embodiments, a yield stress material that may serve as a 3D construct-encapsulating matrix or scaffold may include one or more hydrogels. Some such hydrogels may be bio-compatible polymers. The hydrogels may be dispersed in solutions (e.g., solutions with cell growth medium) in various concentrations. One example of a concentration is below 2% by weight. Another concentration example is approximately 0.5% to 1% hydrogel particles by weight, and another is approximately 0.2% to about 0.7% by mass. Those skilled in the art will appreciate that other concentrations may be used. Those skilled in the art will further appreciate that, when disposed in a solution as discussed herein, hydrogel particles will swell with the solvent and may form a granular gel material, as discussed elsewhere herein. Such a granular gel may include swollen hydrogel particles having a characteristic size at a micron or submicron scale. For example, in some embodiments, a swollen hydrogel particle may have a size between about 0.1 µm and 100 µm, including 5 µm as discussed above.

An example of a hydrogel with which some embodiments may operate is a carbomer polymer, such as Carbopol®. Carbomer polymers may be polyelectrolytic, and may comprise deformable microgel particles.

Carbomer polymers are particulate, high-molecular-weight crosslinked polymers of acrylic acid with molecular weights of up to 3-4 billion Daltons. Carbomer polymers may also comprise co-polymers of acrylic acid and other aqueous monomers and polymers such as poly-ethylene-glycol.

While acrylic acid is the most common primary monomer used to form polyacrylic acid the term is not limited thereto but includes generally all α-β unsaturated monomers with carboxylic pendant groups or anhydrides of dicarboxylic acids and processing aids as described in U.S. Pat. No. 5,349,030. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2,340,111; and 2,533,635. The disclosures of all of these U.S. Patents are hereby incorporated herein by reference for their discussion of carboxylic polymers and copolymers that, when used in polyacrylic acids, form yield stress materials as otherwise disclosed herein. Specific types of cross-linked polyacrylic acids include carbomer homopolymer, carbomer copolymer and carbomer interpolymer monographs in the U.S. Pharmocopia 23 NR 18, and Carbomer and C10-30 alkylacrylate crosspolymer, acrylates crosspolymers as described in PCPC International Cosmetic Ingredient Dictionary & Handbook, 12th Edition (2008).

Carbomer polymer dispersions are acidic with a pH of approximately 3. When neutralized to a pH of 6-10, the particles swell dramatically. The addition of salts to swelled Carbomer can reduce the particle size and strongly influence their rheological properties. Swelled Carbomers are nearly refractive index matched to solvents like water and ethanol, making them optically clear. The original synthetic powdered Carbomer was trademarked as Carbopol® and commercialized in 1958 by BF Goodrich (now known as Lubrizol), though Carbomers are commercially available in a multitude of different formulations.

Figure 4:
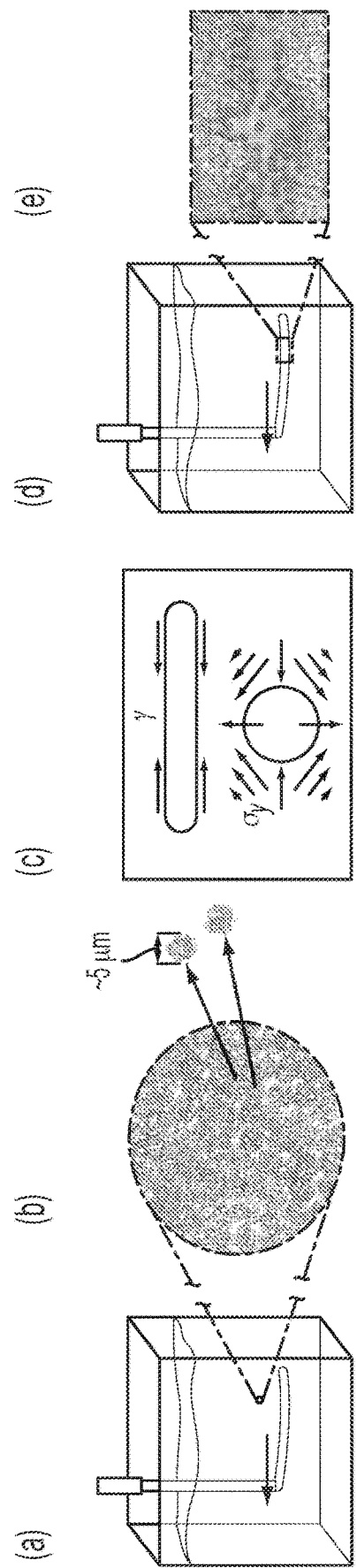
FIG. 4 illustrates cell structures extruded into yield stress materials for exemplary experimental study according to some embodiments.

Hydrogels may include packed microgels—microscopic gel particles, ~5 µm in diameter, made from crosslinked polymer (FIG. 4). The yield stress of Carbopol® is controlled by water content. Carbopol® yield stress can be varied between roughly 1-1000 Pa [41]. Thus, both materials can be tuned to span the stress levels that cells typically generate. As discussed above, while materials may have yield stresses in a range of 1-1000 Pa, in some embodiments it may be advantageous to use yield stress materials having yield stresses in a range of 1-100 Pa or 10-100 Pa. In addition, some such materials may have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

In some embodiments, silicone elastomer dispersions may also serve as yield stress materials with which some embodiments may operate. Examples of suitable silicone elastomer dispersions may include dimethicone/vinyl dimethicone crosspolymer blends from Dow Corning Corporation (Midland, Mich.) under trade name Dow Corning® 9040 silicone elastomer (cyclopentasiloxane and dimethicone crosspolymer), DC-9041 (dimethicone and dimethicone crosspolymer), EL-9140DM (dimethicone and dimethicone crosspolymer); SFE 839, a cyclopentasiloxane (and) dimethicone/vinyl dimethicone crosspolymer from Momentive Performance Materials Inc. (Waterford, N.Y.); cyclopentasiloxane (and) cetearyl dimethicone/vinyl dimethicone crosspolymer from Momentive Performance Materials Inc. under the tradename Silsoft* Silicone Gel; KSG-15 (cyclopentasiloxane and dimethicone/vinyl dimethicone crosspolymer), KSG-16 (dimethicone and dimethicone/vinyl dimethicone crosspolymer), KSG-18 (phenyl trimethicone and dimethicone/phenyl vinyl dimethicone crosspolymer), and KSG-41 (mineral oil and vinyl dimethicone/lauryl dimethicone crosspolymer) from Shin Etsu Silicones (Akron, Ohio).

Figure 5:
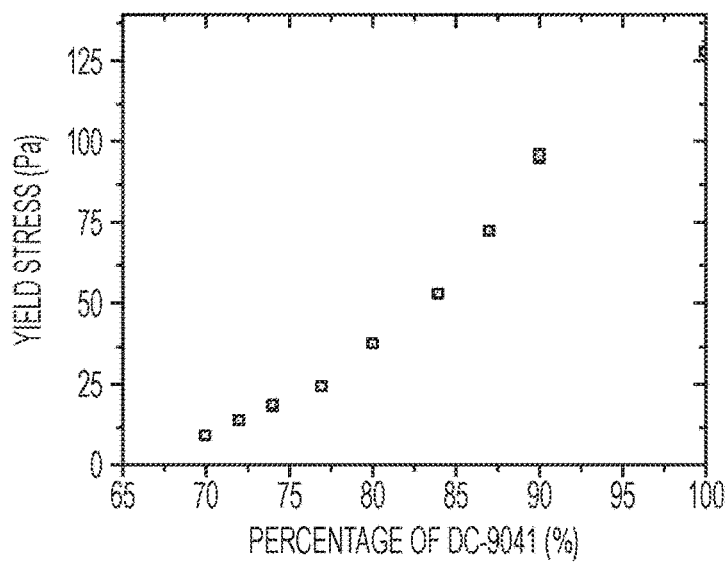
FIG. 5 is a chart of the yield stress of silicone fluid as a function of neat material concentration (with 10 cst silicone oil as solvent) according to some embodiments.

An elastomer dispersion may provide a transparent, stable viscous gel, or paste-like material typically described as thixotropic solid. The yield stress of the gels can be conveniently tuned by varying dispersion concentration, as exemplarily shown using DC-9041 with low viscosity silicone oil in FIG. 5. The common solvent in the pre-made dispersion may be a low molecular weight silicone. Other types of organic solvents can also swell the silicone elastomer, and therefore a mixture of solvents may be used.

Figure 6:
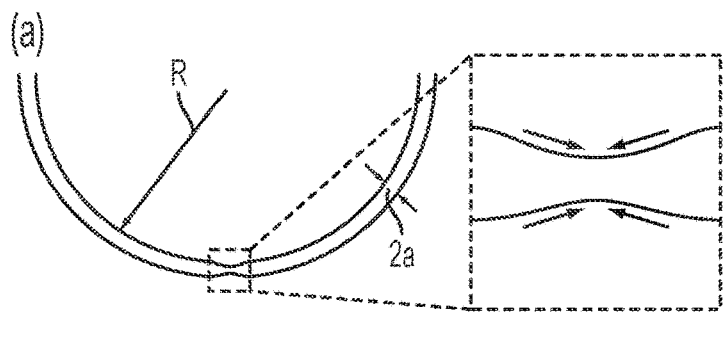
FIG. 6 illustrates (a) a schematic of the top view of an unstable torus and (b) and an example of the smallest length scale ($a_c$) achievable using silicone material of different yield stress according to some embodiments.
Figure 6:
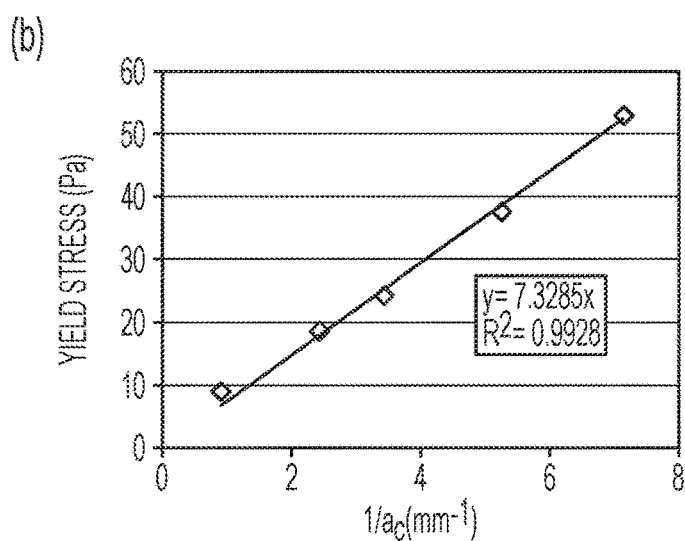
Figure 7:
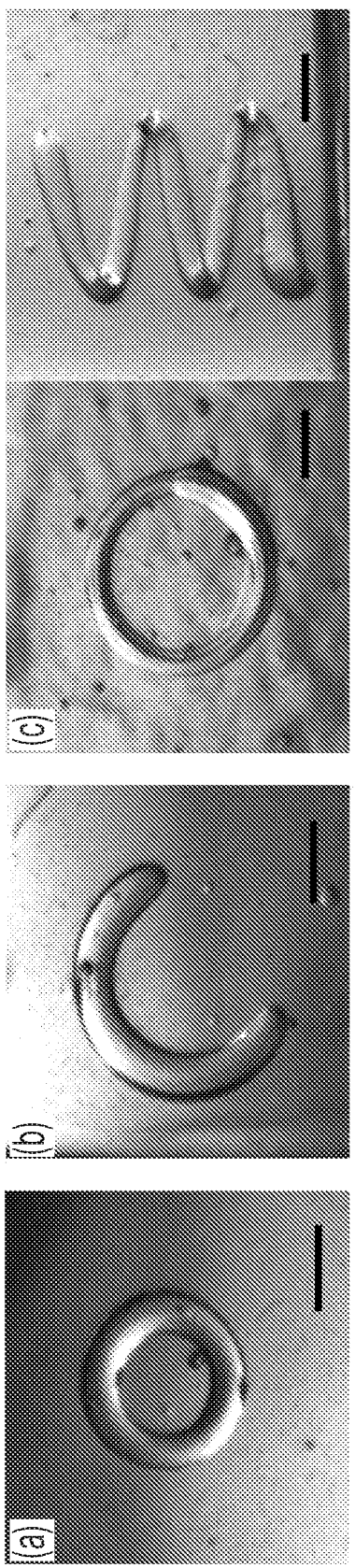
FIG. 7 illustrates structures that may be formed using techniques as described herein, including (a) toroidal, (b) crescent-shaped, and (c) spiral-shaped (left: top view; right: side view) droplets according to some embodiments. Scale bars may represent 1 millimeter.

As discussed above, in some embodiments, the resolution, i.e., the smallest dimension, of 3D structures printed using techniques described herein may be determined by the yield stress of the yield stress materials as well as the interfacial tension between the inner and outer fluids. For a pair of fluids, with outer fluid yield-stress $\tau_y$ and interfacial tension $\gamma$, the relationship between the minimum (pattern) feature size and these fluid properties may be described as follows: Liquid jets inside a yield stress material may experience surface tension driven stresses, similar to that in Newtonian liquid, where minimization of interfacial area may be preferred and may eventually lead to the breakup of jets into spherical droplets. When the yield stress of the outer fluid is greater than the surface stress ($\tau_y > \gamma/a$, a being the radius of the liquid jet), as shown in FIG. 6, the jet geometry may be stable and the breakup may not occur. Hence, resolution improvement may be achieved by either increasing $\tau_y$ and/or reducing $\gamma$. The shortest distance between neighboring tubes (inner circle diameter in the case for a torus) and the thinnest dimension of the tube (tube diameter) may usually be on the order of a hundred microns. FIG. 7 shows some examples of the different geometries that can be produced.

According to some embodiments, a blend of silicone elastomer and compatible solvent may be used directly as a cell-friendly matrix. The silicone blend of varying yield-stress may be used to form a matrix having controlled geometry and interfacial curvature for cell culturing. Droplets of cell dispersion may be contained inside the silicone elastomer, which may allow cells to disperse freely in the carrier fluid (culture media) and eventually sediment at the liquid-silicone interface. Once at the interface, cells may be able to explore regions of varying surface curvature and respond to it. Further components may be added to the carrier fluid to render the silicone surface bioactive—for example, extracellular matrix proteins (collagen or other adhesive proteins), antibodies, or drugs.

Figure 8:
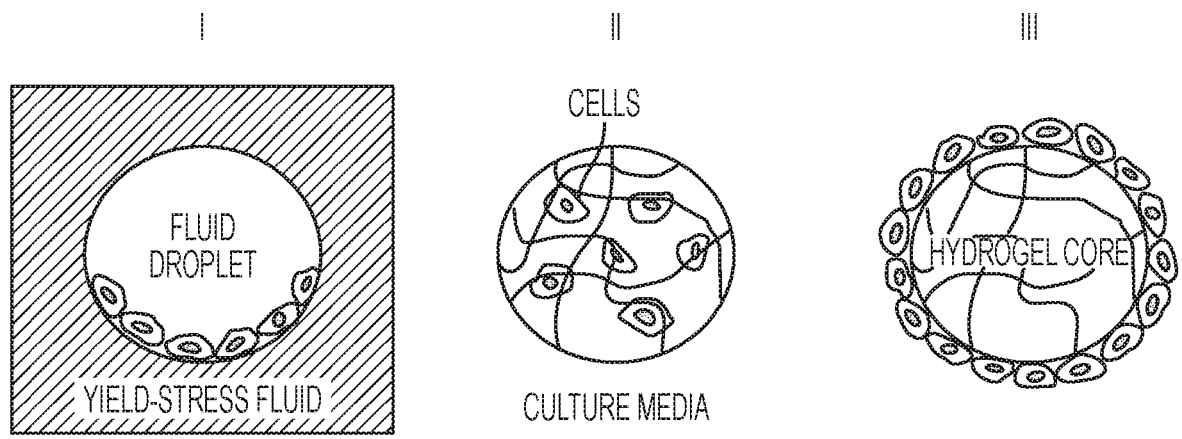
FIG. 8 illustrates schematics of three variations of a cell-matrix configuration that may be formed using techniques as described herein according to some embodiments.

According to some embodiments, the cells may be introduced during or after matrix formation, which may yield three distinctive types of cell assemblies, as shown in FIG. 8. According to some embodiments, a quick and simple, surfactant-free encapsulation may be provided. As described above, the inventors have recognized and appreciated the varied topology of structures that can be generated, including toroidal surfaces presenting regions of positive Gaussian curvature (as in spheres), regions of zero Gaussian curvature (as in 2D planes), and regions of negative Gaussian curvature (like those of a saddle). Alternatively or additionally, the mechanosensing of substrate curvature by cells may be determined. This determination may include fabrication of scaffolds with controlled geometries made of a selected matrix material, seeding cells on these substrates with different curvatures, and evaluating responses produced by the cells growing in contact with different substrates.

Exemplary Implementation of a 3D Printing System

Figure 9:
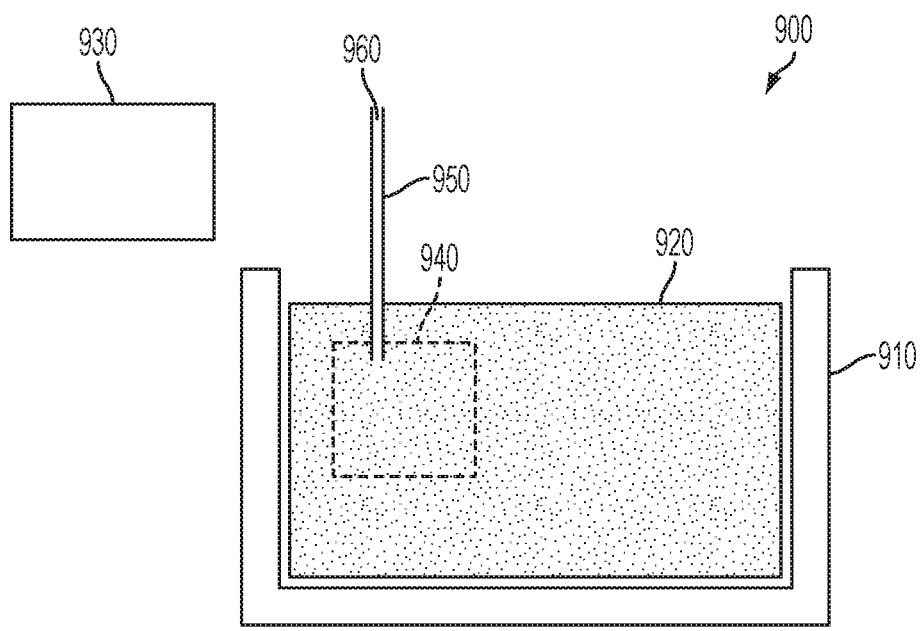
FIG. 9 is a diagram illustrating an apparatus for three-dimensionally printing according to some embodiments.

FIG. 9 illustrates an exemplary apparatus 900 for creating a three-dimensional structure, with which some embodiments may operate. For example, in some embodiments, some or all components of the apparatus 900 may be implemented as a portion or an entirety of an injector of the apparatus 1300 of FIG. 13 for printing a tissue construct for use with, for example, wound repair.

The apparatus 900 of FIG. 9 may include a container 910, a focused energy source 930, and an injector 950. The container 910 may hold a first material 920. The focused energy source 930 may cause a phase change in a region 940 of the first material 920 by applying focused energy to the region 940. The injector 950 may displace the first material 920 with a second material 960.

According to some embodiments, the container 910 may be a tub, a bowl, a box, or any other suitable container for the first material 920. The container 910 may be configured to release the first material 920. For example, the container 910 may include a resealable and/or hinged opening that may be opened when printing of the second material 960 is completed, so that the first material 920 may be removed from around the second material 960. Alternatively or additionally, the first material 920 may be washed away in whole or in part, such as by introducing organic solvents and/or increasing an electrolyte concentration of the first material. The electrolyte concentration may be increased by introducing one or more salts to the first material or otherwise increasing a concentration of one or more salts in the first material. Salts that may be used include monovalent salts or low-levels of multivalent salts. Sodium chloride, potassium chloride, or calcium chloride may be used, or salts of ammonia. The apparatus 900 may include a second injector (not illustrated in FIG. 9) for depositing one or more salts and/or organic solvents to wash away the first material, or to otherwise increase an electrolyte concentration of the first material to wash away the first material.

The first material 920 may include a thixotropic or yield stress material, or any material suitable for temporary phase changing. In some examples, the thixotropic or yield stress material may include a soft granular gel. The soft granular gel may be made from polymeric packed micro-particles. The polymeric packed micro-particles may be about 5 micrometers in diameter.

Figure 10:
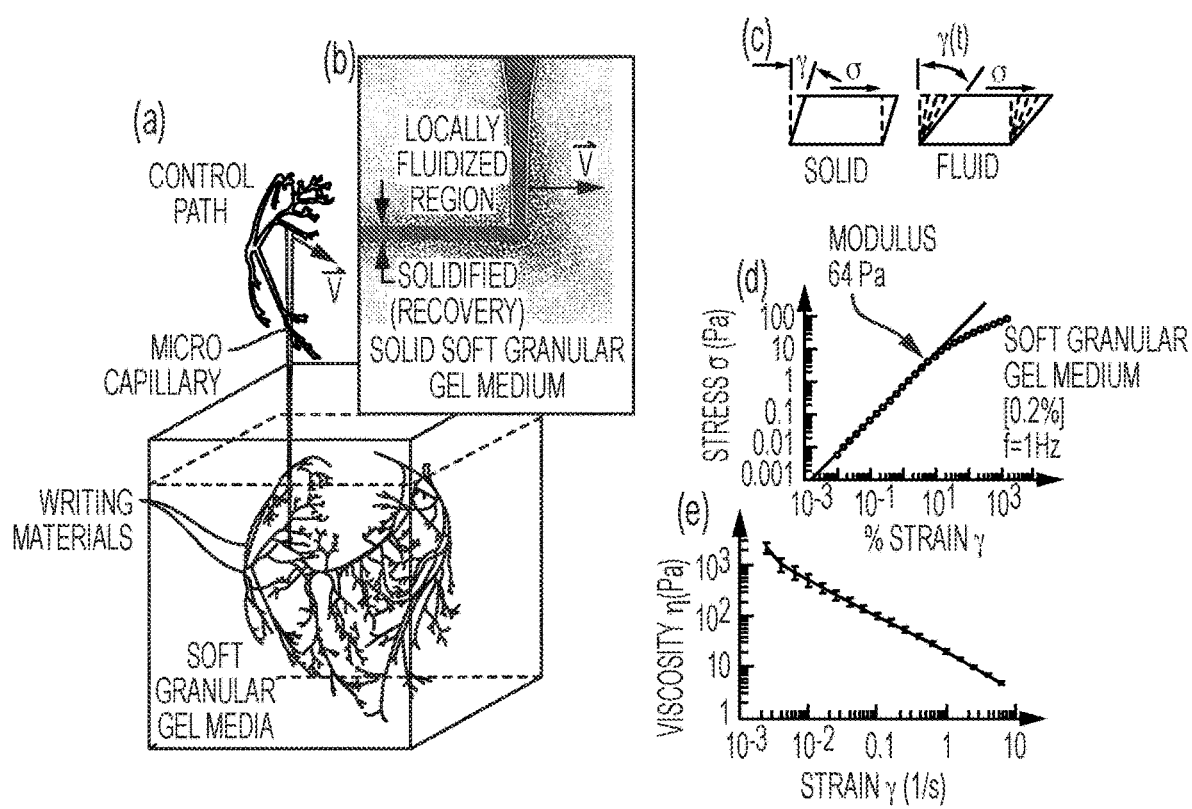
FIG. 10 schematically illustrates printing in a cartridge containing a granular gel as a 3D drawing medium.

FIG. 10 schematically illustrates printing in a cartridge containing a granular gel as a 3D drawing medium: a) A microscale capillary tip sweeps out a complex pattern as material is injected into the granular gel medium. Flow rate, Q, and tip-speed in all three directions may determine the girth of the drawn feature. Complex objects can be generated because the drawn structure does not need to solidify or generate support on its own. b) As the tip moves, the GGM locally fluidizes then rapidly solidifies, leaving a drawn cylinder in its wake. The reversible transition allows the tip to traverse the same regions repeatedly. c) The soft GGM may be a yield stress material, which elasticically deforms at low shear strains and fluidizes at high strains. d,e) Stress-strain measurements reveal a shear modulus of 64 Pa and yield stress of 15 Pa for 0.2% (w/v) GGM, and a strain-rate sweep at high strain (100%) shows shear thinning.

According to some embodiments, the focused energy that causes a phase change in the first material 920 may include mechanical energy, such as kinetic energy due to displacement of the injector 950 relative to the first material 920. In this example, the focused energy source 930 may include the injector 950. According to some embodiments, the injector 950 may include a fine hollow tip, which may carefully trace out spatial paths within the first material 920 (e.g., a granular gel) while injecting the second material 960. The movement of the tip may locally yield and fluidize the first material 920 at the point of injection (i.e., in the region 940). Another example of mechanical energy may include ultrasonic pressure waves. Alternatively or additionally, the focused energy may include radiant energy, such as radio frequency radiation, which may be directed into the region 940.

According to some embodiments, the first material and the second material may be miscible with each other. Alternatively, the first material and the second material may be immiscible with each other. According to some embodiments, the second material may comprise extracellular matrix materials precursor solution, or one or more biomaterials or types of biomaterials discussed herein. Alternatively or additionally, the second material may comprise one or more cells. In some embodiments that inject both biomaterials and cells, the injector 950 may include two injectors: one to inject biomaterial and one to inject cells. Additionally, where multiple types of biomaterials and/or multiple types of cells are to be injected, there may in some embodiments be multiple injectors, such as an injector to print some types of biomaterials and another injector to print other types of biomaterials, and/or an injector to print some types of cells and another injector to print other types of cells. Embodiments are not limited to working with any particular number or arrangement of injectors.

According to some embodiments, the focused energy source 930 may cause a reverse phase change in the region 940 of the first material 920. For example, a reverse phase change may be used to "heal" and solidify the first material 920 around the second material 960, trapping and permanently embedding the second material 960 in the wake of the injector 950. Alternatively or additionally, a reverse phase change may be used to remove the second material 960 from within the first material 920.

Figure 11:
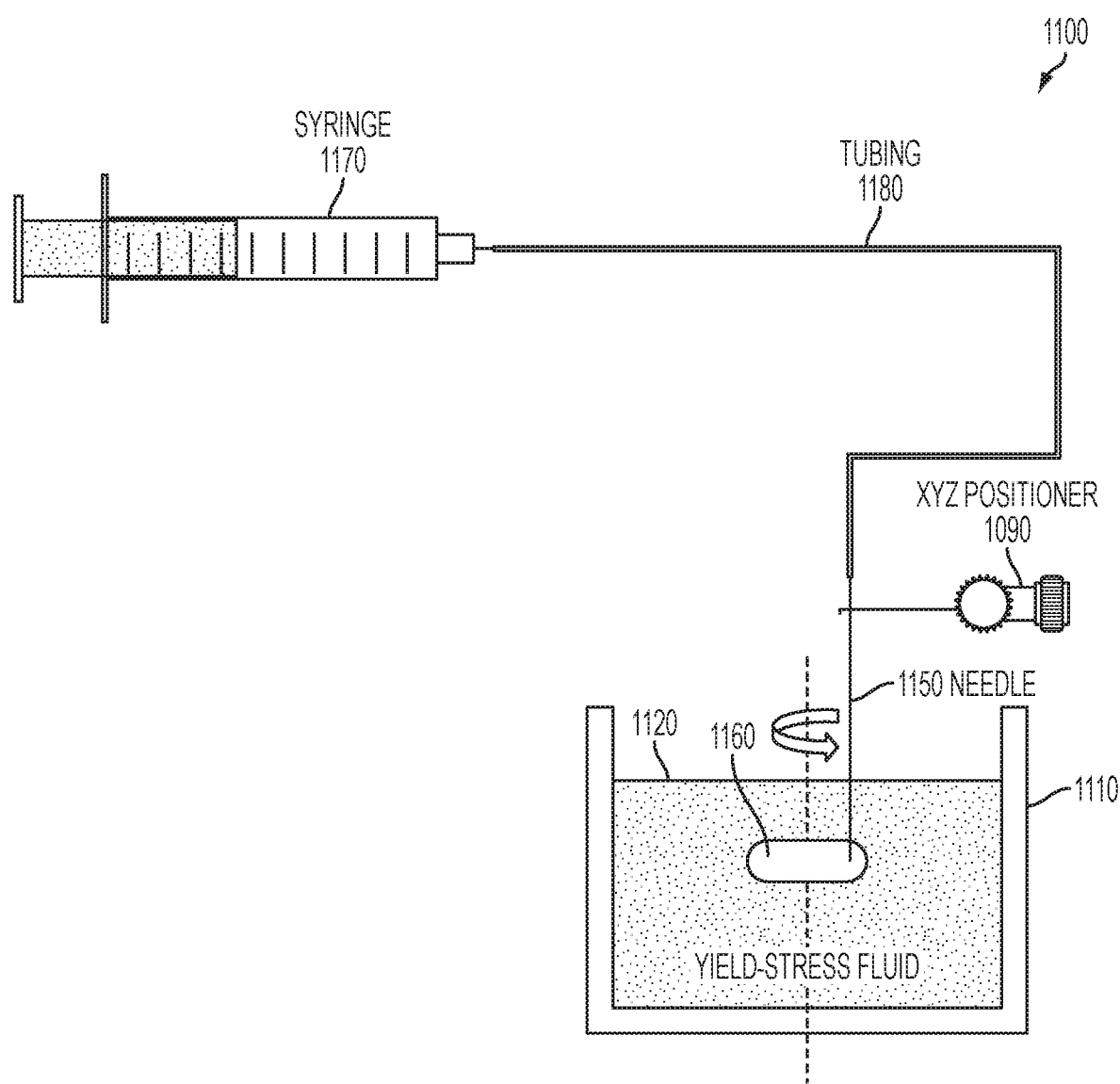
FIG. 11 is a schematic of a device for three-dimensionally printing according to some embodiments.

According to some embodiments, droplets of non-spherical geometries may be prepared by injecting an aqueous inner liquid into a rotating bath of non-polar yield stress material, as shown schematically in FIG. 11. FIG. 11 illustrates an apparatus 1100 for three-dimensionally printing. The apparatus 1100 may include a housing or container 1110, a needle 1150, a syringe 1170, and tubing 1180. The housing 1110 may hold a first material 1120. The needle 1150 may displace the first material 1120 with a second material 1160. The tubing 1180 may be connected to an output of the syringe 1170 and an input of the needle 1150. The syringe 1170 may include an amount of the second material 1160, which it may inject via the tubing 1180 and the needle 1150 into the first material 1120 from a container or other source of the second material.

According to some embodiments, the apparatus 1100 may include a platform (not shown) that may cause relative displacement between the first material 1120 and the needle 1150. Additionally, the relative displacement between the first material 1120 and the needle 1150 may comprise relative rotation between the first material 1120 and the needle 1150, as shown in FIG. 11. This relative rotation between the first material 1120 and the needle 1150 may comprise rotation about an axis of the first material 1120, also shown in FIG. 11. According to some embodiments, the platform may cause the relative displacement between the cartridge 1110 and the needle 1150 at a displacement rate faster than a characteristic breakup time of a jet of the second material 1160.

According to some embodiments, the apparatus 1100 may further include a positioner or actuator 1190. The positioner 1190 may cause relative displacement between the needle 1150 and the first material 1120. For example, the positioner 1190 may position the needle 1150 three-dimensionally so that the second material 1160 enters the first material 1120 at the desired locations. The positioner 1190 may also be used in conjunction with the platform to create specific shapes as the platform and positioner 1190 each cause displacement simultaneously. For example, the platform may cause relative rotation between the first material 1120 and the needle 1150 while the positioner 1190 may displace the needle 1150 up and down, side to side, back and forth, and so on, creating any shape desired. Alternatively or additionally, the motion of the needle 1150 may be synchronized with the motion of the positioner 1190.

According to some embodiments, during fluid infusion, a liquid jet may be stretched by the continuous rotating motion of the outer fluid, similar to that of liquid co-flow. The principle of forming an enclosed curved jet (or toroidal droplet) inside a yield stress outer fluid may be similar to that of forming such droplets in simple Newtonian liquids (E. Priam et al. (2009), Generation and stability of toroidal droplets in a viscous liquid, Phys. Rev. Lett. 102, 234501): to perform a full rotation faster than the characteristic breakup time of the liquid jet. The temporarily phase changed portion or region of the first material 1120, which may effectively be "solidified" under static conditions, may allow further stabilizing of the non-spherical geometry. For example, yield stress material may be immiscible with the inner fluid, preferably biocompatible, and may provide optical clarity as well as tunable mechanical properties.

According to some embodiments, the first material 1120 and the second material 1160 may allow the apparatus 1100 to function without any need of additional materials, such as a filler material or fluid for filling in crevasses created during printing. Additionally, the first material 1120 need not be photocrosslinkable material; rather, the first material 1120 may be photocrosslinkable or unphotocrosslinkable.

According to some embodiments, the second material 1160 need not be a yield stress material for use as the "ink" for printing; rather, any suitable material may be used for the second material 1160. Additionally, the first material 1120 may have any suitable modulus, which is not limited to a "high" modulus. For example, as discussed above, the modulus of the first material 1120 may be anywhere in the range of 100 to 10,000 Pascals, or it may be outside this range. The yield stress of the first material 1120 may vary, depending on the desired consistency, but may generally be in the range of 10-100 pascals.

Figure 12A:
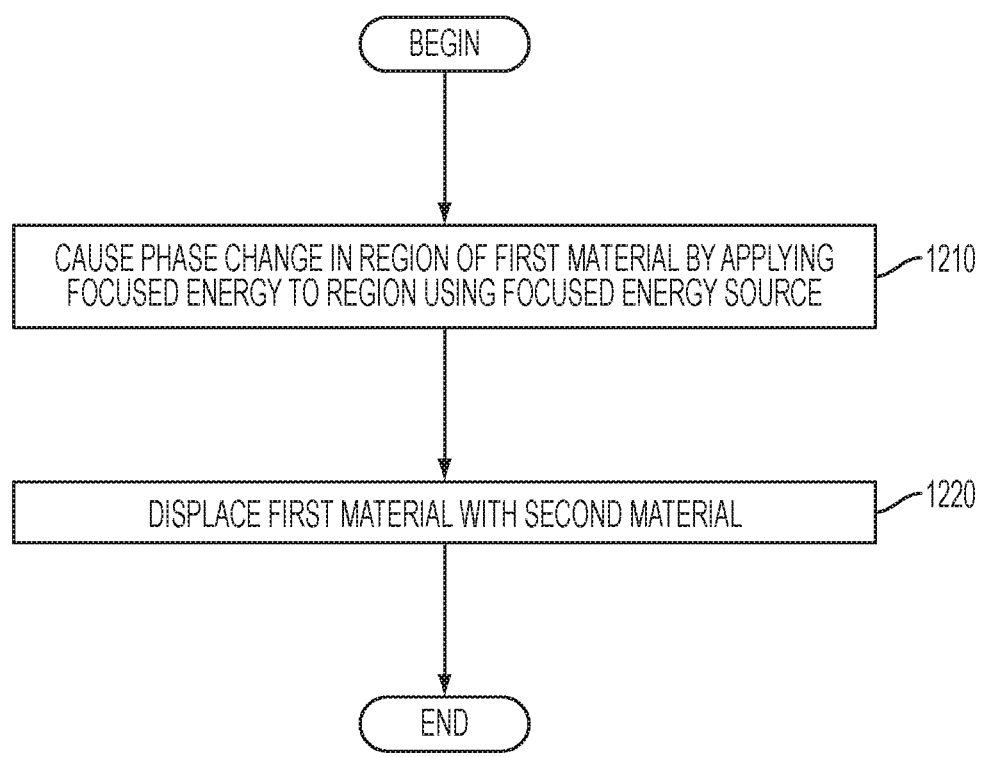
FIG. 12A is a flowchart of a method for three-dimensionally printing according to some embodiments.

FIG. 12A illustrates a method for three-dimensionally printing. The method begins at act 1210, at which a phase change may be caused in a region of a first material by applying focused energy to the region using a focused energy source. That material may be a material that may undergo a change from a less fluid to a more fluid state upon introduction of energy. The method then proceeds to act 1220, at which the first material may be displaced with a second material.

Figure 12B:
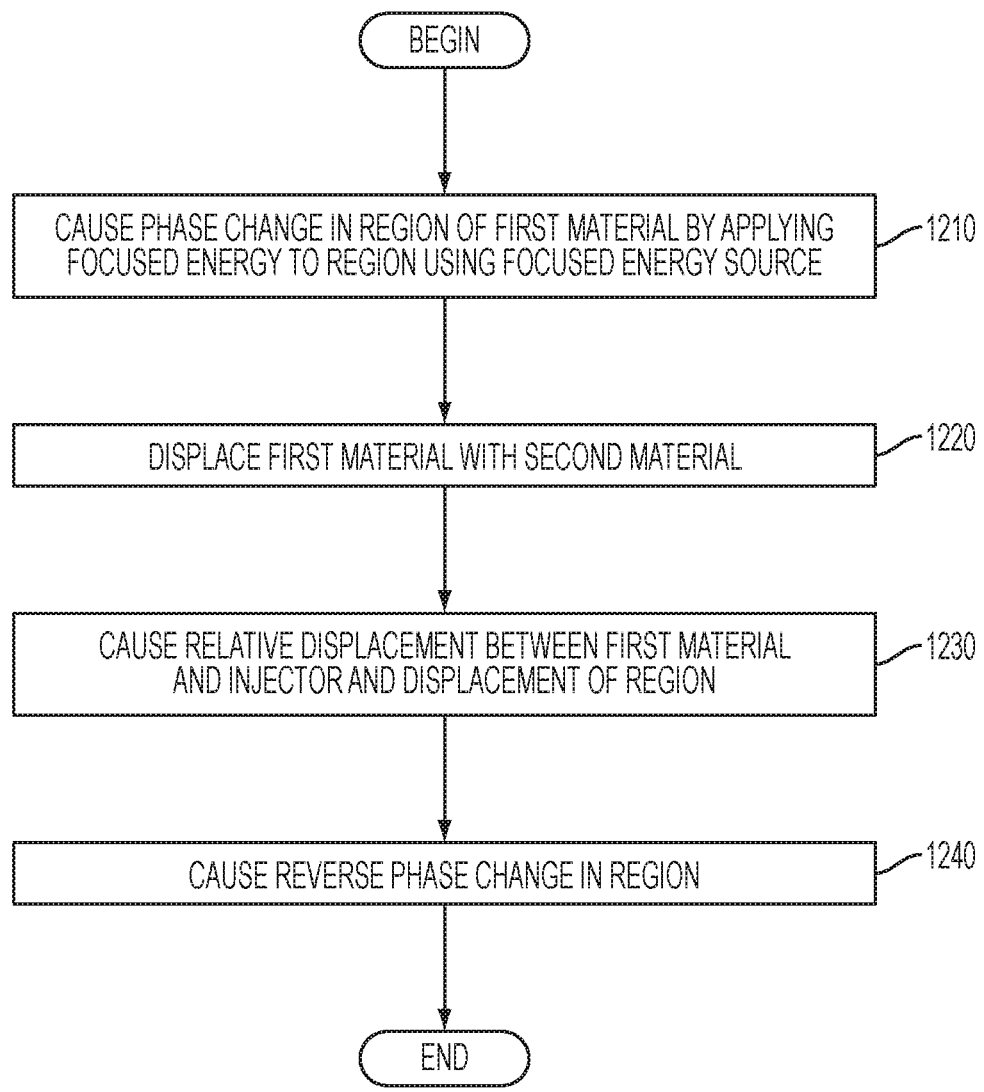
FIG. 12B is a flowchart of another method for three-dimensionally printing according to some embodiments.

It should be further appreciated from the foregoing that other embodiments are directed to a method for three-dimensionally printing, as illustrated in FIG. 12B. The method begins at act 1210, at which a phase change may be caused in a region of a first material by applying focused energy to the region using a focused energy source. The method then proceeds to act 1220, at which the first material may be displaced with a second material. The method then proceeds to act 1230, at which relative displacement between the first material and the injector and displacement of the region are caused. The method then proceeds to act 1240, at which a reverse phase change in the region is caused.

Additional Exemplary Implementation of the System

Figure 13:
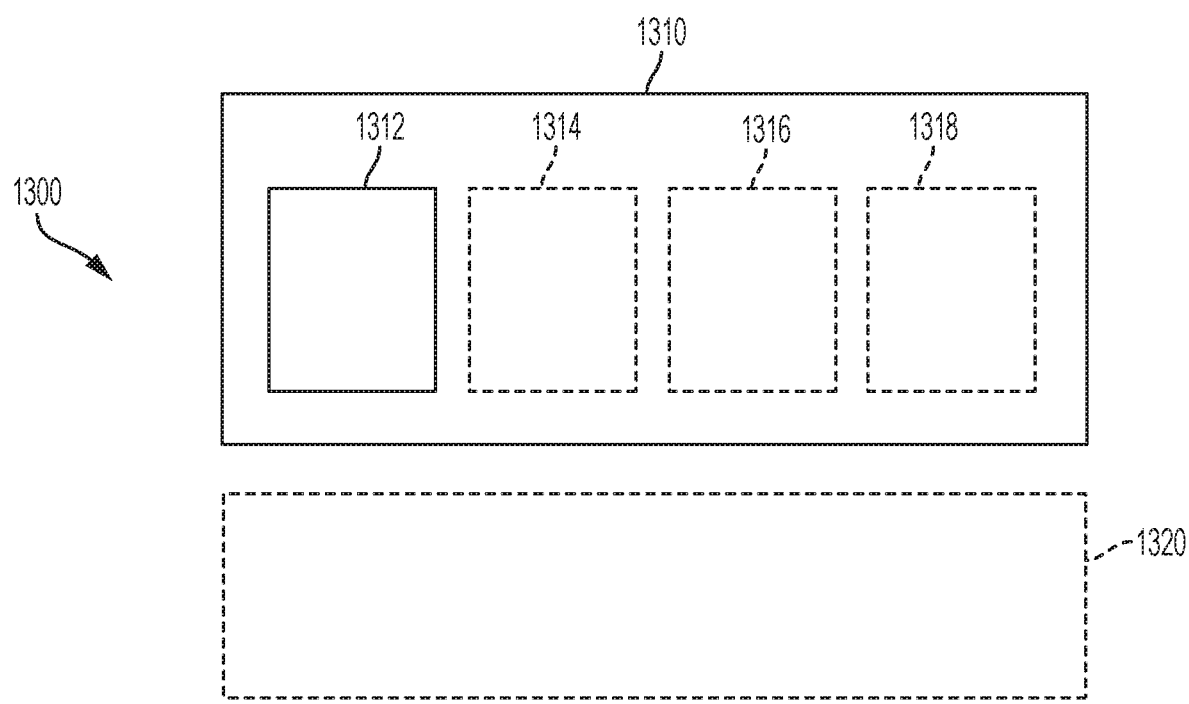
FIG. 13 is a diagram illustrating a system for three-dimensionally printing a tissue construct according to some embodiments.
Figure 14:
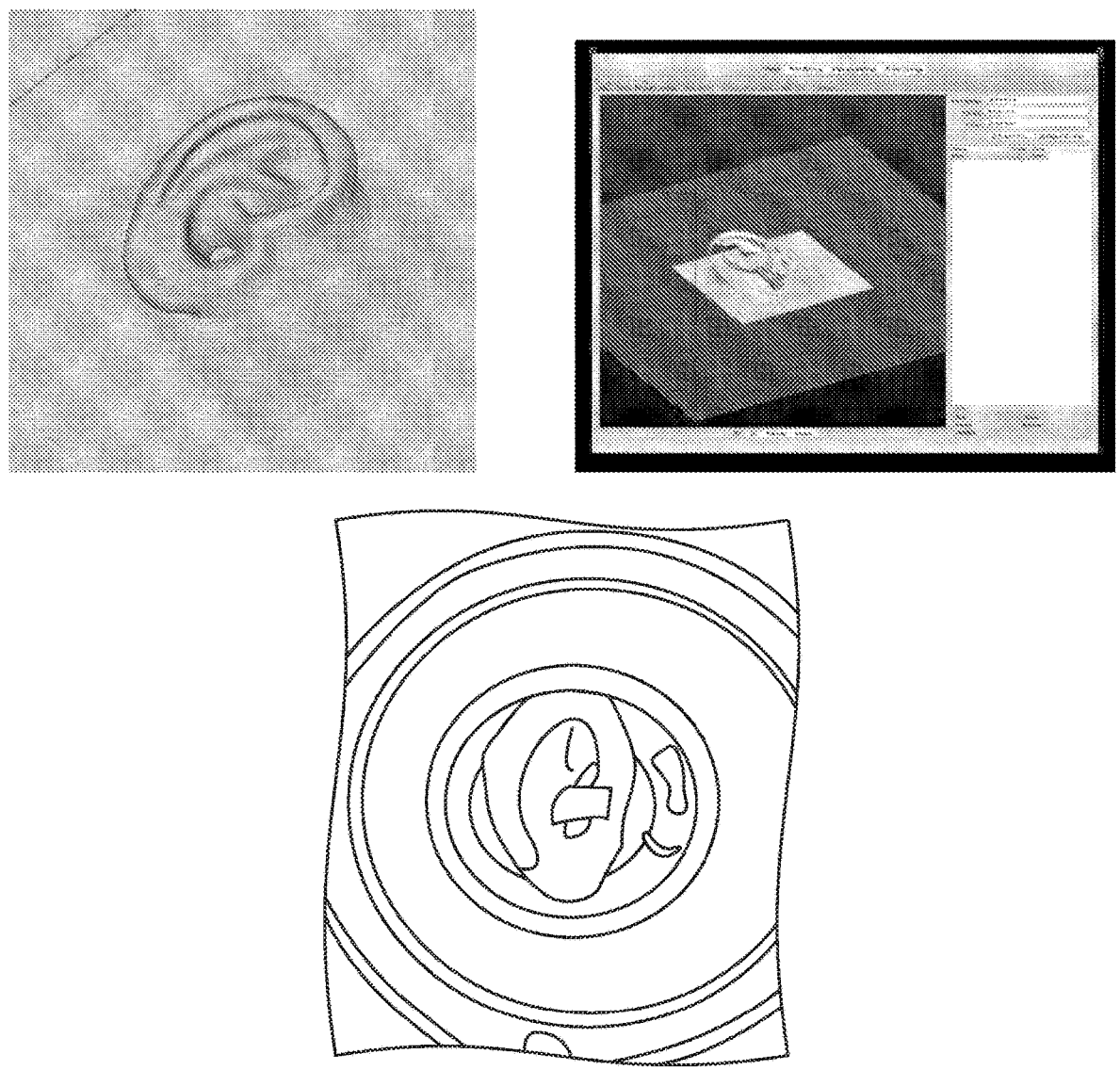
FIG. 14 is a diagram illustrating an exemplary tissue construct created from a three-dimensional model using commercially available software according to some embodiments.

FIG. 13 illustrates an exemplary system 1300 for creating a three-dimensional tissue construct of a desired shape for repair or replacement of a portion of an organism. For example, the tissue construct may be in the shape of and have the characteristics of a human ear (FIG. 14). The tissue construct may then be attached to the organism. The tissue construct may be a tissue repair scaffold, such that the tissue construct may merge with the organism by tissue from the organism growing into the tissue construct. In some embodiments, one or more components of the system 1300 may operate in accordance with techniques and components discussed above in connection with FIGS. 9, 11, and 12A-12B.

The system 1300 may include an apparatus 1310. The apparatus 1310 may include an injector 1312. According to some embodiments, the injector 1312 may be configured to inject one or more biomaterials and/or one or more cells or one or more types of cells in a three-dimensional pattern into a first material such that the printed material(s) are held in the desired shape of the tissue construct by the first material. The first material may include a yield stress or thixotropic material. According to some embodiments, the injector 1312 may cause a phase change in a region of the first material by applying focused energy to the region using a focused energy source, as described herein. Additionally, the injector 1312 may displace the first material in the region with the biomaterial(s) and/or cell(s).

According to some embodiments, the apparatus 1310 may also include a removal mechanism 1314, an insertion mechanism 1316, and/or an attachment mechanism 1318. According to some embodiments, the removal mechanism 1314 may be configured to remove the injected biomaterial(s) from within the first material, such as by draining or washing away the first material in whole or in part. The removal mechanism 1314 may therefore, in some embodiments, including a second injector to inject a material to wash away the first material, such as an injector to inject a solvent and/or a salt. The insertion mechanism 1316 may be configured to insert the tissue construct into a tissue cavity of the organism. The insertion mechanism 1316 may include a support to hold and support the tissue construct during the insertion, and may include at least one articulating member attached to the support to move the support to the tissue cavity such that the tissue construct can be placed into the tissue cavity from the support or is only a short distance from the tissue cavity. The insertion mechanism 1316 may additionally, in some embodiments, include a drive engine to move the articulating member(s) and thereby move the support. In other embodiments, the articulating member(s) may be (alternatively or additionally) manually movable. The attachment mechanism 1318 may be configured to attach the tissue construct to the organism, such as with adhesive, stitching, suction, precise placement, and/or any other suitable attachment technique. The attachment mechanism 1318 may also be configured to cover the wound or tissue cavity with flaps of skin or other suitable tissue or material and/or any suitable healing dressing. The insertion mechanism 1316 and/or the attachment mechanism 1318 may include one or more surgical tools, such as known robotic surgical tools, to support moving and attachment of tissues.

According to some embodiments, the apparatus 1310 and/or the system 1300 may also include at least one processor. Additionally, the system 1300 may include a three-dimensional scanner 1320, which may be a laser scanner, x-ray device, computerized tomography (CT) device, and/or magnetic resonance imaging (MRI) device, or other device configured to detect and/or measure placement and dimensions of one or more types of tissues on an exterior and/or interior of an organism.

The processor(s) may be configured to prepare a model of the tissue construct that is to be produced by the system 1300. The model of the tissue construct may define the shape of the tissue construct as well as the type(s) of material(s) to be included in the tissue construct and the locations in the tissue construct at which each type of material will be disposed. The shape of the tissue construct may include a topographic shape, such as a topographic shape of a portion of the tissue construct that is to interface with remaining tissues of the organism (e.g., that is to interface with tissues of the organism surrounding a wound). For example, a tissue construct designed to merge with a portion of an organism with exposed smooth muscle may be made with biomaterials compatible with smooth muscle and/or may include cells that are smooth muscle or may develop into smooth muscle tissue (e.g., stem cells that may encourage growth of smooth muscle cells). Other portions of the tissue construct may be made of material compatible with other types of tissue in the organism in contact with the tissue construct, such as bone. Similarly, the tissue construct may be designed with openings to align with vasculature in the organism. These parameters of the tissue construct may be represented in the model.

Preparing the model may include scanning a tissue region (e.g., in the area of a tissue cavity such as a wound) of the organism that will receive the tissue construct using the three-dimensional scanner 1320. The scanner may be used, for example, to determine a topology of the tissue region. As part of scanning the tissue region that will receive the tissue construct, connective tissues may be identified in the tissue region. For example, the location and dimensions of blood vessel endings, bone endings, cartilage endings, tendon or ligament or other musculature endings, dermal endings, or portions of other tissues that are to be connected to tissues to be grown in the tissue construct may be identified. Preparing the model may also include generating the model of the tissue construct so that the tissue construct includes the following: cells serving as and/or biomaterial adapted to encourage growth of a bone replacement adjacent a location of bone identified in the organism, cells serving as and/or biomaterial adapted to encourage growth of a muscle replacement adjacent a location of muscle identified in the organism, and/or cells serving as and/or biomaterial adapted to encourage growth of a vasculature replacement adjacent a location of vasculature identified in the organism. The size and tissue type may be identified through the scanning or in any other suitable way.

Alternatively or additionally, preparing the model may include downloading the model from a model repository or any other suitable source.

According to some embodiments, preparing the model of the tissue construct may additionally or alternatively include scanning a healthy body part. For example, if one leg of a human subject is wounded or has missing or damaged tissue for any other reason, the processor(s) may use the three-dimensional scanner 1320 to scan a corresponding tissue region of the human subject's healthy leg, if it is available, as a source of data for preparing the model of the tissue construct, such as using scanners discussed above (e.g., x-ray, CT, MRI, etc.). The processor(s) may combine the results of the scanning of the tissue region of the organism with the results of the scanning of the corresponding tissue region of the healthy body part (e.g., the healthy leg). In some cases, when a corresponding healthy region is used, one or more adjustments may need to be made to produce a model of the healthy region that may be combined with the scan of the tissue region. As an example of such an adjustment, a mirror image of the placement of the tissues of the healthy region may need to be produced for combination with scanning of the tissue region, because the corresponding healthy region may be a reflection of the tissue region due to biologic bilateral symmetry. As another example, if a corresponding healthy region is scientifically known to vary from the tissue region, such as variations in size and structure of human lungs, for example, these known variances may be used to make adjustments to the model of the corresponding healthy region to produce a model of the tissue region. The processor(s) may then generate the model of the tissue construct based on the results of this combination. For example, the processor(s) may perform a Boolean operation to determine the differences between the healthy body part and the tissue region of the organism and use these differences as a basis for generating the model of the tissue construct.

Additionally or alternatively, preparing the model of the tissue construct may comprise receiving user input, such as from a clinician inspecting a tissue region, identifying a location of connective tissues and/or of tissues that are to be grown in the organism once the tissue construct is inserted.

According to some embodiments, preparing of the model of the tissue construct may be performed using commercially available software, which may include "off the shelf" scanning, modeling, and/or printing software (FIG. 14). For example, common 3D model file formats may be used to create the tissue construct in common 3D modeling and printing software. The inventors have recognized and appreciated that using commercially available software may reduce the cost and increase the speed of the 3D printing techniques described herein.

According to some embodiments, the biomaterial may be configured to support at least two cell types. For example, the cell types may include bone cell, smooth muscle cell, skeletal muscle cell, vascular cell, and/or any other cell type. Alternatively or additionally, the biomaterial may include at least two material types, which may include material for bone, material for smooth muscle, material for skeletal muscle, material for vasculature, and/or any other suitable material type. The material for bone may include hydroxyapatite based matrices. The material for smooth muscle may include a first hydrogel functionalized with adhesive ligands. The material for skeletal muscle may include a second hydrogel with higher stiffness than the first hydrogel and that is adhesive and configured to stretch periodically. The material for vasculature may include a third hydrogel functionalized with vascular endothelial growth factor.

As should be appreciated from the foregoing, the biomaterial(s) that are printed in the tissue construct may include natural and/or synthetic polymer matrices compatible with implantation into an organism. The natural polymer matrices may include naturally-occurring extracellular matrix materials. Such naturally-occurring extracellular matrix materials may include a biopolymer network in which living cells may be embedded or may grow. The biopolymer network may include one or more of collagen, elastin, fibronectin, and laminin. Other exemplary materials include polysaccharides gels such as alginate and agarose, proteins gels such as fibrinogen, collagen, Matrigel®, synthetic polymer hydrogels such as poly(acrylamide), poly(ethylene glycol) diacrylate, poly(acrylic acid), and any other suitable material. The three-dimensional shape of these matrices may again be formed using temporarily phase changed material as an outer fluid and pre-gelled solution into which the matrices are printed using techniques described herein and with/without cells as the inner fluid. In some embodiments, the pre-gelled material can be crosslinked using chemical or physical (heat, UV irradiation) treatment. The support material (now used as sacrificial material) may be washed away by diluting with salts and/or organic solvents and eventually immersed in aqueous culture media.

When biomaterial is to be printed to be compatible with and/or encourage growth of a particular type of cell/tissue, the biopolymer network may include one of those materials, or a combination of those materials in a ratio, that is known to be compatible with and/or encourage growth of that particular type of cell/tissue. For example, a biomaterial that is adapted to encourage growth of epidermal tissue may contain elastin in a higher proportion than a biomaterial that is to encourage growth of subdermal tissue. The biomaterial may additionally include other materials that are known to encourage growth of particular tissues. For example, biomaterial that is to be compatible with or encourage growth of bone may include hydroxylapatite. As another example, biomaterial that is to be compatible with or encourage growth of blood vessels may include vascular endothelial growth factor. Biomaterial that is to be compatible with or encourage growth of a type of tissue may be chosen to have properties based on properties of the tissue with which the biomaterial is to be used. For example, a biomaterial adapted to encourage growth of skeletal muscle tissue may be arranged to be stiffer/firmer than a biomaterial that is adapted to encourage growth of adipose fat tissue, because skeletal muscle tissue is stiffer/firmer than adipose fat tissue.

In some embodiments, tissue constructs may be printed with feature sizes of less than 1 millimeter. The feature size may, in some embodiments, be less than 100 micrometers, less than 50 micrometers, less than 10 micrometers, or up to 1 micrometer. In some embodiments, a minimum feature size of a tissue construct may be governed by thermal forces, such that when features are printed with feature sizes less than the minimum feature size, the deposited material drifts from its deposited position due to thermal forces and precision may be lost. Accordingly, in some embodiments, the smallest feature size of the tissue construct may be approximately one micrometer, or ten micrometers. For example, the tissue construct may have microscale detail that includes features the size of a microscopic, biological cell.

In some embodiments, a tissue construct printed using apparatuses and/or techniques described herein may not be self-supporting, such that the tissue construct may collapse under its own weight unless supported. As should be appreciated from the foregoing, a support material or scaffold may not be printed with the tissue construct, but rather the tissue construct may be printed in a bath of yield stress material that supports the construct. As such, the tissue construct may not include any support material, such that the tissue construct may only include biomaterial that is adapted to encourage growth of cells/tissues. The tissue construct, when removed from the yield stress material, may not include any support materials. The tissue construct, when printed in the yield stress material and when removed from the yield stress material, may not include any materials that are to be removed from the tissue construct prior to insertion in a tissue cavity.

According to some embodiments, the duration required in creating the tissue construct may be one or a few minutes or up to one hour, such as in some embodiments in which a tissue construct is printed with biomaterial and without cells. Alternatively, the duration required may be longer in other embodiments, including in some embodiments in which cells are deposited in a tissue construct.

According to some embodiments, high speed manufacturing methods may also be used to increase the speed of creation of a tissue construct and/or inserting the tissue construct into a tissue void.

Figure 15:
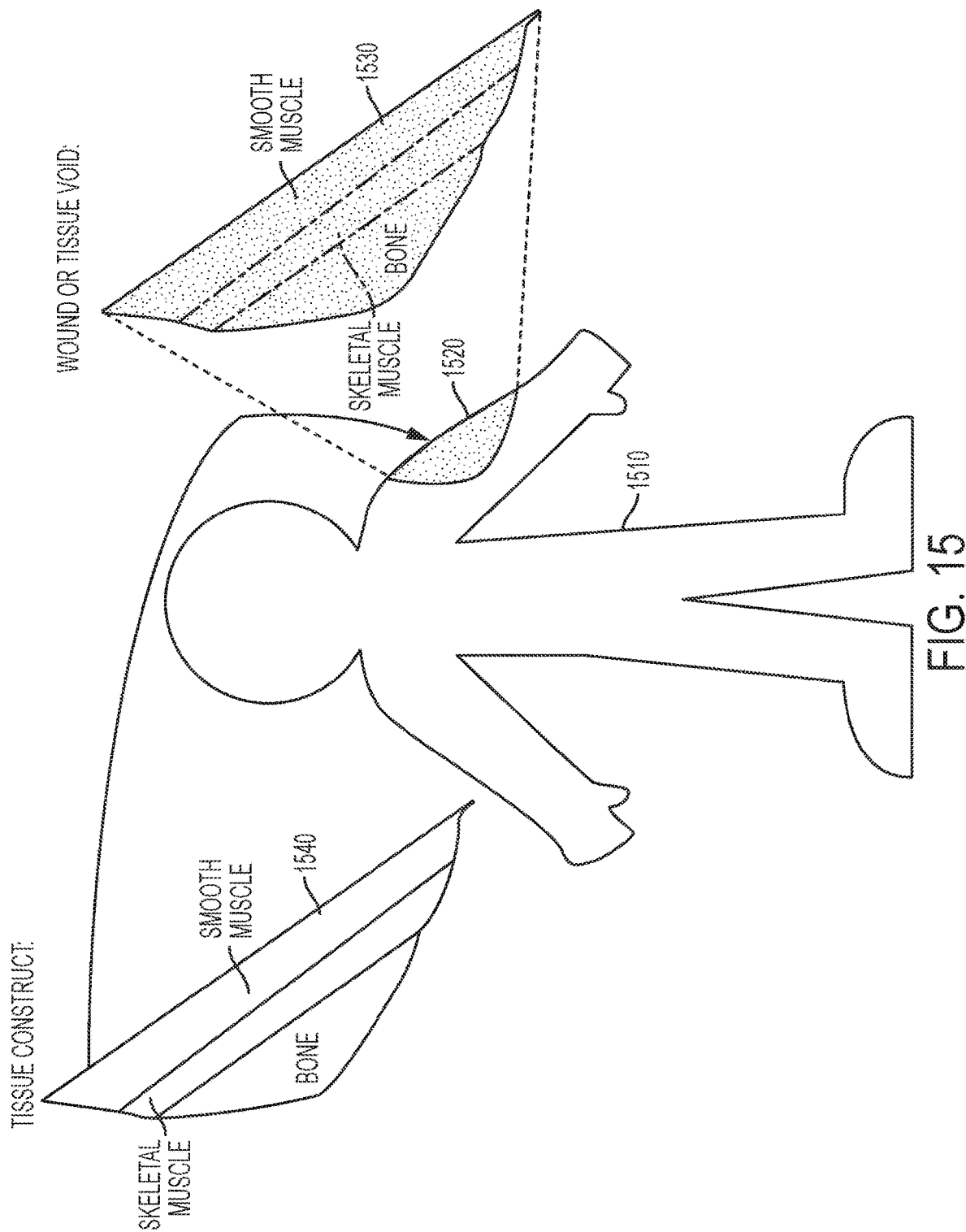
FIG. 15 is a diagram illustrating an exemplary wound or tissue void of an organism and a tissue construct created to replace or repair the wound or tissue void according to some embodiments.

FIG. 15 illustrates an exemplary wound or tissue void of an organism and a tissue construct created to replace or repair the wound or tissue void according to some embodiments. According to some embodiments, the wound or tissue cavity 1520 may include missing bone tissue, missing skeletal muscle tissue, missing smooth muscle tissue, and/or any other suitable tissue, as illustrated in the enlarged section 1530 of a wound or tissue void 1520 in a human subject's 1510 arm. A tissue construct 1540 may be created with a desired shape for repair or replacement of a portion of an organism, such as this wound or tissue cavity 31520.

According to some embodiments, the tissue construct 1540 may include multiple biomaterials set in a three-dimensional structure. For example, the biomaterials may include a muscle replacement biomaterial and biomaterial identifying passages for vasculature. Alternatively or additionally, the biomaterials may include two or more of the following: a biomaterial that supports growth of bone cell, a biomaterial that supports growth of smooth muscle cell, a biomaterial that supports growth of skeletal muscle cell, or a biomaterial that supports growth of vascular cell.

According to some embodiments, as should be appreciated from the foregoing, the biomaterial that supports growth of bone cell may include hydroxyapatite based matrices. The material that supports growth of smooth muscle cell may include a first hydrogel functionalized with adhesive ligands. The biomaterial that supports growth of skeletal muscle cell may include a second hydrogel with higher stiffness than the first hydrogel and that is adhesive and configured to stretch periodically. Alternatively or additionally, the biomaterial that supports growth of vascular cells may include a third hydrogel functionalized with vascular endothelial growth factor.

According to some embodiments, the biomaterials may include two or more of the following: a bone replacement biomaterial, a smooth muscle replacement biomaterial, a skeletal muscle replacement biomaterial, or a vasculature replacement biomaterial. The bone replacement biomaterial may include hydroxyapatite based matrices. The smooth muscle replacement biomaterial may include a first hydrogel functionalized with adhesive ligands. The skeletal muscle replacement biomaterial may include a second hydrogel with higher stiffness than the first hydrogel and that is adhesive and configured to stretch periodically. Alternatively or additionally, the vasculature replacement material may include a third hydrogel functionalized with vascular endothelial growth factor.

Figure 16:
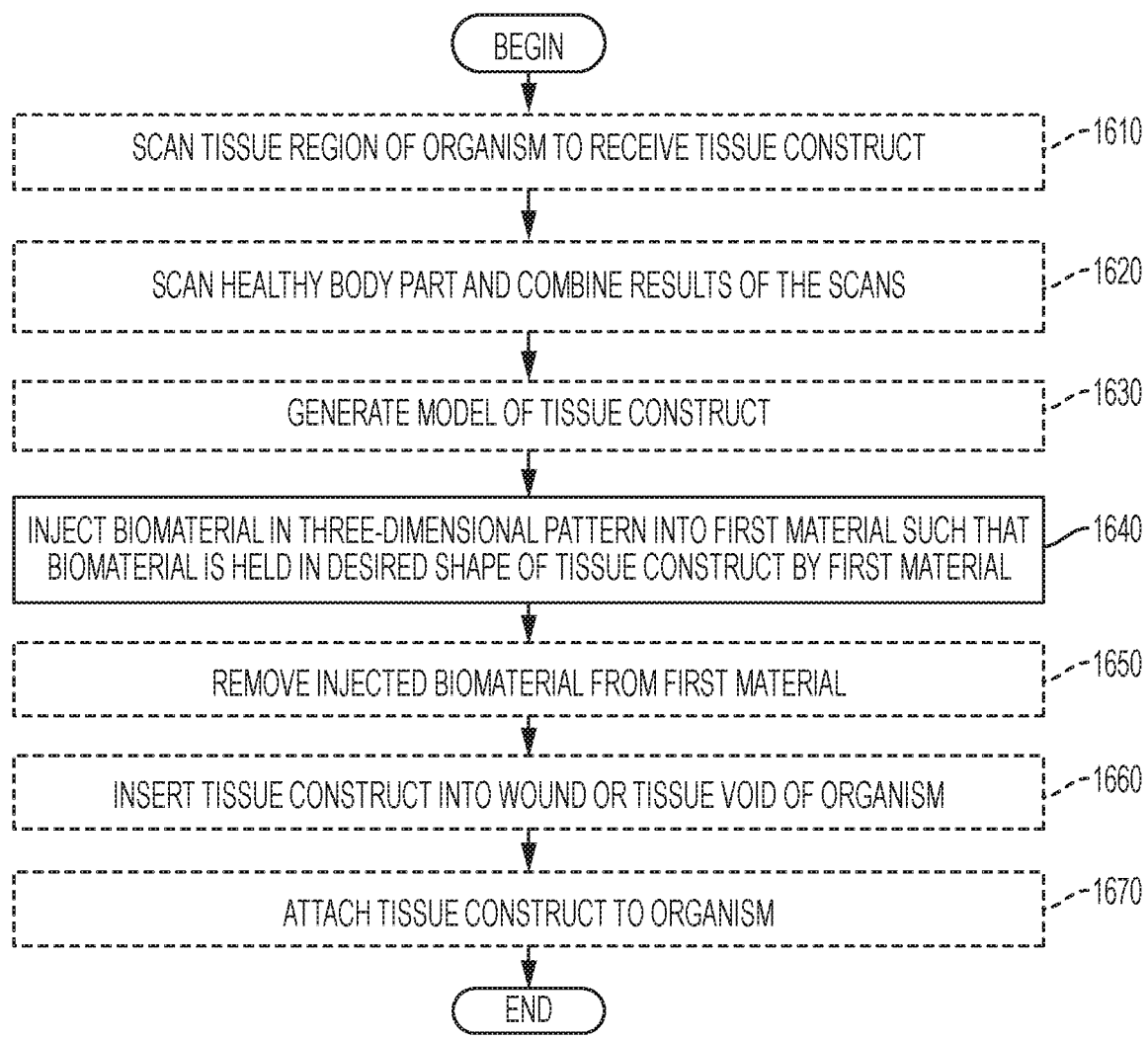
FIG. 16 is a flowchart of a method for three-dimensionally printing a tissue construct according to some embodiments.

It should be appreciated from the foregoing that some embodiments are directed to a method for three-dimensionally creating a tissue construct, as illustrated in FIG. 16. The method optionally begins at act 1610, at which a tissue region of an organism that is to receive a tissue construct may be scanned. The method then optionally proceeds to act 1620, at which a healthy body part may be scanned and the scan of the tissue region may be combined with the scan of the healthy body part. Optionally, the method then proceeds to act 1630, at which the tissue construct model may be generated.

The method then proceeds to act 1640, at which biomaterial may be injected in a three-dimensional pattern into a first material such that the biomaterial is held in the desired shape of the tissue construct by the first material. Optionally, the method then proceeds to act 1650, at which the injected biomaterial may be removed from the first material. Optionally, the method then proceeds to act 1660, at which the tissue may be inserted into the wound or tissue void of the organism. The method then optionally proceeds to act 1670, at which the tissue construct may be attached to the organism.

The method may then end. However, treatment of the person, or other organism to which the tissue construct is attached may continue as is known in the art. After the tissue construct is attached to the organism, for example the wound or area of attachment may be periodically irrigated or otherwise treated as is known in the art to promote growth of the tissue from the organism to merge the construct and the organism.

In some embodiments in which the tissue construct is to be inserted into a tissue cavity of a wound, the entirety of the method of FIG. 16 may be performed while a patient is hospitalized for treatment of the wound and, in some cases, may be completed before the patient is stabilized for the wound, such as within 48 hours of the patient being wounded.

In some embodiments, the tissue construct may be removed from the first material and inserted into a tissue cavity without additional treatment or processing being performed on the tissue construct. For example, the insertion of block 1660 may directly follow removal of block 1650, such that no other processing or treatment of is performed on the tissue construct. The insertion of block 1660 may follow removal of block 1650 without delay, such that insertion follows removal only by an amount of time corresponding to trafficking/delivery of the tissue construct and preparation of a tissue cavity for insertion. For example, the insertion may follow removal by 48 hours or less, such as less than 1 day or less than 12 hours or less than 1 hour.

In some embodiments, the insertion of block 1660 may follow the removal of block 1650 without the tissue construct being disposed in any bioreactor or in any device that encourages cell or tissue growth. In some embodiments, between removal of block 3550 and insertion of block 1660, the tissue construct may be kept in a state to inhibit, discourage, or not encourage cell or tissue growth, such as by being refrigerated. In some embodiments, between removal of block 1650 and insertion of block 1660, the tissue construct may not be exposed to cell growth media or other materials that would encourage cell or tissue growth in the tissue construct. In some embodiments, between removal of block 1650 and insertion of block 1660, the tissue construct may not be intentionally exposed to cells or tissues that are to be grown in the tissue construct.

It should be appreciated from the foregoing, however, that in some embodiments cells may be printed and/or tissues may be grown in a tissue construct prior to insertion of the tissue construct into a tissue cavity. Thus, it should be appreciated that embodiments are not limited to operating in scenarios in which a tissue construct is inserted without delay following printing or removal, or embodiments in which a tissue construct is held in a state to inhibit cell or tissue growth. In some such embodiments, when a tissue construct of biomaterial is printed without cells, following printing and prior to insertion of the tissue construct into a tissue cavity, the tissue construct may be exposed to cells, including by having cells deposited in the tissue construct. In some such embodiments, the cells may be injected into a yield stress material in which the tissue construct was printed, without the tissue construct being removed from the yield stress material. For example, cells may be injected at positions in the tissue construct adjacent to positions of biomaterial that will encourage growth of those cells. Following printing of cells, the tissue construct may be removed from the yield stress material and inserted into a tissue cavity.

Exemplary Shapes that May be Produced Using Printing Techniques Described Herein Described above are examples of printing apparatuses and printing techniques that may be used to deposit biomaterials to create tissue constructs, such as for use with encouraging tissue growth during healing of wounds. Described below are examples of structures that may be printed using some such printing apparatuses/techniques with a variety of materials. Some such structures may be printed in some embodiments in connection with printing tissue constructs.

Figure 17:
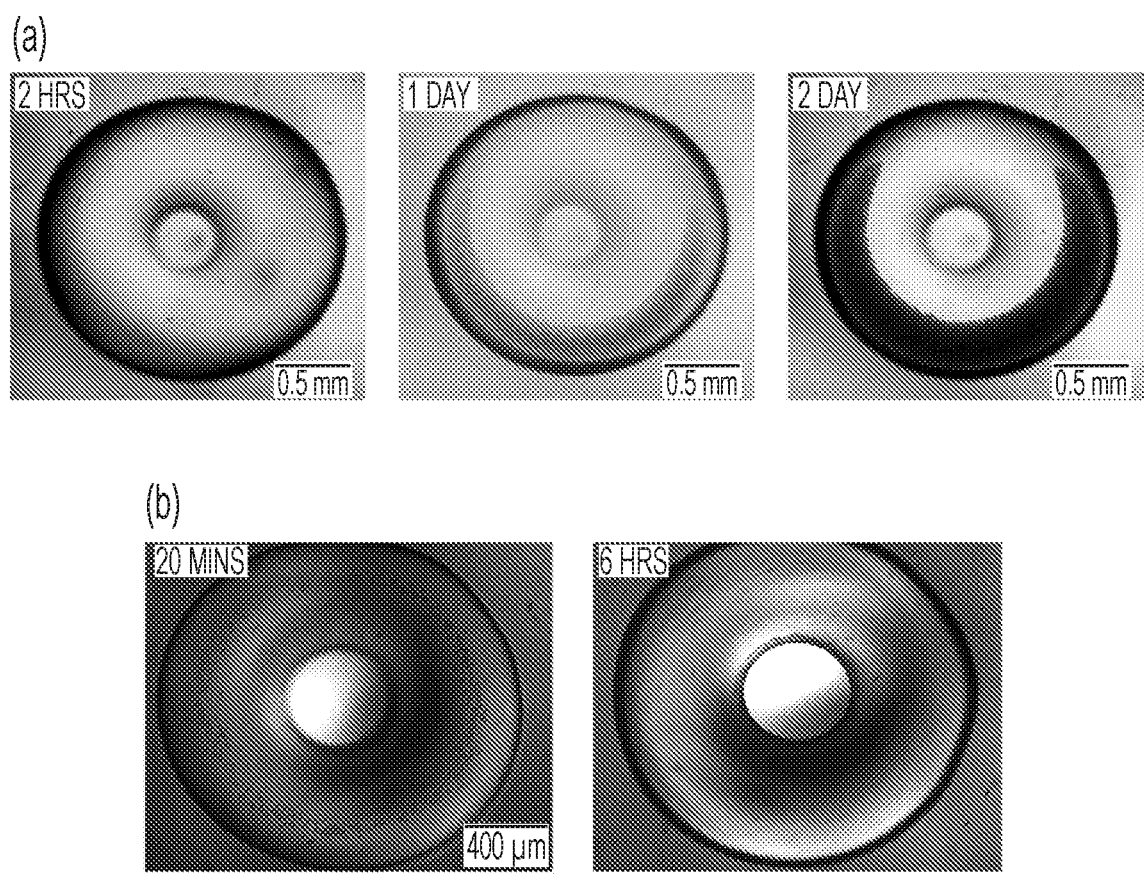
FIG. 17 illustrates examples of (a) yeast cells and (b) MDCK epithelial cells cultured in a toroidal droplet that may be formed using techniques as described herein according to some embodiments, where epithelial cells may migrate toward regions of negative Gaussian curvature, and non-motile yeast cells may divide and grow from positions where the population has initially sedimented.

FIG. 17 illustrates examples of (a) yeast cells and (b) MDCK epithelial cells cultured in a toroidal droplet according to some embodiments, where epithelial cells may migrate toward regions of negative Gaussian curvature, and non-motile yeast cells may divide and grow from positions where the population has initially sedimented.

Figure 18:
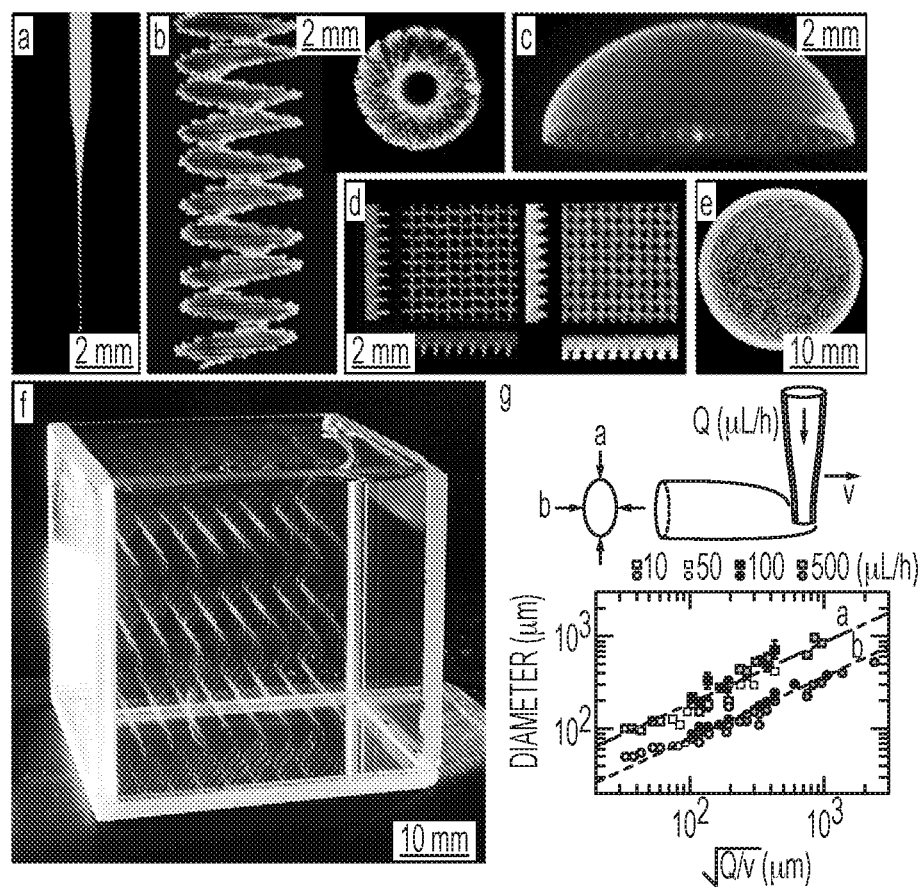
FIG. 18 illustrates examples of stable writing in a granular gel medium using techniques as described herein according to some embodiments.

FIG. 18 illustrates examples of stable writing in a granular gel medium using techniques as described herein according to some embodiments: a) Injection tip filled with fluorescent microsphere suspension, imaged under UV illumination. b) The tip may revisit the same points in space hundreds of times to create a structure resembling DNA written with aqueous fluorescent microsphere suspension in aqueous GGM (UV illumination, side and top views). c) A hemispherical cap made from uncrosslinked 1 µm microspheres, created six months before photographing, exhibits long-term stability provided by the GGM. d) Maximum intensity projections (x, y, and z directions) from confocal microscopy z-stacks of PVA mesh (left) and PDMS mesh (right) show uncrosslinked polymer structures stabilized by the GGM. e) Thin rods may be written in the GGM, photo-crosslinked, removed from the granular gel, and placed in a pertri-dish, where they align and bend. f) These vertical chiral rods may hold their shape and orientation with no signs of gravitational effects while in the GGM. g) Feature width measured along two directions show a universal scaling as a function of flow rate, Q, and tip speed v.

To explore the stability of writing in granular gels, we have generated several complex structures that would otherwise disperse, sag, or fall apart. For example, we created a 4 cm long model of B-DNA by arranging long thread-like features approximately 100 µm in diameter made entirely from uncrosslinked 1 µm fluorescent microspheres. While creating these complex three-dimensional structures, the writing tip traverses the same point in space hundreds of times. The soft GGM may permit repeated retracing of the writing needle because the jamming/unjamming transition occurs locally and without a change in composition or material properties. These structures were incredibly stable over time, with the oldest retained model exhibiting no visible changes over more than six months (FIG. 18a-c). The stability of the GGM can be further illustrated by considering a limiting case; a gold sphere with a diameter of 400 µm will not sink in a GGM with a middle-ranged yield stress of 50 Pa.

Polymeric structures are of growing interest for their potential use in medicine and flexible electronics [74]. Mixtures of polymer and colloids were written into the GGM; mesh structures made from poly-vinyl-alcohol (PVA) in aqueous GGM, and polydimethylsiloxane (PDMS) in oil-based GGM showed excellent stability in their solvent matched medium. The uncrosslinked mesh structures were imaged with confocal fluorescence microscopy and revealed no systematic reduction in surface curvature or feature shape with repeated measurements over several hours (FIG. 18d). The stability and precision gained from writing in the GGM enabled the straightforward production and removal of complex precise structures by crosslinking the polymer after writing.

Condensed anisotropic particles assemble and move in elaborate patterns, and are integral to studies of complex self-assembling materials [75, 76, 77]. We created anisotropic particles in GGM by writing arrays of high aspect ratio 400 µm diameter chiral rods made from photo-crosslinkable PVA and fluorescent microspheres. The PVA hydrogel was photo-crosslinked in the transparent GGM, and after removing the helical rods from the GGM they showed a high degree of flexibility when allowed to freely move and assemble in a water bath. At high packing density, the soft rods locally align from steric interactions and frequently bend with hairpin turns. The low elastic modulus required for such bends to occur was characterized with indentation measurements on individual rods. We found an elastic modulus of about 2 kPa, which is comparable to the elasticity of soft, living tissue cells [78]. Writing in the GGM immediately enables the rapid and precise fabrication of soft, athermal particles over a seemingly unlimited range of size, shape, and form. (FIG. 18e,f).

Freestanding objects with microscopic structural detail may be challenging to produce with soft delicate materials like hydrogels. We have created several complex multiscale structures in the GGM made of crosslinked PVA hydrogels and fluorescent colloids. A simple geometric model of an octopus was made with eight tilted and tapering helical shells that mimic tentacles and a bulbous shell as the body.

Figure 19:
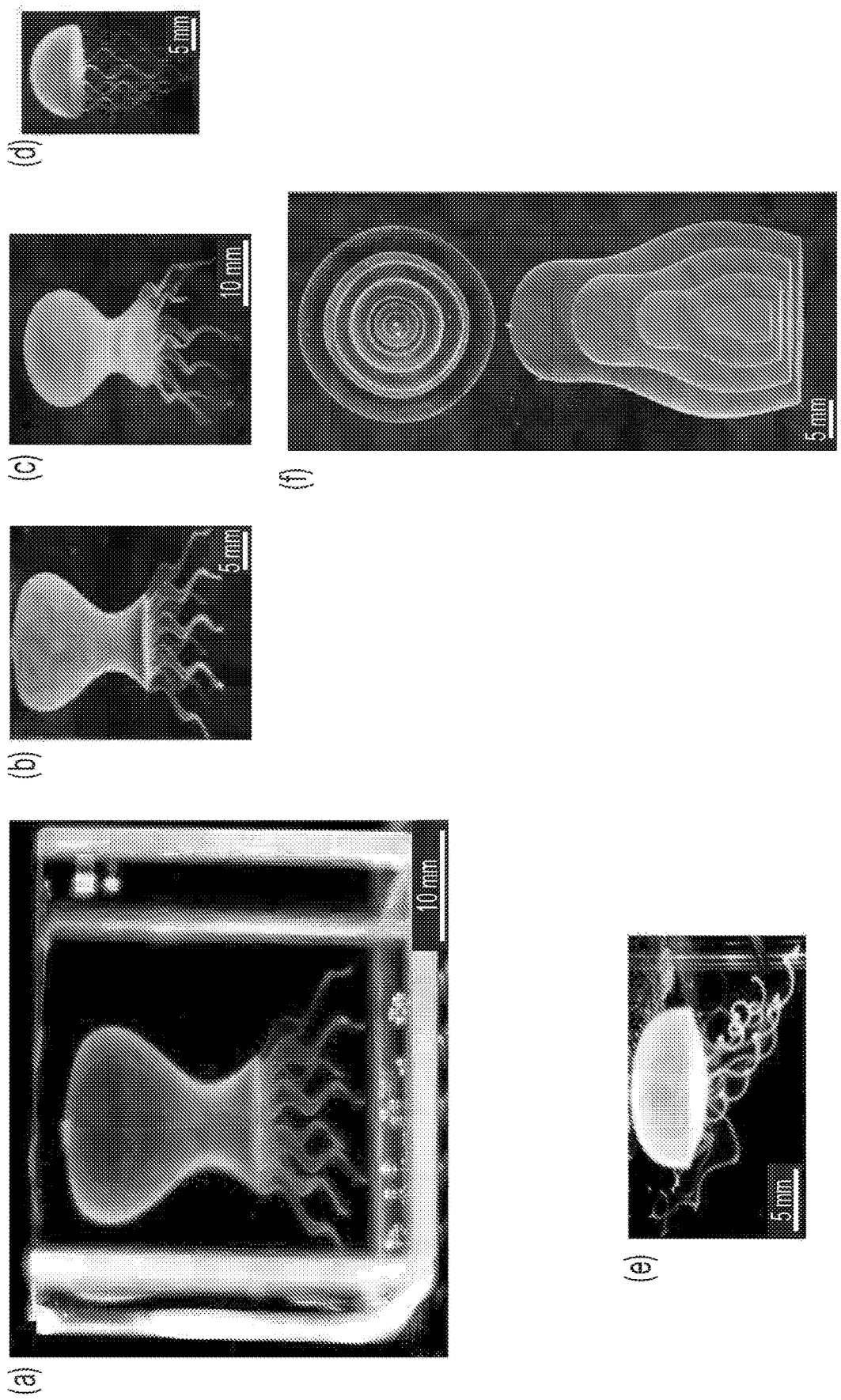
FIG. 19 illustrates a 3D drawing of complex, soft, and robust structures that may be formed using techniques as described herein according to some embodiments.

FIG. 19 illustrates a 3D drawing of complex, soft, and robust structures that may be formed using techniques as described herein according to some embodiments: a) A thin-shell model octopus may be made from multiple connected hydrogel parts with complex, stable surface before polymerization. b) Fluorescence image of octopus model after polymerization, still trapped in GGM, may exhibit no structural changes from the polymerization process. c) Polymerized octopus model may retain integrity after removal from the GGM, shown floating in water. d) A model jellyfish incorporates flexible high aspect ratio tentacles attached to a closed-shell body. e) Freely floating in water, jellyfish model exhibits robustness and flexibility. f) Model Russian dolls demonstrate the ability to encapsulate with nested thin-shells. Photographs in a,c,e were illuminated with white light; b,d,f illuminated with UV light, shown with false-colour LUT to enhance weak features.

In the structure shown in FIG. 19, each tentacle was drawn in a single pass by following surface coordinates along a helical path. The tightly coiled helices had a 100 µm vertical pitch and line-widths approximately 100 µm in diameter. The structure was stable during writing and exhibited no visible changes after UV crosslinking. Crosslinking was performed approximately 6 hours after starting the writing process, demonstrating extremely long working times achievable with this method. The octopus was removed from the GGM by immersion into a gently agitated water bath. After the GGM dispersed, the octopus showed strength and integrity while freely fluctuating in the convective currents (FIG. 19a-c). A similar model of a jellyfish with solid tentacles was created by increasing the volumetric injection rate during writing, and it too exhibited life-like motion (frequently inverting and entangling) in the water bath after removal from the GGM (FIG. 19d,e).

Material encapsulation may be a challenging technological task, and huge advancements may be made by controllably generating capsular three-dimensional co-cultures of multiple cell types, multi-species microbial colonies, diffusively communicating chemical reaction vessels, smart materials with breakable shells for controlled release, or nested conductors for capacitance sensing [79, 80, 81, 82]. Closed shells can be easily manufactured in the GGM, and complex nested structures made from multiplexed arrays of nozzles and materials can be envisioned. To demonstrate the feasibility and ease of encapsulation we created a miniature assembly of nested Russian dolls. Four closed-shell structures were created, with each larger doll containing all of the others inside; the final assembly reveals nearly seamless joining of individual dolls and illustrates the level of control provided by writing in the GGM (FIG. 19f).

The same striations are observed in the octopus and jellyfish models, above, demonstrating that a continuous structure at the limit of feature separation can be achieved by matching the feature width to the helical pitch. These complex tubular network structures were drawn using mixtures of photocrosslinkable PVA and colloidal particles, but in principle any aqueous polymer solution could be used.

The ability to create living tissue on demand is a major goal in bioengineering, but fluid transport remains one of the greatest impediments to making macroscopic structures from living cells [26]. The metabolic needs of cells require a dense vasculature and cell aggregates larger than a few hundred microns cannot survive without such a transport system. Living tissues circumvent this challenge by being packed with interfaces, manifolds, and blood vessels, often found within only a few hundred micrometers from any point in space. To begin to create and study structures as intricate and delicate as living tissue, it may be imperative to controllably produce branched tubular networks. We designed and manufactured a complex tubular network composed of tapered pipes connected by smoothly morphing quaternary intersections, which have both convex and concave curvatures.

Figure 20:
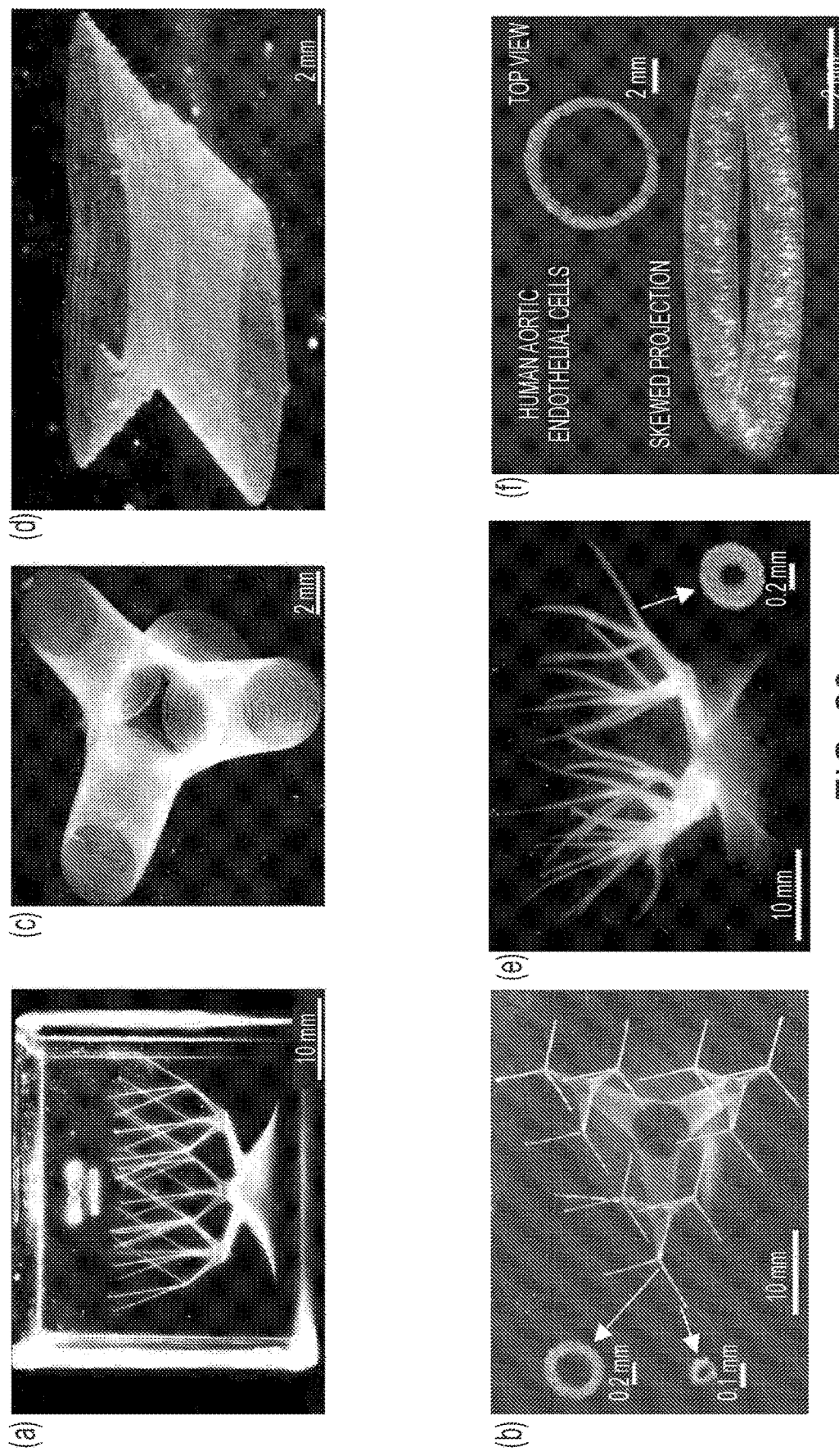
FIG. 20 illustrates hierarchical 3D vascular networks with variable aspect ratio that may be formed using techniques as described herein according to some embodiments.

FIG. 20 illustrates hierarchical 3D vascular networks with variable aspect ratio that may be formed using techniques as described herein according to some embodiments: a,b) A continuous network of hollow vessels with features spanning several orders of magnitude in diameter and aspect ratio (insets: confocal cross-sections). c) A high resolution photo of truncated vessels around a junction shows hollow tubes with thin walls and features approximately 100 µm in diameter. d) Junctions exhibit stable concave and convex curvatures. e) A crosslinked network, removed from the GGM, photographed freely floating in water (inset: confocal cross-section). f) A structure written from only living cells, trapped in granular gel growth media, imaged with confocal fluorescence microscopy. The same tilted tubular structure at the base in d is seen here made from fluorescently labelled HAECs. The image is a maximum intensity projection along a skewed direction, and the inset is the XY slice corresponding to the top of the tubular structure.

The structure of FIG. 20 was written from a single 25 mm diameter circular base and has three levels of division, ultimately ending with 27 narrow capillaries that taper to approximately 100 µm in diameter; the entire structure contains 40 connected vessels and 12 junctions. The wall thickness of these tubes is approximately 100 µm, which is thin enough to image single traces along the writing path when examined under high magnification (FIG. 20a-d).

As one example, we have made vascular networks written entirely out of human aortic endothelial cells (HAECs), without the PVA matrix, but the resulting structures are invisible by eye because the refractive index of cells is so closely matched with water and the printed structures are so thin. We used fluorescence confocal microscopy to image a portion of a junction assembly by writing the structure within the microscope's working distance. Projections and slices from the stack show a tilted hollow tube with ~300 µm thick walls, made from HAECs (FIG. 20f). The shape matches a corresponding structure that was made from polymer and colloids, and has an average variation in thickness on the order of a single cell. Epithelial and endothelial tissues throughout the body are composed of layers just one cell thick; medical fabrication that faithfully follows biological design requires positioning and control at the length-scale of a single cell (FIG. 20d).

Exemplary Experimental Studies Using Materials that May be Used in Some Embodiments Described above are examples of printing apparatuses and printing techniques that may be used to deposit biomaterials and/or cells to create tissue constructs, such as for use with encouraging tissue growth during healing of wounds. Described below are examples of studies that have been performed using such printing apparatuses/techniques with a variety of materials. These studies demonstrate some desirable properties of the printing apparatuses and techniques that may be used in some embodiments.

As should be appreciated from the foregoing, carbomer polymers, including Carbopol®, are one type of yield stress material that may be used in some embodiments to support printing of biomaterials in a tissue construct. Carbopol® is a commercially available material that has been extensively studied [41, 42]. Carbopol® is popular in the study of YSMs because, once yielded, it does not shear thin as strain rate rises, making it "ideal" [4]. MRI velocimetry on Carbopol® samples showed that the local strain is the same as the bulk strain across the yielding threshold [6]; this is noteworthy because it demonstrates Carbopol's® homogeneity, raising the possibility of developing a 3D force microscopy method.

Instrument Construction

Figure 21:
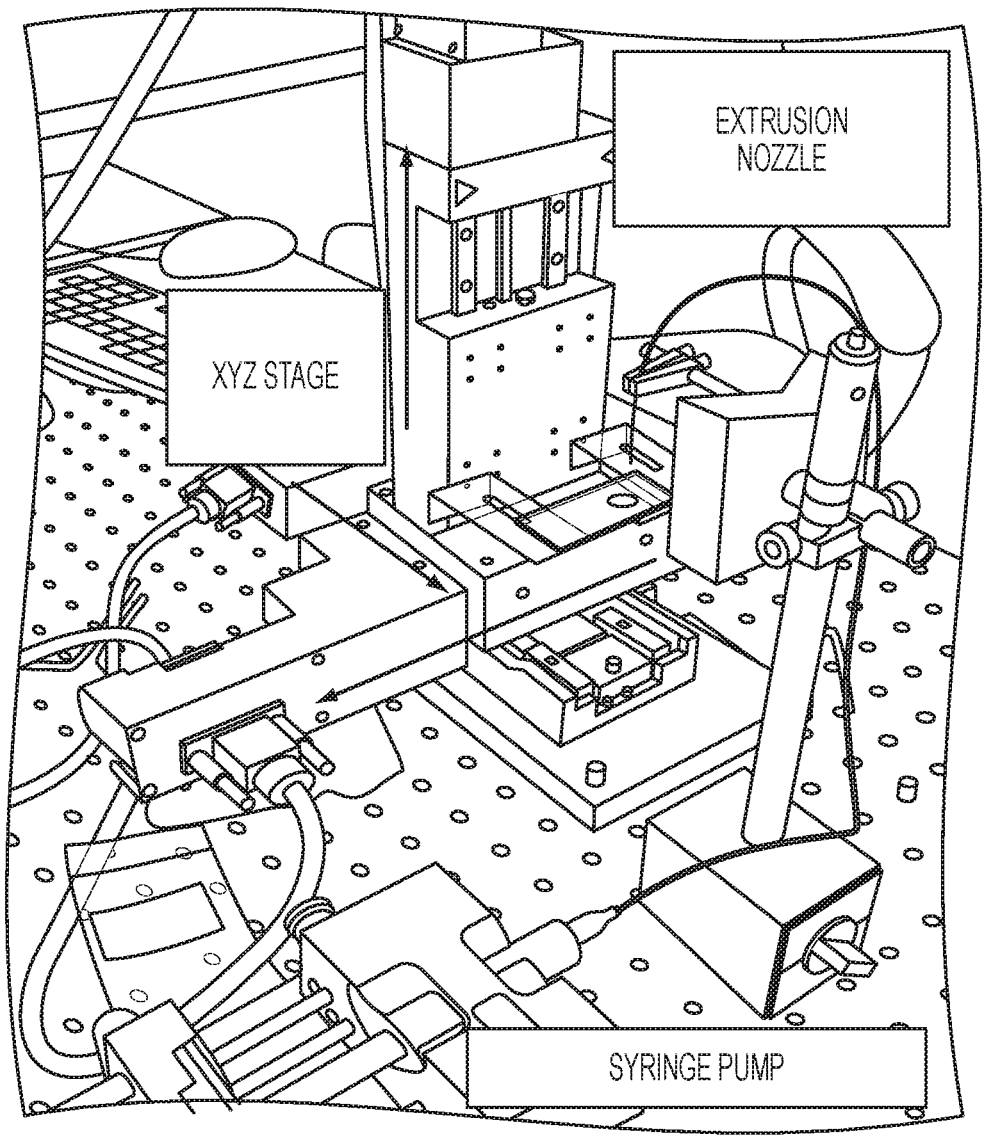
FIG. 21 illustrates a 3D extrusion system for exemplary experimental study according to some embodiments.

The 3D extrusion system may comprise an XYZ stage constructed from three linear translation stages (M-403, Physik Instrumente) driven by Mercury DC motor controllers (C-863, Physik Instrumente). The extrusion system is a computer-controlled syringe pump (Next Advance), held stationary to enable imaging as the stage moves, translating the yield stress support material in 3D (FIG. 21). The extrusion nozzles may be home made from glass pipettes, pulled with a Kopf-750 micropipette puller and shaped with a Narishige micro-forge. The inventors have control over nozzle diameter and shape; nozzle wettability is varied with hydrophilic 3-aminopropyl-triethoxysilane, or hydrophobic octadecyltriethoxysiloxane.

Studies

The inventors have performed studies using two materials: Carbopol® ETD 2020 and Dow-Corning 9041 Silicone Elastomer Blend. The Carbopol® is aqueous and the DC-9041 is silicone oil based. Both consist of packed microgels—microscopic gel particles, ~5 µm in diameter, made from crosslinked polymer (FIG. 4). The yield stress of DC-9041 is controlled by adding or removing PDMS oil; the yield stress of Carbopol® is controlled by water content. Carbopol® yield stress can be varied between roughly 1-1000 Pa [41]; the inventors' tests of DC-9041 reveal a similar range. Thus, both materials can be tuned to span the stress levels that cells typically generate.

Example: Tests of Carbopol®: Aqueous-Aqueous Structures

Figure 22:
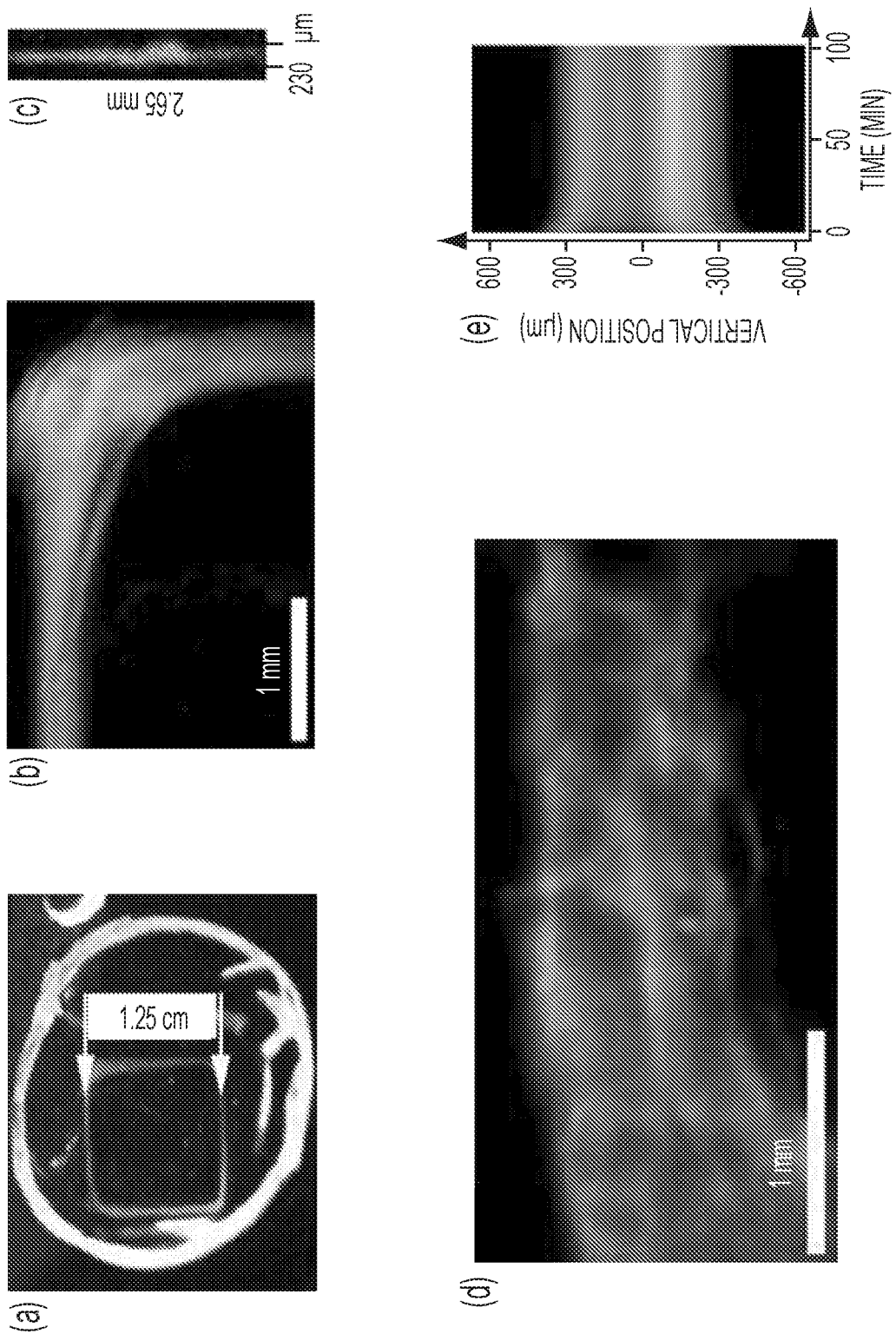
FIG. 22 illustrates extruded structures for exemplary experimental study according to some embodiments.

Cells live in aqueous media and Carbopol® is aqueous. With the 3D extrusion instrument described herein, the inventors have injected water suspended blue pigment particles (d~1 μm) into Carbopol®, creating a continuous square-shaped structure with sub-millimeter cross section. The structure showed no long-term instability over several days. To study the relaxation of structures, the inventors manually injected an aqueous suspension of fluorospheres (d=5 μm) into Carbopol® at a high flow rate, and imaged part of the structure in time-lapse. The high pressure and flow rate appeared to fracture the Carbopol® phase, creating micro-scale channels, but the injected region relaxed marginally and remained stable (FIG. 22). FIG. 22 illustrates: A square outline of particles was extruded (A) with an average cross section of <500 μm (B). A stable linear structure of diameter ~200 mm was generated (C). Manual injection of fluro-spheres created a "fracked" structure (D) that relaxed briefly then stabilized (E). Similar cell structures should remain stable, apart from the influence of cell-generated forces. For many days of cell growth in Carbopol®, the polymer particles must be swelled in cell growth medium. The inventors have made a Carbopol®-cell growth medium mix in which the inventors have grown human aortic endothelial cells for days with no signs of cell death.

Example: Tests of DC-9041: Aqueous-Oil Structures

Figure 23:
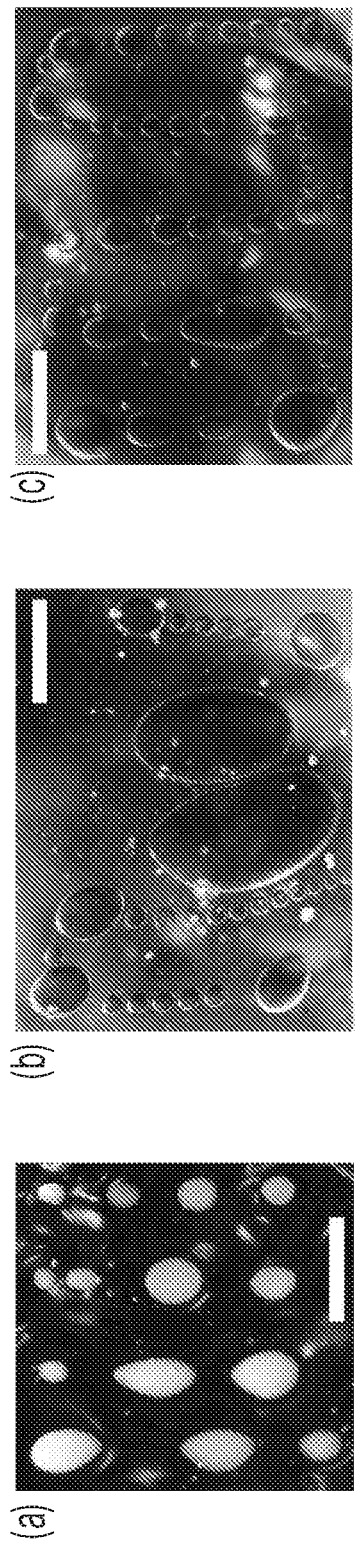
FIG. 23 illustrates droplets extruded into yield stress materials for exemplary experimental study according to some embodiments.

The immiscibility of the cell phase and DC-9041 introduces a significant force: interfacial tension, γ. The extrusion rate, extruder speed, viscosity of fluidized DC-9041, yield stress of solid DC-9041, and γ, all determine the shape and stability of the extruded structure. When the yield stress, $\sigma_y$, is too low, lines cannot be formed; the balance of γ and $\sigma_y$ causes large droplets to remain irregularly shaped while small droplets become spherical. When $\sigma_y$ is large, and the extrusion rate and extruder speed are high, narrow lines can be formed (d<300 μm). Intersections of narrow lines are stable, and fine features can be extruded with separation distances as small as the stable feature size. Tests using cell growth medium perform better than aqueous suspensions of dye or particles (FIG. 23). FIG. 23 illustrates: (A) Small, linear features are unstable in low-yield stress DC-9041; surface tension drives small drops to spherical shapes; large drops remain elongated. (B,C) At intermediate yield stresses smaller drops are generated and intermediate sized drops remain elongated. (D) At high yield stresses, perfect crossed lines are generated with diameters of ~250 μm. (E) At high yields stresses, two right angles can be drawn stably with a separation distance of <100 μm at the corners. Scalebars: 3 mm.

Example: Tests of Cells in DC-9041

Figure 24:
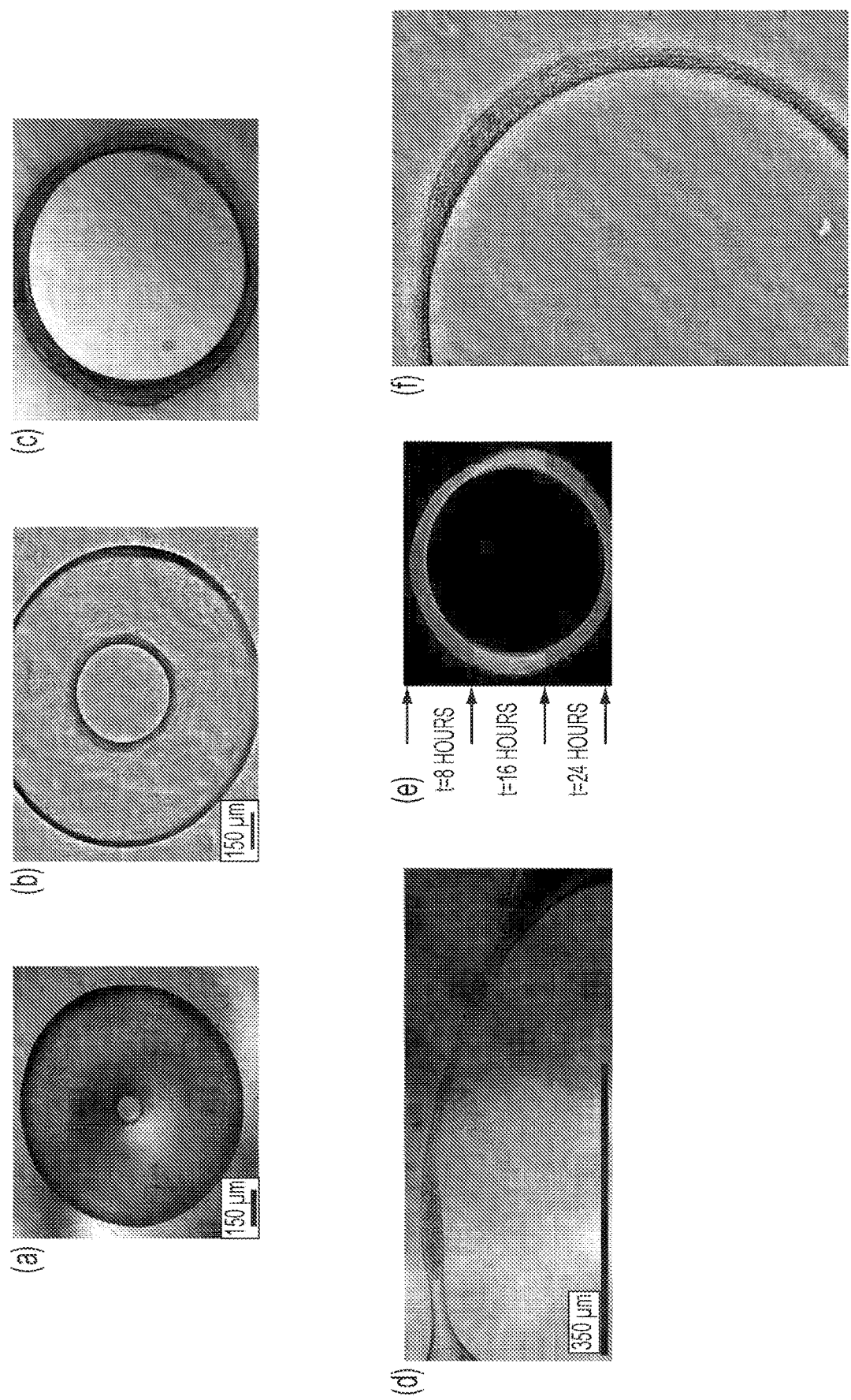
FIG. 24 illustrates cell interaction with extruded droplets for exemplary experimental study according to some embodiments.

Toroid structures containing MDCK epithelial cells were extruded into the DC-9041 at low densities. Cells settled to the bottom of the toroid and appeared to form a continuous band through cell-cell cohesion, contracting inward and squeezing the inner surface. Cells appeared to take on a spread-out, contractile-like morphology similar to cells on surfaces optimized for cell culture. Over time, the inner radius of the toroid decreased. The decrease in radius may be generated by collective cell tension originating in cytoskeletal contraction. Asymmetric collapse of a toroid squeezed the cell band into a narrow tube; this type of failure may be driven by cytoskeleton tension. Performing digital image correlation (PIV) on the time-lapse movies revealed significant equatorial collective motion, suggesting that a net vorticity emerges in this circular geometry (FIG. 24). FIG. 24 illustrates: (A) Sparse cells settle to the bottom surface of a toroidal drop. (B) In the absence of matrix, cells cohere forming a band and contracting around the inner surface. (C) A high magnification image of cells in panel B. (D) A toroidal shape created in a low yield stress material collapses asymmetrically, squeezing a group of cells down to ~30 μm cross section. (E) In a stable toroid from panels B and C, cells contract the inner surface over time. (F) PIV on cells from panels B, C, and E shows a net vorticity.

Exemplary Application

Range of Possible Structures

To facilitate efficient studies of complex structures, a wide range of simple structures may be created, like linear and curved tubes. The relationship between tube diameter and extrusion rate may be experimentally determined, creating a data "recipe book" to guide later studies of complex structures. To harness the versatility of yield stress materials, the limits of structural stability may be found in materials over a wide range of yield stresses. Yield stress is varied by dilution with water for Carbopol, and with PDMS oil for DC-9041. Tuning the yield stress may be crucial for the quantitative studies of cell forces, below. Stress propagation is sensitive to the size and speed of the extrusion nozzle, which may be varied to maximize the range of possible structures.

Fluorescent Markers for Direct Observation of Motion

Figure 25:
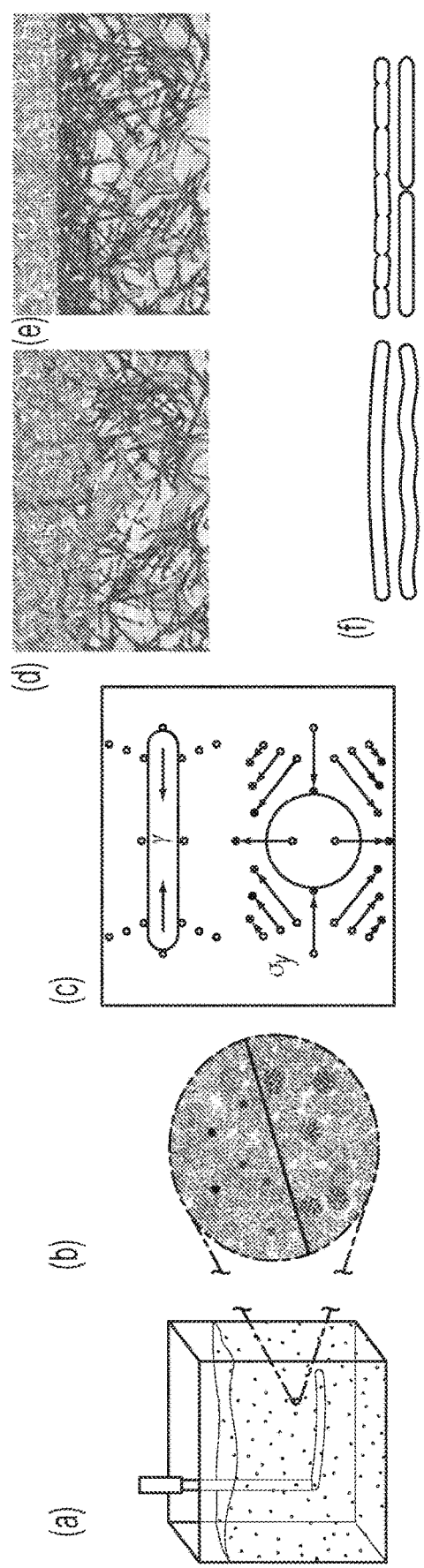
FIG. 25 illustrates stress computation techniques for exemplary experimental study according to some embodiments.

As unstable structures collapse, and stable structures generate or relax stress, the surrounding yield stress material may displace. Markers may be dispersed throughout the yield stress materials to enable measurement of local displacements. In Carbopol®, fluorescent beads may be mixed in with the microgel particles; large beads (~1 μm) may be trapped between microgels. Alternatively, if smaller beads are required, or bead diffusion occurs, the microgels may be swelled in a strong base (NaOH), allowing fluorescent nanoparticles (~10 nm) to diffuse into the polymer mesh, and then returning the system to neutral pH, shrinking the gels and trapping the nanoparticles. Similar approaches may be taken with DC-9041 fluid. The inventors have dispersed aqueous fluorospheres in PDMS, with a step-wise solvent exchange from water to ethanol to methanol. Beads suspended in methanol can be extremely well dispersed in viscous PDMS fluids by sonication with a high-powered probe sonicator. If swelling the DC-9041 micro-gels is necessary to trap particles in the polymer mesh, hexane may be used as a swelling agent, and PMMA nano-particles may be used because of their stability in hexane. 3D tracking of fluorescent particles may be performed with confocal microscopy to measure displacements; with sufficient data, strain fields can be computed. The material properties of the yield stress materials described herein with bulk rheology may be studied, and the known bulk rheological properties of the yield stress materials may be used to compute stresses (FIG. 25A-C). FIG. 25A-C illustrate: (A,B) To develop optical force measuring methods, fluorescent markers are embedded in the YSMs. (C) As cell structures move, the surrounding YSM are strained. If the material properties of the YSM are known in detail, strains may be converted to stresses in well-defined cases.

Cell/Support Interface in Simple Structures

The inventors' data show the compatibility of Carbopol® and DC-9041 with cultured cells. The surprising "fracking" behavior of Carbopol® during extrusion suggests that when mixtures of cells and collagen precursor are used, the collagen matrix may interdigitate with open channels near the Carbopol® surface, creating entanglements (FIG. 25D). FIG. 25D illustrates how cell/ECM structures formed in Carbopol® may have entanglements at the interface. By contrast, the immiscibility between the cell growth mixture and DC-9041 fluid may create smooth surfaces due to interfacial tension. Collagen precursor may adhere to this interface, forming connections to the bulk matrix; non-specific adhesion of collagen to PDMS is routinely used for cell adhesion on flat surfaces (FIG. 25E). FIG. 25E illustrates how cell/ECM structures formed in DC-9041 may have smooth interfaces. In both cases, the total adhesion energy may scale with surface area, yet the total energy cells generate with contractile stress scales with volume, and possibly cell density. Therefore, the adhesion and detachment of cell-matrix assemblies may be studied, as a function of volume and cell density, in simple structures like spheres and cylinders. Cell contraction may also be manipulated using drugs like blebbistatin and thrombin. By carrying out time-lapse measurements over long times the effects of cell-density can be determined; cell density steadily increases over time due to proliferation. The collagen network can be imaged using confocal-reflectance or by fluorescently labeling collagen with rhodamine, using EDC-NHS chemistry. Cells can be identified using whole-cell dyes (CMFDA), nuclear stains (Hoechst), or transfection approaches.

Yield Stress and Cell Forces

The several energy scales in the cell/support system can compete to give rise to unique instabilities. In a slender cylinder, if cells align axially, cell generated tension may take the place of external forces in classic Euler buckling, causing a long-wavelength bend. If the support material lends lateral reinforcement, a short-wavelength buckle may arise; the wavelength may be controlled by the modulus of the support material and the bending elasticity of the cell-collagen cylinder. If one of these modes arises at low stresses, but cell generated stress rises above the yield stress ($\sim\frac{1}{3}$ of the shear modulus), the growth of one of these ground-state modes may grow uncontrollably, or the instability may vanish because the support material is no longer solid. Alternatively, if cells generate shear stress gradients in the cylinder, and the yield stress material fluidizes, interfacial oscillations may arise analogous to those of the Rayleigh-Plateau instability. Growth of Rayleigh-Plateau-like modes could cause tube-break up, determining a maximum length-scale for stable structures, set by cell generated stress and interfacial tension between the two phases (FIG. 25F). FIG. 25F illustrates how, depending on the dominating forces in the structures, several types of instabilities may arise. To explore these cell-generated instabilities, linear structures with a range of diameters and lengths may be created, supported in both types of yield stress material, prepared with a wide range of yield stresses. If the instability can be categorized, the type of emergent force can be determined (surface tension, shear stress, etc). In the ideal case, a single, unknown, cell-generated force is competing with a known force in the passive material, enabling a measurement of the cell-generated force.

Collective Cell Dynamics with Topological Constraints

Figure 26:
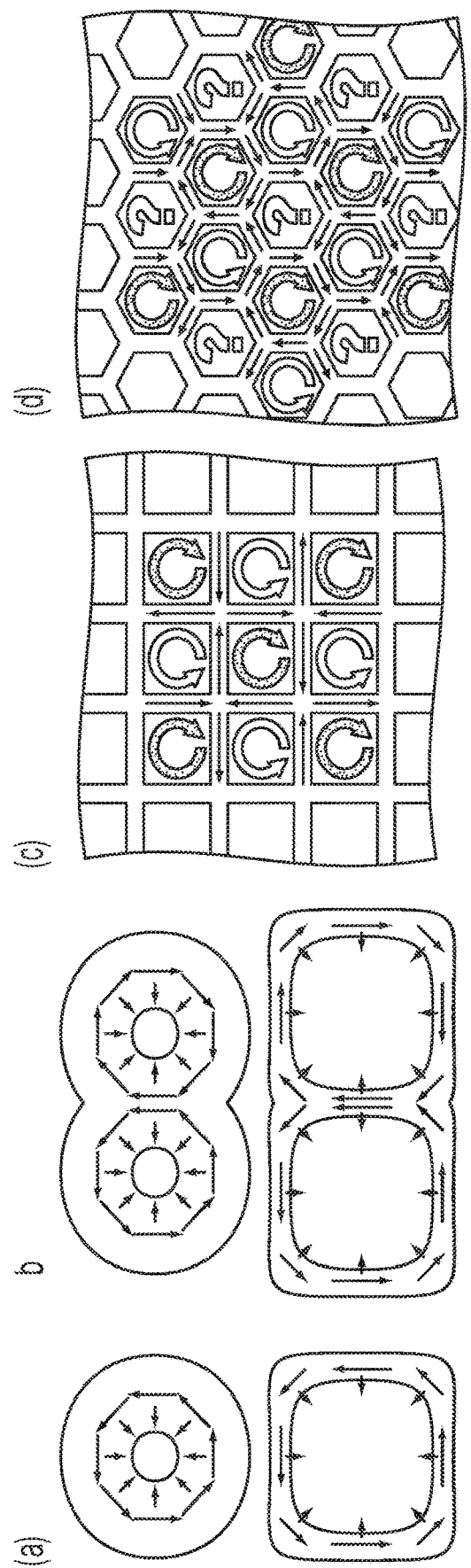
FIG. 26 illustrates cell interaction with various curvatures for exemplary experimental study according to some embodiments.

The inventors' data demonstrated the importance of topology: in a genus=1 object, cells form a large, stable unit with no ECM, and migrate collectively. These studies may be continued in circular and square volumes to explore many questions (FIG. 26A). FIG. 26A illustrates how cells circulate in genus=1 structures, and cells migrate toward surfaces of preferred mean or Gaussian curvature. Structure size may be varied to explore the relationship between cell-generated forces and curvature; tension can be estimated by measuring contraction of the inner surface. The volumes may be filled with ECM so that cells can migrate to all surfaces, testing whether cells prefer specific combinations of mean and Gaussian curvature that exist in loop structures. Different cell types may be compared, like epithelial, endothelial, and fibroblast cells to explore the relationship between cells from different tissues and different types of curvature. Cells may be sensitive to topology and mean or Gaussian curvature, providing a new class of cell guidance for many applications.

Vorticity in Loops

The large-scale correlation length observed in measurements of collective cell motion in toroids, and the apparent vorticity, raise a question of whether the size of the loop can control a transition between collective circulation and random motion. Collective migration may be explored in loop structures of varying size to search for such a transition. Small loops may circulate, and when the circumference of a loop exceeds a natural correlation length, controlled by individual cell dynamics, random motion may occur. Controlled collective circulation may be used to study pairs of loops to look for coordination over larger scales (FIG. 26B). FIG. 26B illustrates how cooperative circulation arises in pairs of loops, coupled by shear stress. Neighboring loops may coordinate in opposite directions, minimizing shear-stress at the interface. These studies may be performed in loops without ECM and in loops filled with ECM. Curvature may confound the effect; smaller loops may promote collective circulation, but their high curvature may inhibit migration.

A Lattice to Tile Space and Collective Migration Patterns

Coordinating cell migration in proximal loops, even weakly, may allow repeating the pattern on a large lattice to amplify coordination, analogous to size-dependent effects in magnetism. Analogies between collective cell migration and collective effects in magnetic spin systems may be explored by creating multi-cellular lattices of varying size and symmetry. Coordinated cell vortices may be analogous to anti-ferromagnetic spins; neighboring cell vortices may rotate in opposite directions, coupled by shear stress. Arranging cells on a lattice with square symmetry may generate an anti-ferromagnetic phase; all of space can be tiled by counter-rotating vortices. By contrast, by arranging cells on a lattice with hexagonal symmetry (technically a honeycomb lattice in this case), geometric frustration may suppress macroscopic coordination of rotating vortices. The hexagonal phase may be analogous to a spin glass. Shear stress coupling may not be the only potential driving force for these phases; cell flux through nodes may be very different on the two lattices. On a square lattice each node may have two inputs and two outputs; on a hexagonal lattice each node may have either one input and two outputs, or vice-versa (FIG. 26C,D). FIG. 26C,D illustrates: (C) Cells on a square lattice form an anti-ferromagnetic phase. (D) Cells on a hexagonal (honeycomb) lattice form a spin-glass. Arrows indicate cell migration direction. Yellow arrows indicate cooperative paths; red arrows indicate frustrated paths. The use of symmetry as a principle to control collective motion may represent a new class of cell guidance.

Dimensionality in Collective Phase Stability

In both equilibrium and non-equilibrium systems, like the cell structures described herein, the degree of ordering, determined by competition between random fluctuations and the forces that promote order, may depend on the system dimensionality. To explore the dependence of order on system dimension, 1D, 2D, and 3D lattices may be created with identical features and compare spatio-temporal correlations in cell migration between the three. True long-range order may not be present in any system, however, 2D order may be longer ranged than 1D order, in analogy to the Ladau-Pierls instability. Additionally, there may be a major difference between the anti-ferromagnet and cell-vorticity coordination in 3D. All of space can be tiled with anti-parallel spins on a cubic lattice because all spins can align along a single axis. By contrast, the "spin" direction in a rotating vortex on a cubic lattice is normal to the face of the cube on which it sits. It may be impossible to tile all of space with these spins, and 3D geometric frustration may occur.

Issues and Alternative Approaches

Insufficient adhesion between cell structures and the YSM may result in delamination at the interface. This can be mitigated by chemical modification of the YSM material; Carbopol® is an acrylate based polymer, and covalent attachment of proteins is straight-forward. Alternatively, the collapse of a variety of delaminated structures may provide equally valuable insight into collective cell behavior in complex structures.

Additional Exemplary Implementation and Uses of Embodiments

Figure 27:
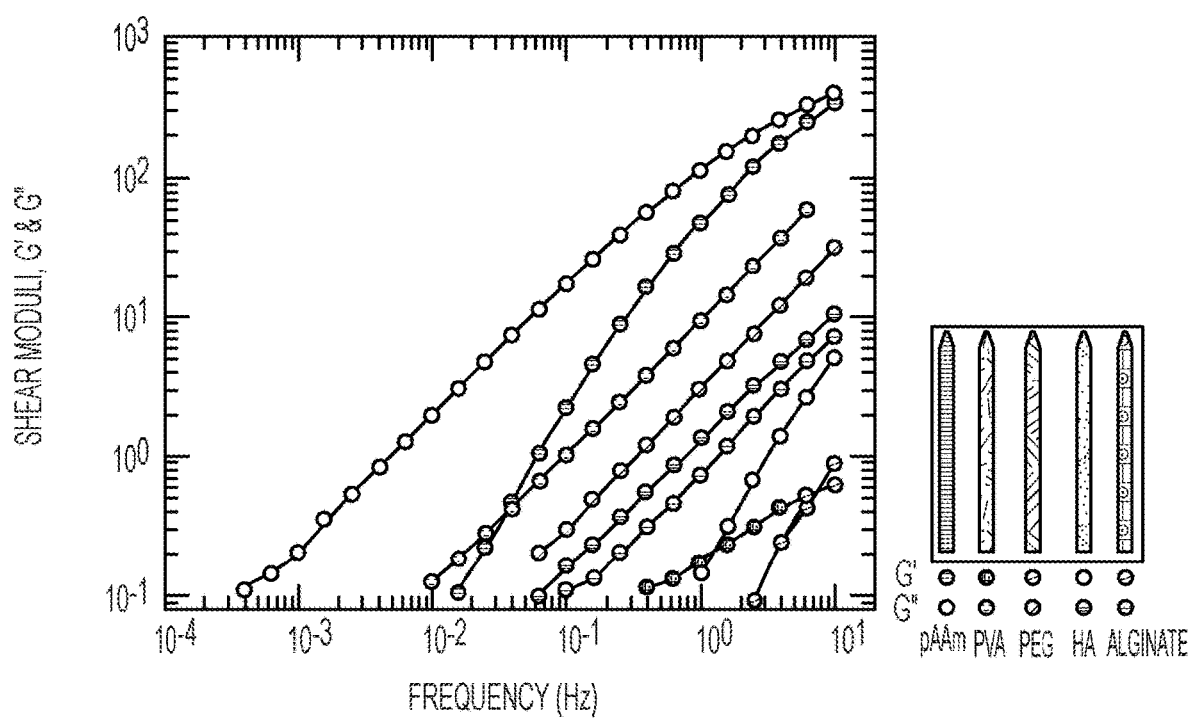
FIG. 27 illustrates exemplary writing with rheologically disparate materials according to some embodiments.

Writing in a granular gel medium provides precision and stability that is not governed by the rheological behaviour of the writing medium. As evidence of this we produced a set of closed-shell structures made from PVA, polyacrylamide, polyethylene glycol, hyaluronic acid, and sodium alginate, which have viscous moduli spanning a range of an order of magnitude above and below the characteristic yield stress of the granular gel (FIG. 27).

Figure 28:
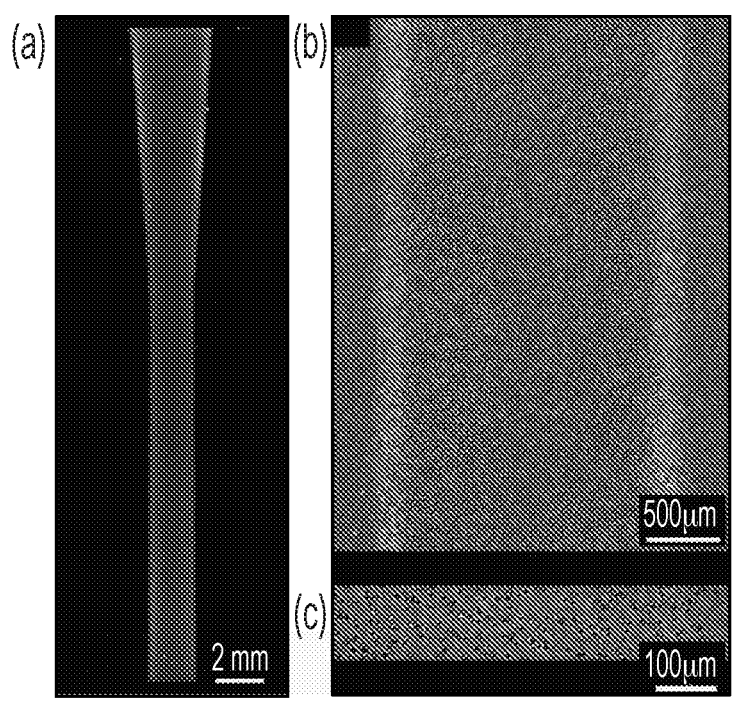
FIG. 28 illustrates exemplary blood flow through hollow hydrogel tubes according to some embodiments.

A PVA formulation used in some embodiments is called nelfilcon A, a biocompatible polymer system used to make contact lenses. By increasing the injection rate during writing, a thicker (~300 μm wall thickness) structure was made and removed from the GGM. When placed in a water bath it can be seen to bend and undulate as water flows past its numerous branches. A different set of hollow tubes were generated to demonstrate the ability to produce functional fluidic channels, through which we flowed bovine blood driven by a syringe pump (FIG. 20e, FIG. 28).

Figure 29:
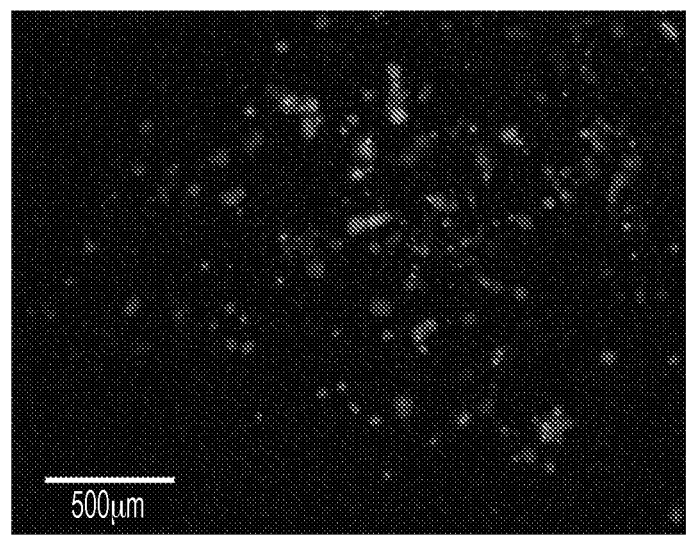
FIG. 29 illustrates exemplary cell viability assays according to some embodiments.

It is possible to both write and grow living tissue cells in a granular gel culture medium, which is prepared by using cell growth media as a solvent. Observations of cell migration, division, and viability, demonstrate the potential of the GGM as a suitable medium for 3D cell culture (FIG. 29).

Figure 30:
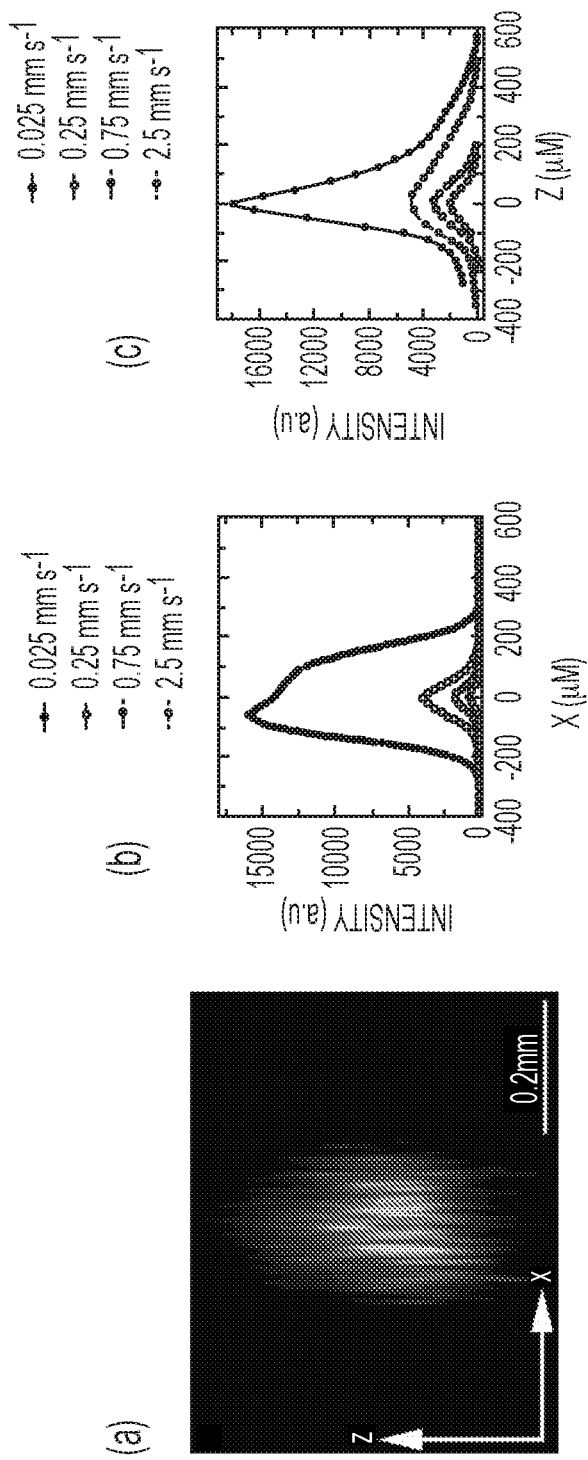
FIG. 30 illustrates exemplary tip speed, injection rate, and feature width of 3D printing according to some embodiments.
Figure 31:
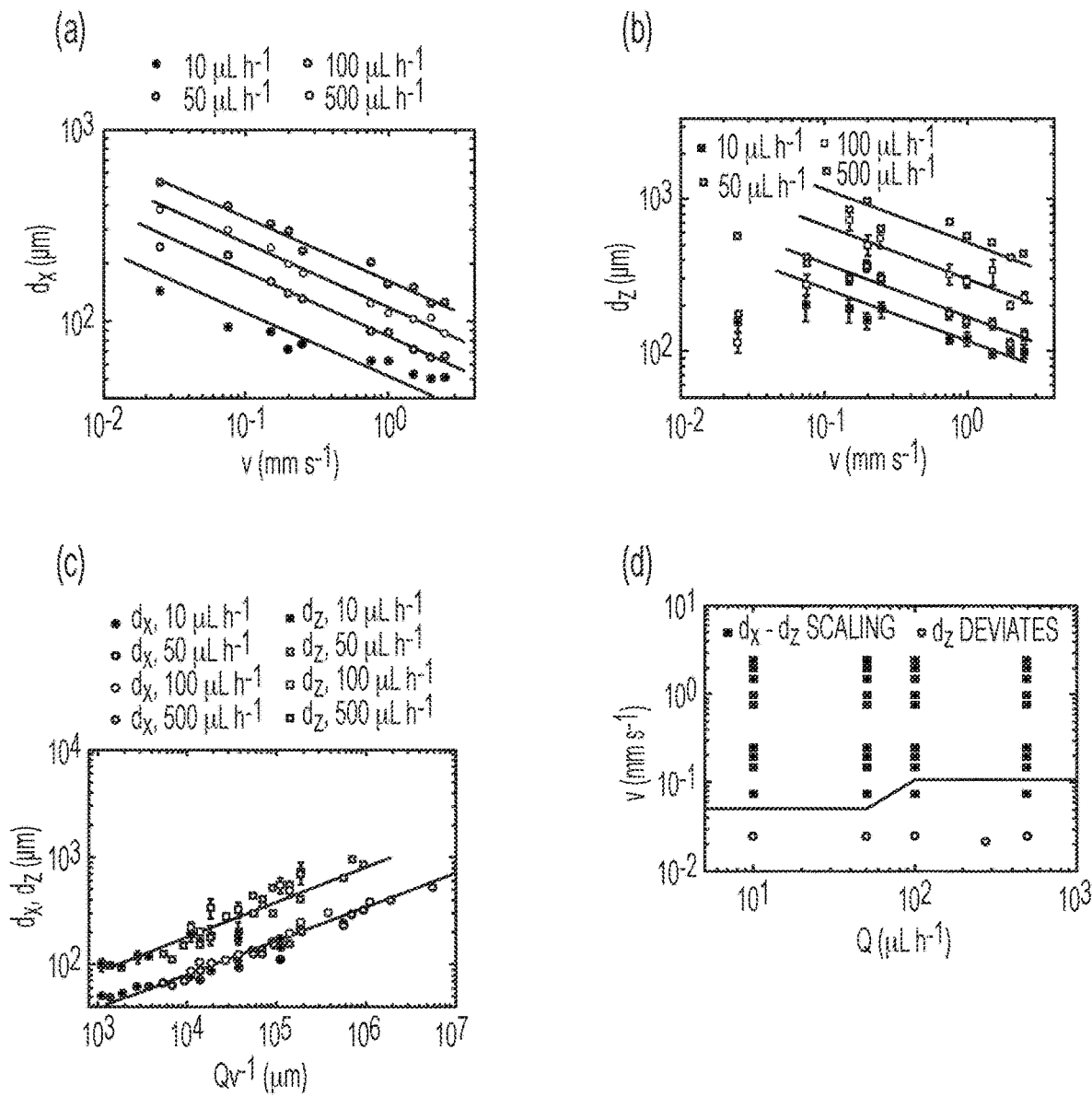
FIG. 31 illustrates exemplary scaling and limits of feature width of 3D printing according to some embodiments.

The limits on size, speed, precision and materials have yet to be fully defined for writing structures in granular gels (FIGS. 30, 31). However, this simple medium removes numerous technical barriers to the creation of finely detailed multi-dimensional structures by using the graceful behaviour around yielding to trap and hold delicate features within a jammed gel made from soft, athermal particles. The remarkable properties of the soft GGM provide stability and versatility within an easy framework that can be immediately integrated into existing platforms across numerous areas from flexible electronics to biology and medicine.

Exemplary Methods

GGM Preparation

To prepare the soft GGM, 0.2% (w/v) Carbopol® ETD 2020 polymer (Lubrizol Co.) may be suspended in ultrapure water (18.2 MΩ-cm) and 0.01 N NaOH. For writing with photocrosslinkable polymer solution, 0.05% (w/v) of Irgacure photoinitiator (Sigma Aldrich) may be mixed with the Carbopol® GGM. When writing with cells, the gel medium may be prepared with the Endothelial Basal Media (EBM-2) supplemented with vascular growth factors and antibiotics. Powdered Carbopol® (0.7% w/v) may be dispersed into EBM-2 at 37° C. under sterile conditions and the gel medium may be incubated at 37° C. and 5% $CO_2$ for 24 hours before writing. Other Carbopol® concentrations have been explored (0.05%-1%). For writing PDMS structures, Dow Corning 9041 silicone elastomer may be is diluted by 10% (w/w) with silicone oil and may be used as the GGM. All types of gel medium are homogenized by mixing at 3000 rpm in a speed mixer followed by centrifugation to remove gas bubbles.

Writing Medium Preparation

Fluorescent polystyrene microspheres (Thermo Scientific) with 1 μm diameter may be prepared at a concentration of 0.1% (w/v) for writing, making the writing medium fluorescent and turbid. When writing water-based polymer structures, the microspheres may be dispersed in an aqueous solution of photocrosslinkable polyvinyl alcohol (nelfilcon A, provided by Alcon laboratories). After mixing, the polymer concentration may be approximately 27% (w/v) and the microsphere concentration may be 0.1% (w/v). Polyethylene glycol samples (M.W. 35,000 Da) may be prepared at a 27% concentration (w/v) in ultrapure water. Polyacrylamide may be prepared by polymerizing acrylamide monomer (15% w/v) with tetramethylethylenediamine (0.3% v/v) and ammonium persulfate (0.3% w/v) in ultrapure water, then mixing with fluorospheres to a final polymer concentration of 14.3% (w/v). Hyaluronic acid (M.W. 800,000 Da) may be prepared at a concentration of 0.95% (w/v) in ultrapure water with added fluorospheres. Sodium alginate may be prepared at a concentration of 2.4% (w/v) in ultrapure water with added fluorospheres. Sylgard 184 (Dow-Corning) may be used for writing PDMS structures. The PDMS elastomer base may be mixed with curing agent at a 10:1 weight ratio. To disperse fluorospheres in the PDMS, a solvent exchange from water to methanol may be performed. A concentrated drop of methanol-microsphere suspension may be homogeneously dispersed in PDMS using a speed mixer at a final concentration of approximately 0.1% (w/v). Structures printed with photocrosslinkable PVA may be cured with a 100 mW/cm$^2$ UV lamp. The Carbopol® gel medium may be washed with water to remove the cured structure.

Writing in the GGM

The three-dimensional writing instrument may be composed of a syringe pump for injecting material into the GGM, and three linear translation stages (M-403.2DG from Physik Instrumente) that provide relative motion to the injection tip. Injection tips with an inner diameter of 50 μm may be made out of glass microcapillaries (1 mm inner diameter) using a pipette puller (David Kopf Instruments). While printing cells, injection tips of inner diameter 200 μm may be used. To reduce wetting of written material to the injection tip, the glass tips may be given a hydrophobic surface coating of triethoxy (octyl) silane for printing water based polymer solution and a hydrophilic surface coating of (3-aminopropyl) triethoxysilane for printing PDMS structures. The syringe pump and the stages may be coupled together and programmed with MATLAB to inject the writing material at the chosen flow rate while tracing out a path in space. Surface coordinates of structures may be generated from analytical 3D functions in the form of closely packed helices. The tangential speed of the microcapillary may be kept constant while writing into the GGM.

Cell Culture for Writing in the GGM

Human aortic endothelial cells (HAEC) may be cultured in EBM-2, supplemented with 2% fetal bovine serum and vascular endothelial growth factor (Lonza). HAECs may be incubated at 37° C. in 5% $CO_2$ and grown to confluence in six-well plates. Cells may be fluorescently dyed by treating with 2 µM 5-chloromethylfluorescein diacetate (CMFDA) in serum-free EBM-2 and 0.15% DMSO for 30 minutes. CMFDA may be used for fluorescence imaging as well as live cell detection; when cells lyse they lose fluorescence because the dye may be released. After dyeing, cells may be immediately washed with phosphate buffer saline, trypsinized, and harvested. Approximately, $10^6$ cells may be then concentrated and re-suspended in 0.15 mL of EBM-2, and immediately loaded into a syringe. The writing process may be performed under sterile conditions at 37° C. We observe viability after printing and for cells grown in the medium for several days. Mass transport limitations within the granular growth media may be unlikely to occur under the conditions explored here for several reasons. The GGM used for cell culture may be 99.3% cell growth medium by mass. In dilute hydrogels, diffusion of small molecules may not be significantly impeded relative to free diffusion in water. The vascular structures written into the GGM may have a huge surface-area to volume ratio, and no cell may be more than about 150 µm away from a free surface. Cell viability assays may be performed using ReadyProbes® Cell Viability Imaging Kit from Life Technologies.

Photography and Microscopy

Photographs are taken using a Nikon D3X camera under bright field and UV illumination. Videos are recorded using a Nikon 3100 camera or an Imaging Source DMK-21AU04 camera under white light illumination. Micrographs are taken with a Nikon Eclipse Ti-E Microscope with a C2 confocal scanning system. All image and video processing is done using Image-J.

Rheological Characterization

Measurements may be performed on a Malvern Kinexus rheometer in cone-plate geometry. Sample temperature may be stabilized and maintained at 25° C.

Additional Discussion of Drawings

Figure 32:
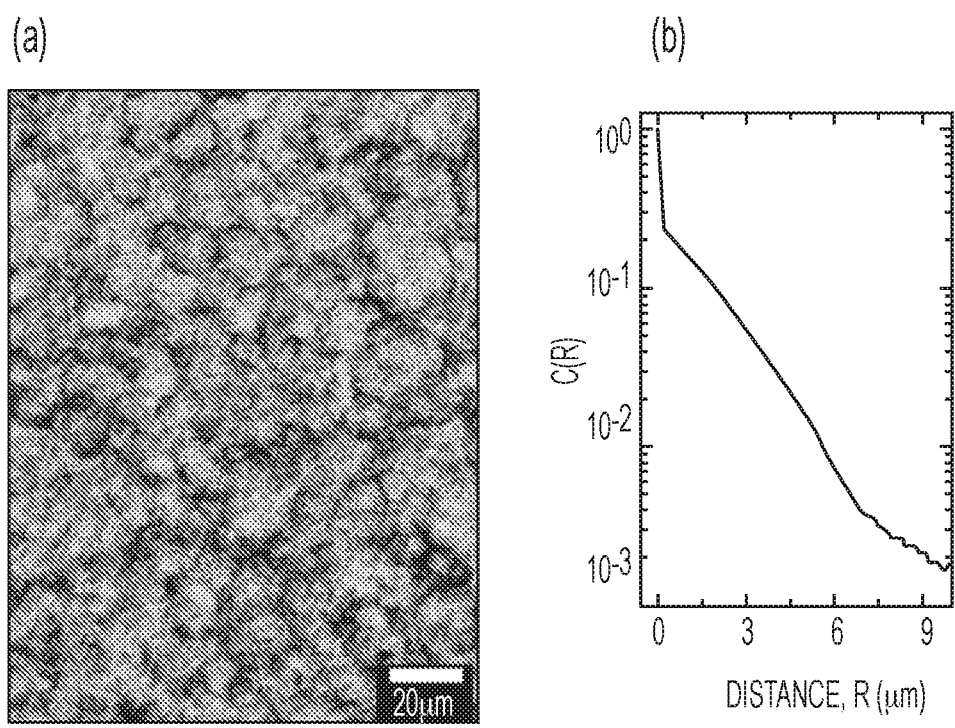
FIG. 32 illustrates exemplary granule size of a granular gel medium according to some embodiments.

FIG. 32 illustrates exemplary granule size of a granular gel medium according to some embodiments: a) Confocal microscopy cross-section of GGM in which the granules were previously swelled and filled with 20 nm fluorospheres, then concentrated again to 0.2% (w/v). b) Intensity-intensity autocorrelation function shows a broad shoulder with a kink at 7 µm, indicating the approximate particle size.

Figure 33:
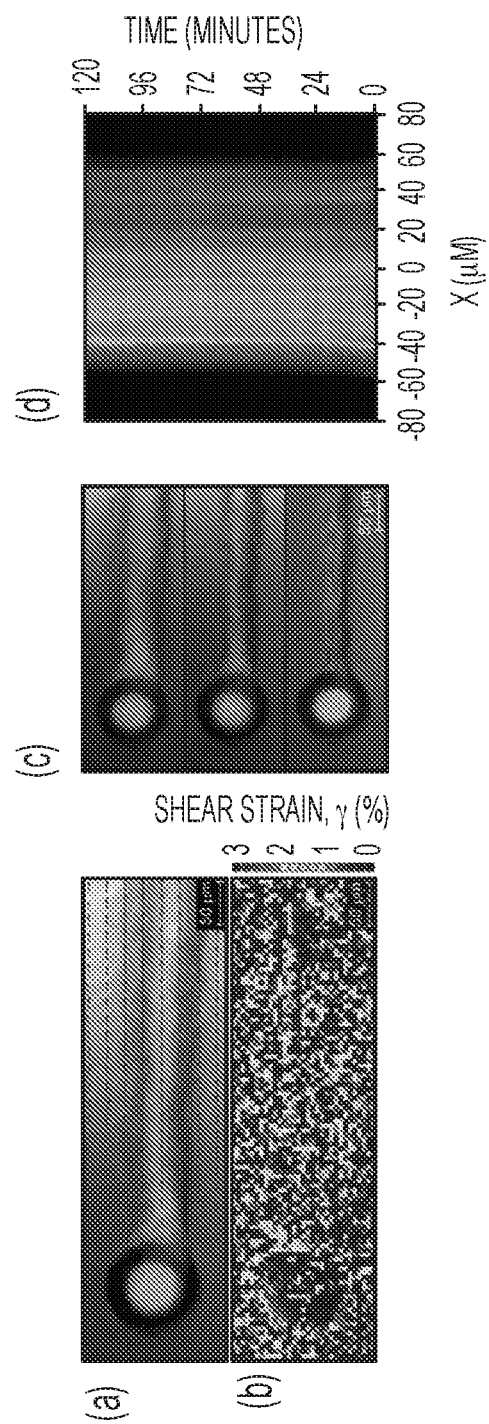
FIG. 33 illustrates microscopic imaging of writing in a granular gel medium according to some embodiments.

FIG. 33 illustrates exemplary microscopic imaging of writing in a granular gel medium according to some embodiments: a) A velocity field is measured using PIV from video captured while writing at a flow rate of approximately 10 µL $h^{-1}$ and a tip speed of 0.07 mm $s^{-1}$. The GGM concentration is 0.2% (w/v) and the written material is a mixture of fluorescent microspheres and PVA polymer. b) The instantaneous shear strain amplitude, computed from the velocity field, shows very little strain throughout the region imaged, indicating minimal disturbance of the surrounding GGM and extremely rapid solidification after fluidization. c) Decreasing feature width may be observed with increasing tip speed (speed increasing from top to bottom). d) Fluorescence images were collected in time-lapse for two hours immediately after the cessation of writing. An intensity slice, taken across the feature is shown evolving in time by a kymograph. A short relaxation is observed for the first 10 minutes, during which the GGM may squeeze inward against the written feature. The vertical striations correspond to groups of fluorescent particles remaining in the same location throughout the time-lapse, trapped by the GGM.

FIG. 30 illustrates exemplary tip speed, injection rate, and feature width of 3D printing according to some embodiments: a) To establish protocols for writing in the GGM, linear features were drawn and measured using different combinations of tip speed and injection rate. Continuous horizontal lines were drawn with tip translation speeds between 0.025 mm $s^{-1}$ and 2.5 mm $s^{-1}$, and with injection flow rates between 10 µL $h^{-1}$ and 500 µL $h^{-1}$. A microscopic dispersion of 1 µm fluorescent spheres in water was used as the writing medium. To measure the feature size for all combinations of tip speed and injection rate, z-stacks were collected with fluorescence microscopy. A maximum intensity projection in the x-z plane shows a cross-section of a written line. The re-constructed x-z projection was stretched to a true spatial aspect ratio, so features appear stretched along the z direction due to low sampling density of z-slices. (Displayed with a false colour LUT to highlight edges). b,c) Intensity projections onto the x and z axes are used to quantify the feature sizes along the vertical and lateral writing directions. Example profiles at different tip speeds and a fixed injection rate, Q=50 µL $h^{-1}$, are shown. Intensity profiles show that feature width along both the x and z directions may decrease with increasing tip speed.

FIG. 31 illustrates exemplary scaling and limits of feature width of 3D printing according to some embodiments: a,b) Feature widths $d_x$ and $d_z$ show smooth variation with the injecting tip speed, v over most of the range of speeds tested. Errorbars are 95% confidence intervals of the full-width at half-maximum parameter in Gaussian functions fit to intensity profiles. These trends in feature size versus tip speed may systematically increase with increasing injection rate, Q. c) When plotting feature size versus the ratio $Q v^{-1}$, the $d_x$ and $d_z$ data collapse onto universal scaling curves, $d=(\lambda Q v^{-1})^{1/3}$, where the scaling parameter $\lambda$ is found to be about 50 µm for the $D_x$ data and about 900 µm for the $D_z$ data. This scaling law can be immediately used to guide the design process for writing in GGM, while deeper investigation is carried out to reveal the physical details underlying the scaling between features size and writing parameters. These data are the same as provided herein, plotted here with a different horizontal axis for clarity. d) These simple scaling laws show that $d_z$ is proportional to $d_x$ over most of the Q-v space explored for writing, allowing the predictable generation of features in both directions. When the tip moves very slowly, however, $d_z$ may deviate and not scale proportionally with $d_x$. Here we plot a phase-diagram in Q-v space to identify the boundary between these two regimes of writing in the GGM.

Figure 34:
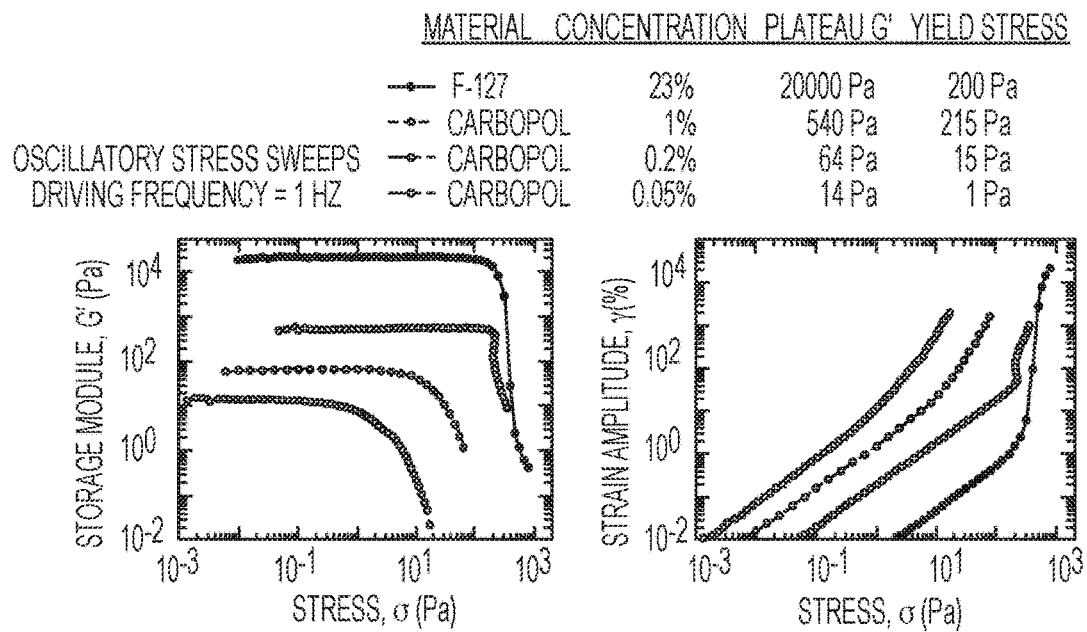
FIG. 34 illustrates exemplary rheological characterization of a granular gel medium according to some embodiments.
Figure 34:
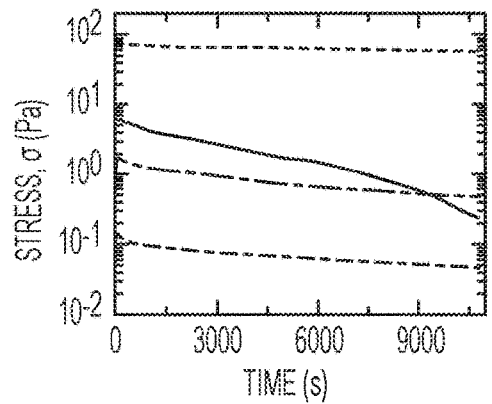
Figure 34:
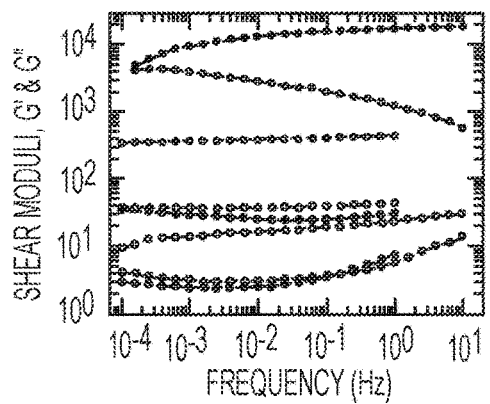

FIG. 34 illustrates exemplary rheological characterization of a granular gel medium according to some embodiments: The GGM was prepared at three different Carbopol® concentrations as described in Methods. To provide a point of comparison, we also prepared samples of F-127 pluronic gel, which has been used previously as an embedding medium for 3D printing. a) Stress-sweeps performed in oscillatory shear were used to measure the low-stress plateau modulus, G', and the yield stress of each sample. We identify the approximate yield stress with the point where G' falls below ½ the plateau value. The lower concentration GGM samples exhibit a very slow, smooth transition to yielding with increased stress, while the high concentration GGM and F-127 gel transition abruptly. b) The same transition can be observed when plotting the strain as a function of the stress; these tests are stress controlled, so a rapid jump in strain show that the applied stress level results in a dramatic increase in oscillation amplitude. c) Stress relaxation measurements highlight a major difference between the GGM and the f-127 gel. At low strains, the GGM gels relax very little stress over long times, indicating low levels of microscopic rearrangement. The F-127 gel showed a persistent reduction in stress throughout the $10^4$ second test. This difference may be associated with the granular nature of the gels, versus the thermal nature of the nano-scale micelles comprising the F-127 system. d) To explore the degree of fluid-like behaviour in the GGM, frequency sweeps were performed at low applied strains. The granular gel systems all exhibited fairly flat responses, with G' and G" remaining separated across the spectrum, behaving almost like a linear solid with damping. By contrast, the F-127 frequency sweep resembled that of a Maxwell-fluid, suggesting that its solid-like stability is associated with kinetically impeded thermal motion, consistent with its stress-relaxation behaviour. These rheological measurements highlight the fundamental properties of soft granular gels that provide great practical versatility for three dimensional writing, enabling the creation of the wide diversity of structures reported here.

FIG. 27 illustrates exemplary writing with rheologically disparate materials according to some embodiments: We tested the sensitivity of the granular gel medium to the rheological properties of writing materials by preparing solutions of several polymers at different concentrations and writing the same structure at the same flow rate (10 µL h$^{-1}$), tip speed (2.5 mm s$^{-1}$), and granular gel concentration (0.2% w/v). Hollow-shell scale models of crayons 2.78 cm in length (⅓ scale) and approximately 200 µm wall thickness were created from solutions of polyacrylamide (14.3% w/v), PVA (27% w/v), polyethylene glycol (27% w/v), hyaluronic acid (0.95% w/v), and sodium alginate (2.4% w/v). Fluorescent microspheres were added to the polymer solutions to enhance contrast for imaging under a combination of white light and UV illumination. Oscillatory rheological measurements were performed on the polymer solutions at 1% strain. The written polymer materials were found to exhibit widely varying viscoelasticity. For example, at a frequency of 1 Hz, the viscous modulus (G") of polyacrylamide was found to be 113 Pa, while the viscous modulus of alginate was found to be 0.75 Pa, with the other materials falling between the two. These viscous moduli fall approximately an order of magnitude above and below the yield stress of 0.2% GGM, 15 Pa. Writing in the GGM thus provides a broad range of freedom for materials selection without the need for optimization when changing materials, enabling the rapid creation of spatially heterogeneous structures from different materials like tissue-mimicking biomaterials or layered systems of multiple cell types.

FIG. 28 illustrates a demonstration that techniques described herein may be used in connection with wound repair. In particular, FIG. 28 illustrates exemplary blood flow through hollow hydrogel tubes according to some embodiments: a) 2 mm diameter fluidic channels were made by writing thin shelled tube structures from mixtures of PVA and fluorospheres, UV crosslinking the PVA, then removing the granular gel from within the tubes by a combination of fluid flow and physical agitation with a glass micro-capillary. After emptying the channels, bovine blood diluted with phosphate buffered saline was driven through the tubes using a syringe pump. b) The walls were imaged with microscopy before emptying the channels (cyan colour), and later overlaid seamlessly with images of the blood filled channel (grayscale intensities). Inside of the channel, the blood cells are seen as small black and white speckles, and outside of the channel the granular gel particles are seen as grainy grey objects. c) At higher magnification individual blood cells can be seen inside of the channel.

FIG. 29 illustrates exemplary cell viability assays according to some embodiments: Human aortic endothelial cells were injected into the granular gel medium permeated with EBM-2 cell growth media, then kept in a sterile incubator at 37° C. and 5% $CO_2$. At 24 hour intervals, cells were removed from the incubator and imaged in fluorescence microscopy. A representative micrograph of cells on day 2 is shown, where green fluorescent cells are alive, and cells with both green and red fluorescence are dead. We find 92% viability on day 1 (N=97), 84% on day 2 (N=146), 80% on day 3 (N=652). The optimal conditions for cell growth in the GGM is expected to vary widely between cell types, and there remain numerous research opportunities in developing preparation methodologies and processes for the precision manufacturing of complex structures containing cells and matrix materials within the granular gel medium.

REFERENCES

The following references are incorporated herein by reference in their entireties:
1. Dimitriou, C. J., R. H. Ewoldt, and G. H. McKinley, *Describing and prescribing the constitutive response of yield stress fluids using large amplitude oscillatory shear stress* (LAOStress). Journal of Rheology, 2013. 57: p. 27.
2. Menut, P., S. Seiffert, J. Sprakel, and D. A. Weitz, *Does size matter? Elasticity of compressed suspensions of colloidal-and granular-scale microgels*. Soft matter, 2012. 8(1): p. 156-164.
3. Moller, P., A. Fall, V. Chikkadi, D. Derks, and D. Bonn, *An attempt to categorize yield stress fluid behaviour*. Philosophical Transactions of the Royal Society A: Mathematical, Physical and Engineering Sciences, 2009. 367 (1909): p. 5139-5155.
4. Møler, P., A. Fall, and D. Bonn, *Origin of apparent viscosity in yield stress fluids below yielding*. EPL (Europhysics Letters), 2009. 87(3): p. 38004.
5. Mattsson, J., H. M. Wyss, A. Fernandez-Nieves, K. Miyazaki, Z. Hu, D. R. Reichman, and D. A. Weitz, *Soft colloids make strong glasses*. Nature, 2009. 462(7269): p. 83-86.
6. Coussot, P., L. Tocquer, C. Lanos, and G. Ovarlez, *Macroscopic vs. local rheology of yield stress fluids*. Journal of non-newtonian fluid mechanics, 2009. 158(1): p. 85-90.
7. Steinberg, M. S., *Does differential adhesion govern self-assembly processes in histogenesis? Equilibrium configurations and the emergence of a hierarchy among populations of embryonic cells*. Journal of Experimental Zoology, 1970. 173(4): p. 395-433.
8. Steinberg, M. S. and L. L. Wiseman, *Do morphogenetic tissue rearrangements require active cell movements? The reversible inhibition of cell sorting and tissue spreading by cytochalasin B*. The Journal of cell biology, 1972. 55(3): p. 606-615.
9. Steinberg, M. S., *Differential adhesion in morphogenesis: a modern view*. Current opinion in genetics & development, 2007. 17(4): p. 281-286.
10. Schötz, E. M., R. D. Burdine, F. Jülicher, M. S. Steinberg, C. P. Heisenberg, and R. A. Foty, *Quantitative differences in tissue surface tension influence zebrafish germ layer positioning*. HFSP journal, 2008. 2(1): p. 42-56.
11. Eastwood, M., D. A. McGrouther, and R. A. Brown, *A culture force monitor for measurement of contraction forces generated in human dermal fibroblast cultures:* evidence for cell-matrix mechanical signalling. Biochimica et Biophysica Acta (BBA)-General Subjects, 1994. 1201(2): p. 186-192.
12. Zaman, M. H., L. M. Trapani, A. L. Sieminski, D. MacKellar, H. Gong, R. D. Kamm, A. Wells, D. A. Lauffenburger, and P. Matsudaira, *Migration of tumor cells in 3D matrices is governed by matrix stiffness along with cell-matrix adhesion and proteolysis.* Proceedings of the National Academy of Sciences, 2006. 103(29): p. 10889-10894.
13. Provenzano, P. P., D. R. Inman, K. W. Eliceiri, S. M. Trier, and P. J. Keely, *Contact guidance mediated three-dimensional cell migration is regulated by Rho/ROCK-dependent matrix reorganization.* Biophysical journal, 2008. 95(11): p. 5374-5384.
14. Kraning-Rush, C. M., S. P. Carey, J. P. Califano, B. N. Smith, and C. A. Reinhart-King, *The role of the cytoskeleton in cellular force generation in 2D and 3D environments.* Physical biology, 2011. 8(1): p. 015009.
15. Lutolf, M., J. Lauer-Fields, H. Schmoekel, A. Metters, F. Weber, G. Fields, and J. Hubbell, *Synthetic matrix metalloproteinase-sensitive hydrogels for the conduction of tissue regeneration: engineering cell-invasion characteristics.* Proceedings of the National Academy of Sciences, 2003. 100(9): p. 5413-5418.
16. Raeber, G., M. Lutolf, and J. Hubbell, *Molecularly engineered PEG hydrogels: a novel model system for proteolytically mediated cell migration.* Biophysical journal, 2005. 89(2): p. 1374-1388.
17. Beningo, K. A., C.-M. Lo, and Y.-L. Wang, *Flexible polyacrylamide substrata for the analysis of mechanical interactions at cell-substratum adhesions.* Methods in cell biology, 2002. 69: p. 325-339.
18. Marshall, A. J., C. A. Irvin, T. Barker, E. H. Sage, K. D. Hauch, And B. D. Ratner, *Biomaterials with tightly controlled pore size that promote vascular in-growth.* Polymer Preprints, American Chemical Society, Division of Polymer Chemistry, 2004. 45(2): p. 100-101.
19. Isenhath, S., Y. Fukano, M. Usui, R. Underwood, C. Irvin, A. Marshall, K. Hauch, B. Ratner, P. Fleckman, and J. Olerud, *A mouse model to evaluate the interface between skin and a percutaneous device.* Journal of Biomedical Materials Research Part A, 2007. 83(4): p. 915-922.
20. Madden, L. R., D. J. Mortisen, E. M. Sussman, S. K. Dupras, J. A. Fugate, J. L. Cuy, K. D. Hauch, M. A. Laflamme, C. E. Murry, and B. D. Ratner, *Proangiogenic scaffolds as functional templates for cardiac tissue engineering.* Proceedings of the National Academy of Sciences, 2010. 107(34): p. 15211-15216.
21. Linnes, M. P., B. D. Ratner, and C. M. Giachelli, *A fibrinogen-based precision microporous scaffold for tissue engineering.* Biomaterials, 2007. 28(35): p. 5298-5306.
22. Ratner, B. D. and S. Atzet, *Hydrogels for healing,* in Hydrogels 2009, Springer. p. 43-51.
23. Barry, R. A., R. F. Shepherd, J. N. Hanson, R. G. Nuzzo, P. Wiltzius, and J. A. Lewis, *Direct-Write Assembly of 3D Hydrogel Scaffolds for Guided Cell Growth.* Advanced Materials, 2009. 21(23): p. 2407-2410.
24. Shepherd, J. N. H., S. T. Parker, R. F. Shepherd, M. U. Gillette, J. A. Lewis, and R. G. Nuzzo, *3D microperiodic hydrogel scaffolds for robust neuronal cultures.* Advanced functional materials, 2011. 21(1): p. 47.
25. Sun, L., S. T. Parker, D. Syoji, X. Wang, J. A. Lewis, and D. L. Kaplan, *Direct-Write Assembly of 3D Silk/Hydroxyapatite Scaffolds for Bone Co-Cultures.* Advanced healthcare materials, 2012. 1(6): p. 729-735.
26. Miller, J. S., K. R. Stevens, M. T. Yang, B. M. Baker, D.-H. T. Nguyen, D. M. Cohen, E. Toro, A. A. Chen, P. A. Galie, and X. Yu, *Rapid casting of patterned vascular networks for perfusable engineered three-dimensional tissues.* Nature materials, 2012.
27. Greiner, A. M., B. Richter, and M. Bastmeyer, *Micro Engineered 3D Scaffolds for Cell Culture Studies.* Macromolecular bioscience, 2012. 12(10): p. 1301-1314.
28. Xu, C., W. Chai, Y. Huang, and R. R. Markwald, *Scaffold free inkjet printing of three-dimensional zigzag cellular tubes.* Biotechnology and Bioengineering, 2012. 109(12): p. 3152-3160.
29. Gilbert, T. W., T. L. Sellaro, and S. F. Badylak, *Decellularization of tissues and organs.* Biomaterials, 2006. 27(19): p. 3675-3683.
30. Crapo, P. M., T. W. Gilbert, and S. F. Badylak, *An overview of tissue and whole organ decellularization processes.* Biomaterials, 2011. 32(12): p. 3233-3243.
31. Amensag, S. and P. S. McFetridge, *Rolling the human amnion to engineer laminated vascular tissues.* Tissue Engineering Part C: Methods, 2012. 18(11): p. 903-912.
32. Amensag, S. and P. S. McFetridge, *Tuning scaffold mechanics by laminating native extracellular matrix membranes and effects on early cellular remodeling.* Journal of Biomedical Materials Research Part A, 2013.
33. Jin, C. Z., S. R. Park, B. H. Choi, K.-Y. Lee, C. K. Kang, and B.-H. Min, *Human amniotic membrane as a delivery matrix for articular cartilage repair.* Tissue engineering, 2007. 13(4): p. 693-702.
34. Mligiliche, N., K. Endo, K. Okamoto, E. Fujimoto, and C. Ide, *Extracellular matrix of human amnion manufactured into tubes as conduits for peripheral nerve regeneration.* Journal of biomedical materials research, 2002. 63(5): p. 591-600.
35. Mohammad, J., J. Shenaq, E. Rabinovsky, and S. Shenaq, *Modulation of peripheral nerve regeneration: a tissue-engineering approach. The role of amnion tube nerve conduit across a 1-centimeter nerve gap.* Plastic and reconstructive surgery, 2000. 105(2): p. 660-666.
36. Ott, H. C., T. S. Matthiesen, S.-K. Goh, L. D. Black, S. M. Kren, T. I. Netoff, and D. A. Taylor, *Perfusion-decellularized matrix: using nature's platform to engineer a bioartificial heart.* Nature medicine, 2008. 14(2): p. 213-221.
37. Petersen, T. H., E. A. Calle, L. Zhao, E. J. Lee, L. Gui, M. B. Raredon, K. Gavrilov, T. Yi, Z. W. Zhuang, and C. Breuer, *Tissue-engineered lungs for in vivo implantation.* Science, 2010. 329(5991): p. 538-541.
38. Guo, S., X. Ren, B. Wu, and T. Jiang, *Preparation of the acellular scaffold of the spinal cord and the study of biocompatibility.* Spinal cord, 2010. 48(7): p. 576-581.
39. Uygun, B. E., A. Soto-Gutierrez, H. Yagi, M.-L. Izamis, M. A. Guzzardi, C. Shulman, J. Milwid, N. Kobayashi, A. Tilles, and F. Berthiaume, *Organ reengineering through development of a transplantable recellularized liver graft using decellularized liver matrix.* Nature medicine, 2010. 16(7): p. 814-820.
40. Baiguera, S., P. Jungebluth, A. Burns, C. Mavilia, J. Haag, P. De Coppi, and P. Macchiarini, *Tissue engineered human tracheas for in vivo implantation.* Biomaterials, 2010. 31(34): p. 8931-8938.
41. Roberts, G. P. and H. A. Barnes, *New measurements of the flow-curves for Carbopol dispersions without slip artefacts.* Rheologica acta, 2001. 40(5): p. 499-503.

42. Piau, J., *Carbopol gels: Elastoviscoplastic and slippery glasses made of individual swollen sponges: Meso-and macroscopic properties, constitutive equations and scaling laws.* Journal of non-newtonian fluid mechanics, 2007. 144(1): p. 1-29.
43. Barnes, H. A., *The yield stress—a review or 'παντα ρει'—everything flows?* Journal of non-newtonian fluid mechanics, 1999. 81(1): p. 133-178.
44. Møller, P. C., J. Mewis, and D. Bonn, *Yield stress and thixotropy: on the difficulty of measuring yield stresses in practice.* Soft matter, 2006. 2(4): p. 274-283.
45. Romeo, G., A. Fernandez-Nieves, H. M. Wyss, D. Acierno, and D. A. Weitz, *Temperature-Controlled Transitions Between Glass, Liquid, and Gel States in Dense p-NIPA Suspensions.* Advanced Materials, 2010. 22(31): p. 3441-3445.
46. Bindschadler, M. and J. L. McGrath, *Sheet migration by wounded monolayers as an emergent property of single-cell dynamics.* J Cell Sci, 2007. 120(5): p. 876-884.
47. Trepat, X., M. R. Wasserman, T. E. Angelini, E. Millet, D. A. Weitz, J. P. Butler, and J. J. Fredberg, *Physical forces during collective cell migration.* Nat Phys, 2009. 5.
48. Poujade, M., E. Grasland-Mongrain, A. Hertzog, J. Jouanneau, P. Chavrier, B. Ladoux, A. Buguin, and P. Silberzan, *Collective migration of an epithelial monolayer in response to a model wound.* Proceedings of the National Academy of Sciences, 2007. 104(41): p. 15988-15993.
49. Szabo, B., G. J. Szollosi, B. Gonci, Z. Juranyi, D. Selmeczi, and T. Vicsek, *Phase transition in the collective migration of tissue cells: Experiment and model.* Physical Review E (Statistical, Nonlinear, and Soft Matter Physics), 2006. 74(6): p. 061908-5.
50. Kurten, R. C., P. Chowdhury, R. C. Sanders, Jr., L. M. Pittman, L. W. Sessions, T. C. Chambers, C. S. Lyle, B. J. Schnackenberg, and S. M. Jones, *Coordinating epidermal growth factor-induced motility promotes efficient wound closure.* Am J Physiol Cell Physiol, 2005. 288(1): p. C109-121.
51. Haga, H., C. Irahara, R. Kobayashi, T. Nakagaki, and K. Kawabata, *Collective Movement of Epithelial Cells on a Collagen Gel Substrate.* Biophysical Journal, 2005. 88(3): p. 2250-2256.
52. Farooqui, R. and G. Fenteany, *Multiple rows of cells behind an epithelial wound edge extend cryptic lamellipodia to collectively drive cell-sheet movement.* J Cell Sci, 2005. 118(1): p. 51-63.
53. Tambe, D. T., C. C. Hardin, T. E. Angelini, K. Rajendran, C. Y. Park, X. Serra-Picamal, E. H. Zhou, M. H. Zaman, J. P. Butler, and D. A. Weitz, *Collective cell guidance by cooperative intercellular forces.* Nature materials, 2011. 10(6): p. 469-475.
54. Angelini, T. E., E. Hannezo, X. Trepat, J. J. Fredberg, and D. A. Weitz, *Cell Migration Driven by Cooperative Substrate Deformation Patterns.* Physical Review Letters, 2010. 104(16): p. 168104.
55. Angelini, T. E., E. Hannezo, X. Trepat, M. Marquez, J. J. Fredberg, and D. A. Weitz, *Glass-like dynamics of collective cell migration.* Proceedings of the National Academy of Sciences, 2011. 108(12): p. 4714-4719.
56. Suaris, M., J. A. Breaux, S. P. Zehnder, and T. E. Angelini. *Nucleation and growth of epithelial cell clusters.* in *AIP Conference Proceedings.* 2013.
57. Saunders, B. R. & Vincent, B. *Microgel particles as model colloids: theory, properties and applications.* Advances in Colloid and Interface Science 80, 1-25 (1999).
58. O'Hern, C. S., Silbert, L. E., Liu, A. J. & Nagel, S. R. *Jamming at zero temperature and zero applied stress: The epitome of disorder.* Physical Review E 68, 011306 (2003).
59. Liu, A. J. & Nagel, S. R. *Nonlinear dynamics: Jamming is not just cool any more.* Nature 396, 21-22 (1998).
60. Cates, M., Wittmer, J., Bouchaud, J.-P. & Claudin, P. *Jamming, force chains, and fragile matter.* Physical review letters 81, 1841 (1998).
61. Liu, A. J. & Nagel, S. R. *Jamming and rheology: constrained dynamics on microscopic and macroscopic scales.* (CRC Press, 2001).
62. Bi, D., Zhang, J., Chakraborty, B. & Behringer, R. *Jamming by shear.* Nature 480, 355-358 (2011).
63. Corwin, E. I., Jaeger, H. M. & Nagel, S. R. *Structural signature of jamming in granular media.* Nature 435, 1075-1078 (2005).
64. Schweizer, K. S. & Yatsenko, G. *Collisions, caging, thermodynamics, and jamming in the barrier hopping theory of glassy hard sphere fluids.* The Journal of chemical physics 127, 164505 (2007).
65. Cho, E. C., Kim, J.-W., Fernández-Nieves, A. & Weitz, D. A. *Highly responsive hydrogel scaffolds formed by three-dimensional organization of microgel nanoparticles.* Nano letters 8, 168-172 (2008).
66. Fernandez-Nieves, A., Wyss, H., Mattsson, J. & Weitz, D. A. *Microgel suspensions: fundamentals and applications.* (John Wiley & Sons, 2010).
67. Debord, J. D., Eustis, S., Byul Debord, S., Lofye, M. T. & Lyon, L. A. *Color-Tunable Colloidal Crystals from Soft Hydrogel Nanoparticles.* Advanced materials 14, 658-662 (2002).
68. Banigan, E. J., Illich, M. K., Stace-Naughton, D. J. & Egolf, D. A. *The chaotic dynamics of jamming.* Nature Physics 9, 288-292 (2013).
69. Gratson, G. M., Xu, M. & Lewis, J. A. *Microperiodic structures: Direct writing of three-dimensional webs.* Nature 428, 386-386 (2004).
70. Stringer, J. & Derby, B. *Formation and stability of lines produced by inkjet printing.* Langmuir 26, 10365-10372 (2010).
71. Ahn, B. Y. et al. *Omnidirectional printing of flexible, stretchable, and spanning silver microelectrodes.* Science 323, 1590-1593 (2009).
72. Murphy, S. V. & Atala, A. *3D bioprinting of tissues and organs.* Nature biotechnology (2014).
73. Wu, W., DeConinck, A. & Lewis, J. A. *Omnidirectional printing of 3D microvascular networks.* Advanced materials 23, H178-H183 (2011).
74. Muth, J. T. et al. *Embedded 3D Printing of Strain Sensors within Highly Stretchable Elastomers.* Advanced materials 26, 6307-6312 (2014).
75. Glotzer, S. C. & Solomon, M. J. *Anisotropy of building blocks and their assembly into complex structures.* Nature materials 6, 557-562 (2007).
76. Narayan, V., Ramaswamy, S. & Menon, N. *Long-lived giant number fluctuations in a swarming granular nematic.* Science 317, 105-108 (2007).
77. Shi, X.-q. & Ma, Y.-q. *Topological structure dynamics revealing collective evolution in active nematics.* Nature communications 4 (2013).
78. Wang, N. et al. *Cell prestress. I. Stiffness and prestress are closely associated in adherent contractile cells.* American Journal of Physiology-Cell Physiology 282, C606-C616 (2002).

79. Utada, A. et al. *Monodisperse double emulsions generated from a microcapillary device.* Science 308, 537-541 (2005).
80. Teh, S.-Y., Lin, R., Hung, L.-H. & Lee, A. P. *Droplet microfluidics.* Lab on a Chip 8, 198-220 (2008).
81. Tompkins, N. et al. *Testing Turing's theory of morphogenesis in chemical cells.* Proceedings of the National Academy of Sciences 111, 4397-4402 (2014).
82. Zhang, J. et al. *One-step fabrication of supramolecular microcapsules from microfluidic droplets.* Science 335, 690-694 (2012).

Computing Environment

Figure 35:
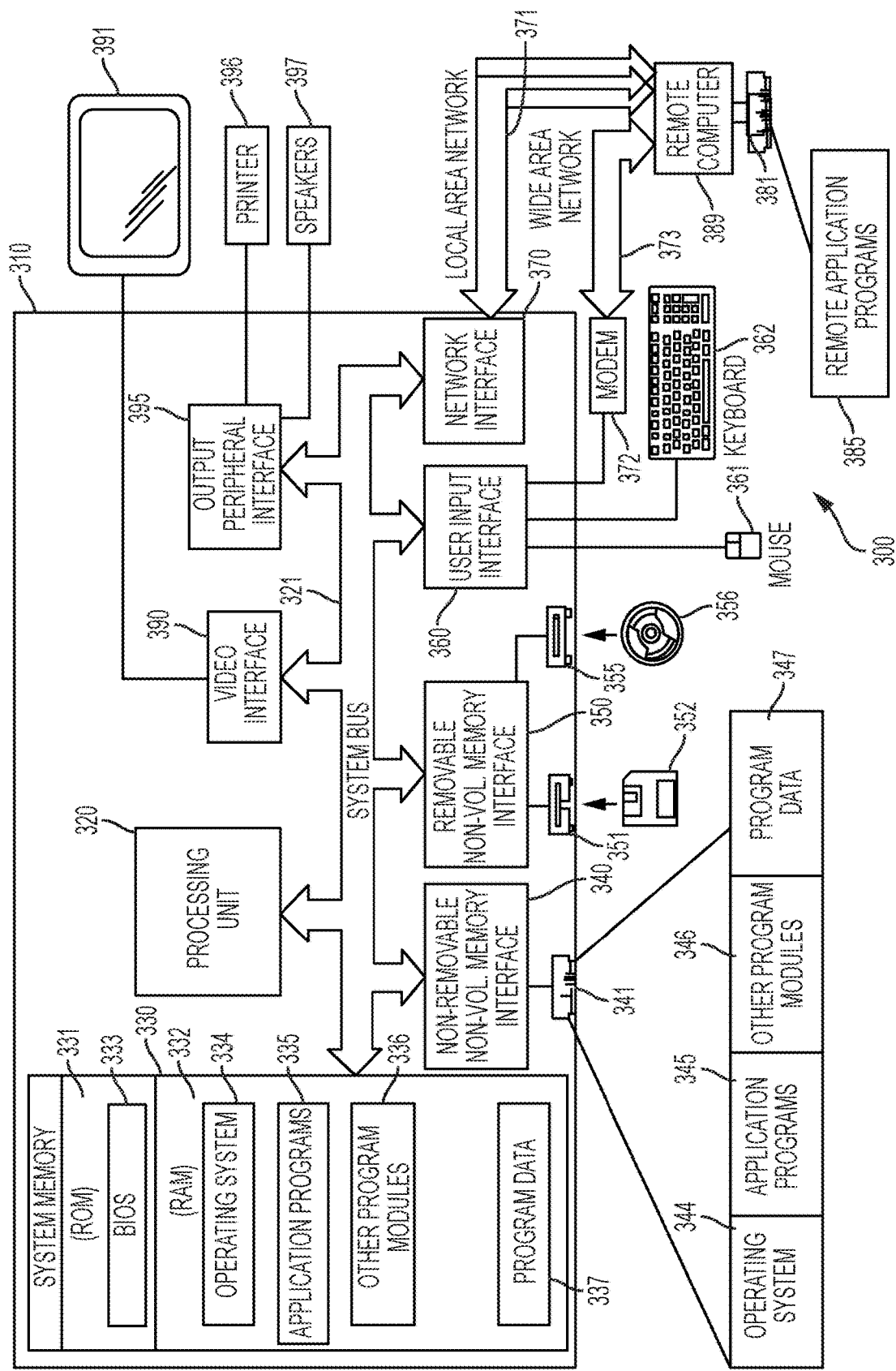
FIG. 35 is a diagram illustrating a computer system on which some embodiments may be implemented.

Techniques as described herein may be implemented on any suitable hardware, including a programmed computing system. For example, analysis of a scan and construction of a model may be performed by programming a computing device. Similarly, control of a 3D printing device to print biomaterials in accordance with a model may be controlled by a programmed computing device. FIG. 13 illustrates a system that may be implemented with multiple computing devices, which may be distributed and/or centralized. Also, FIG. 16 illustrates a process that may include algorithms executing on at least one computing device. FIG. 35 illustrates an example of a suitable computing system environment 300 on which embodiments of these algorithms may be implemented. This computing system may be representative of a computing system that implements the techniques described herein. However, it should be appreciated that the computing system environment 300 is only one example of a suitable computing environment and is not intended to suggest any limitation as to the scope of use or functionality of the invention. Neither should the computing environment 300 be interpreted as having any dependency or requirement relating to any one or combination of components illustrated in the exemplary operating environment 300.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments or cloud-based computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 35, an exemplary system for implementing the invention includes a general purpose computing device in the form of a computer 310. Though a programmed general purpose computer is illustrated, it should be understood by one of skill in the art that algorithms may be implemented in any suitable computing device. Accordingly, techniques as described herein may be implemented in any suitable system. These techniques may be implemented in such network devices as originally manufactured or as a retrofit, such as by changing program memory devices holding programming for such network devices or software download. Thus, some or all of the components illustrated in FIG. 35, though illustrated as part of a general purpose computer, may be regarded as representing portions of a node or other component in a network system.

Components of computer 310 may include, but are not limited to, a processing unit 320, a system memory 330, and a system bus 321 that couples various system components including the system memory 330 to the processing unit 320. The system bus 321 may be any of several types of bus structures including a memory bus or memory controller, a peripheral bus, and a local bus using any of a variety of bus architectures. By way of example and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 310 typically includes a variety of computer readable media. Computer readable media can be any available media that can be accessed by computer 310 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can by accessed by computer 310. Communication media typically embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example and not limitation, communication media includes wired media such as a wired network or direct-wired connection, and wireless media such as acoustic, radio frequency (RF), infrared (IR), and other wireless media. Combinations of any of the above should also be included within the scope of computer readable media.

The system memory 330 includes computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 typically contains data and/or program modules that are immediately accessible to and/or presently being operated on by processing unit 320. By way of example and not limitation, FIG. 35 illustrates operating system 334, application programs 335, other program modules 336, and program data 337.

The computer 310 may also include other removable/non-removable, volatile/nonvolatile computer storage media. By way of example only, FIG. 35 illustrates a hard disk drive 341 that reads from or writes to non-removable, nonvolatile magnetic media, a magnetic disk drive 351 that reads from or writes to a removable, nonvolatile magnetic disk 352, and an optical disk drive 355 that reads from or writes to a removable, nonvolatile optical disk 356 such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 341 is typically connected to the system bus 321 through an non-removable memory interface such as interface 340, and magnetic disk drive 351 and optical disk drive 355 are typically connected to the system bus 321 by a removable memory interface, such as interface 350.

The drives and their associated computer storage media discussed above and illustrated in FIG. 35, provide storage of computer readable instructions, data structures, program modules, and other data for the computer 310. In FIG. 35, for example, hard disk drive 341 is illustrated as storing operating system 344, application programs 345, other program modules 346, and program data 347. Note that these components can either be the same as or different from operating system 334, application programs 335, other program modules 336, and program data 337. Operating system 344, application programs 345, other program modules 346, and program data 347 are given different numbers here to illustrate that, at a minimum, they are different copies. A user may enter commands and information into the computer 310 through input devices such as a keyboard 362 and pointing device 361, commonly referred to as a mouse, trackball, or touch pad. Other input devices (not shown) may include a microphone, joystick, game pad, satellite dish, scanner, or the like. These and other input devices are often connected to the processing unit 320 through a user input interface 360 that is coupled to the system bus, but may be connected by other interface and bus structures, such as a parallel port, game port, or a universal serial bus (USB). A monitor 391 or other type of display device is also connected to the system bus 321 via an interface, such as a video interface 390. In addition to the monitor, computers may also include other peripheral output devices such as speakers 397 and printer 396, which may be connected through an output peripheral interface 395.

The computer 310 may operate in a networked environment using logical connections to one or more remote computers, such as a remote computer 380. The remote computer 380 may be a personal computer, a server, a router, a network PC, a peer device, or some other common network node, and typically includes many or all of the elements described above relative to the computer 310, although only a memory storage device 381 has been illustrated in FIG. 35. The logical connections depicted in FIG. 35 include a local area network (LAN) 371 and a wide area network (WAN) 373, but may also include other networks. Such networking environments are commonplace in offices, enterprise-wide computer networks, intranets, and the Internet.

When used in a LAN networking environment, the computer 310 is connected to the LAN 371 through a network interface or adapter 370. When used in a WAN networking environment, the computer 310 typically includes a modem 372 or other means for establishing communications over the WAN 373, such as the Internet. The modem 372, which may be internal or external, may be connected to the system bus 321 via the user input interface 360, or other appropriate mechanism. In a networked environment, program modules depicted relative to the computer 310, or portions thereof, may be stored in the remote memory storage device. By way of example and not limitation, FIG. 35 illustrates remote application programs 385 as residing on memory device 381. It will be appreciated that the network connections shown are exemplary and other means of establishing a communications link between the computers may be used.

Having thus described several aspects of at least one embodiment of this invention, it is to be appreciated that various alterations, modifications, and improvements will readily occur to those skilled in the art.

For example, techniques are described in which biomaterials are printed into a first material that temporarily changes for a more solid to a more fluid phase upon introduction of energy. Alternatively, materials that become less fluid upon introduction of energy, such as polymers that cure, might also be used.

As another example, biomaterials containing polymers that may be cross-linked or otherwise cured were described as a way to make a tissue construct with structural integrity from material injected in a liquid phase into the first material. Other materials that can be injected in a fluid state, and converted to a material with structural integrity may alternatively or additionally be used. For example, tissue culture medium, containing live cells that may grow and adhere to one another may alternatively or additionally be used.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the attached claims, various elements are recited in different claims. However, the claimed elements, even if recited in separate claims, may be used together in any suitable combination.

What is claimed is:

1. A method for creating a three-dimensional tissue construct of a desired shape for repair or replacement of tissue of a tissue cavity of an organism, the method comprising:
    injecting at least one biomaterial in a three-dimensional pattern into a yield stress material such that the at least one biomaterial is held in the desired shape of the tissue construct by the yield stress material,
    wherein the yield stress material is a Herschel-Bulkley material comprising a soft granular gel made from polymeric packed microparticles having a yield stress less than 100 Pascals.

2. The method of claim 1, wherein injecting the at least one biomaterial comprises:
    causing a phase change in a region of the yield stress material by applying focused energy to the region using a focused energy source; and
    displacing the first material in the region with the at least one biomaterial.

3. The method of claim 1, wherein the polymeric packed micro-particles are between 0.1 and 100 micrometers in diameter.

4. The method of claim 3, wherein the polymeric packed microparticles comprise a carbomer polymer.

5. The method of claim 4, wherein the carbomer polymer is a carbomer interpolymer, a carbomer homopolymer, or a carbomer copolymer.

6. The method of claim 1, wherein:
the injecting the at least one biomaterial into the yield stress material is performed for a duration of one hour to create the tissue construct.

7. The method of claim 1, wherein:
the at least one biomaterial comprises at least one polymer.

8. The method of claim 7, wherein the at least one polymer comprises one or more naturally-occurring extracellular matrix materials.

9. The method of claim 7, further comprising:
curing the at least one polymer; and
removing the at least one cured biomaterial from the yield stress material, thereby providing the tissue construct.

10. The method of claim 1, wherein the at least one biomaterial comprises one or a combination of collagen, elastin, fibronectin, and laminin.

11. The method of claim 1, wherein injecting the at least one biomaterial comprises:
injecting into the yield stress material, at a location at which growth of tissue of a first type is to be encouraged, a first combination of one or more of collagen, elastin, fibronectin, and laminin; and
injecting into the yield stress material, at a location at which growth of tissue of a second type is to be encouraged, a second combination of one or more of collagen, elastin, fibronectin, and laminin,
the second combination being different from the first combination.

12. The method of claim 1, further comprising:
removing the tissue construct from the yield stress material; and
inserting the tissue construct into the tissue cavity.

13. The method of claim 1, further comprising:
injecting at least one cell in the tissue construct.

14. The method of claim 13, wherein:
injecting the at least one cell comprises injecting a first type of cell and injecting a second type of cell;
injecting the at least one biomaterial comprises injecting a first biomaterial adapted to encourage growth of the first type of cell and injecting a second biomaterial adapted to encourage growth of the second type of cell; and
injecting the at least one cell further comprises injecting the first type of cell at a location adjacent to a location at which the first biomaterial was injected and injecting the second type of cell at a location adjacent to a location at which the second biomaterial was injected.

15. The method of claim 1, wherein the yield stress material has a thixotropic time between 0.25 second and 2.5 second.

16. The method of claim 1, wherein the yield stress material has a thixotropic index between 4 and 7.

17. The method of claim 1, further comprising removing the injected at least one biomaterial from the yield stress material.

18. The method of claim 17, wherein removing the injected at least one biomaterial from the yield stress material comprises washing away the yield stress material.

19. The method of claim 17, further comprising inserting the tissue construct into the tissue cavity of the organism.

20. The method of claim 17, further comprising attaching the tissue construct to the organism at the tissue cavity.

21. The method of claim 1, wherein:
injecting the at least one biomaterial comprises injecting the at least one biomaterial such that the tissue construct has a smallest feature size of less than 1 millimeter.

22. The method of claim 21, wherein injecting the at least one biomaterial comprises injecting the at least one biomaterial such that the tissue construct has a smallest feature size of less than 100 micrometers.

23. The method of claim 21, wherein injecting the at least one biomaterial comprises injecting the at least one biomaterial such that the tissue construct has a smallest feature size of less than 10 micrometers.

24. The method of claim 1, wherein the yield stress material comprises a hydrogel.

25. The method of claim 1, wherein the yield stress of the yield stress material is between 10 and 99 Pascals.

26. The method of claim 1, wherein a shear stress of the yield stress material is independent of shear rate at a shear rate of $10^{-3}$ $s^{-1}$.

27. The method of claim 26, wherein the shear stress of the yield stress material at a shear rate of $10^{-3}$ $s^{-1}$ is dependent only on an elastic component of the yield stress material.

28. The method of claim 1, wherein the yield stress of the yield stress material is below a hydrostatic pressure of the yield stress material.

29. The method of claim 1, further comprising: inserting the tissue construct into the tissue cavity; and following the injecting and prior to the inserting, maintaining the tissue construct in a state that discourages growth of cells and/or tissues,
wherein maintaining the tissue construct in the state comprises refrigerating the tissue construct following the injecting and prior to the inserting.

30. The method of claim 1, further comprising:
at a time less than 48 hours following completion of the injecting to create the tissue construct, inserting the tissue construct into the tissue cavity.

31. The method of claim 1, wherein injecting the at least one biomaterial further comprises injecting at least one cell.

32. The method of claim 1, further comprising:
preparing a model of the tissue construct to be printed, wherein preparing the model of the tissue construct comprises:
scanning a tissue region of the organism in an area of the tissue cavity; and
generating the model of the tissue construct to have:
a first biomaterial adapted to encourage growth of replacement bone tissue adjacent a location of bone identified in the scanning,
a second biomaterial adapted to encourage growth of replacement muscle tissue adjacent a location of muscle identified in the scanning, and/or
a third biomaterial adapted to encourage growth of replacement vasculature tissue adjacent a location of vasculature identified in the scanning.

33. The method of claim 32, wherein:
scanning the tissue region of the organism in the area of the tissue cavity comprises determining a topographic shape of the tissue cavity; and
injecting the at least one biomaterial in the three-dimensional pattern into the yield stress material such that the at least one biomaterial is held in the desired shape comprises injecting the at least one biomaterial into the yield stress material to form a shape having a topographic shape complementary to the topographic shape of the tissue cavity.

34. The method of claim 32, wherein scanning the tissue region of the organism comprises scanning the tissue region using a laser scanner.

35. The method of claim 32, wherein:
preparing the model of the tissue construct further comprises:
   scanning a healthy body part; and
   combining, using at least one processor, a result of the scanning of the tissue region of the organism with a result of the scanning of the healthy body part, and
generating the model of the tissue construct comprises generating the model of the tissue construct based on a result of the combining.

36. The method of claim 35, wherein scanning the healthy body part comprises scanning the healthy body part with one or more of a laser scanner, an x-ray device, a computerized tomography (CT) device, or a magnetic resonance imaging (MRI) device.

37. The method of claim 35, wherein scanning the healthy body part comprises scanning the healthy body part with one or more device to image an exterior and/or interior anatomy of the healthy body part.

38. The method of claim 35, wherein scanning the healthy body part comprises scanning a tissue region of the organism having an arrangement of tissues corresponding to an arrangement of tissues that would have been disposed in the tissue cavity.

39. The method of claim 38, wherein scanning the tissue region of the organism having the arrangement of tissues corresponding to an arrangement of tissues that would have been disposed in the tissue cavity comprises, in a case that the tissue cavity is in an area of the organism at which anatomy is bilaterally symmetric to anatomy of a second portion of the organism, scanning a tissue region of the second portion of the organism.

\* \* \* \* \*